US011419895B2

(12) United States Patent
Li et al.

(10) Patent No.: US 11,419,895 B2
(45) Date of Patent: Aug. 23, 2022

(54) COMPOSITIONS AND METHODS OF CELLULAR IMMUNOTHERAPY

(71) Applicant: CRAGE medical Co., Limited, Mongkok Kowloon (HK)

(72) Inventors: Zonghai Li, Shanghai (CN); Peng Wang, Shanghai (CN); Hua Jiang, Shanghai (CN)

(73) Assignee: CRAGE medical Co., Limited, Mongkok Kowloon (HK)

(*) Notice: Subject to any disclaimer, the term of this patent is extended or adjusted under 35 U.S.C. 154(b) by 70 days.

(21) Appl. No.: 16/618,047

(22) PCT Filed: May 30, 2018

(86) PCT No.: PCT/CN2018/089061
§ 371 (c)(1),
(2) Date: Nov. 27, 2019

(87) PCT Pub. No.: WO2018/219299
PCT Pub. Date: Dec. 6, 2018

(65) Prior Publication Data
US 2020/0138864 A1 May 7, 2020

(30) Foreign Application Priority Data
May 31, 2017 (WO) ............... PCT/CN2017/086606

(51) Int. Cl.
| | | |
|---|---|---|
| *C07K 16/30* | (2006.01) | |
| *A61K 35/17* | (2015.01) | |
| *A61P 35/00* | (2006.01) | |
| *A61K 38/20* | (2006.01) | |
| *C07K 14/725* | (2006.01) | |
| *C07K 16/28* | (2006.01) | |

(52) U.S. Cl.
CPC ............ *A61K 35/17* (2013.01); *A61K 38/208* (2013.01); *A61P 35/00* (2018.01); *C07K 14/7051* (2013.01); *C07K 16/2809* (2013.01); *C07K 16/2833* (2013.01); *C07K 16/30* (2013.01); *C07K 2317/21* (2013.01); *C07K 2317/31* (2013.01); *C07K 2317/55* (2013.01); *C07K 2317/565* (2013.01); *C07K 2317/622* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 7,728,114 B2 * | 6/2010 | Mach | ................ | A61K 39/3955 530/388.15 |
| 2004/0247609 A1 | 12/2004 | Sugiyama | | |
| 2005/0002951 A1 | 1/2005 | Sugiyama | | |
| 2010/0255020 A1 | 10/2010 | Miyakawa | | |
| 2014/0294841 A1 * | 10/2014 | Scheinberg | ............. | A61P 15/00 424/138.1 |
| 2016/0152725 A1 * | 6/2016 | Cheung | ............... | A61K 51/1045 435/375 |
| 2016/0369006 A1 * | 12/2016 | Scheinberg | ........ | C07K 16/3015 |
| 2017/0101473 A1 * | 4/2017 | Mahr | ................. | G01N 33/6854 |

FOREIGN PATENT DOCUMENTS

| | | |
|---|---|---|
| EP | 1696027 A1 | 8/2006 |
| WO | WO2003028757 A1 | 4/2003 |
| WO | WO2003028758 A1 | 4/2003 |
| WO | WO2005045027 A1 | 5/2005 |
| WO | WO2005056595 A2 | 6/2005 |
| WO | WO2005056595 A3 | 10/2005 |
| WO | WO2009066462 A1 | 5/2009 |
| WO | WO2010023065 A1 | 3/2010 |
| WO | WO-2012109659 A1 * | 8/2012 ......... A61K 39/0011 |
| WO | 2012135854 A2 | 10/2012 |
| WO | 2016199140 A1 | 12/2016 |
| WO | 2017060201 A1 | 4/2017 |

OTHER PUBLICATIONS

Ataie et al. (J Mol Biol (2016) 428, 194-205). (Year: 2016).*
Ataie et al. (J Mol Biol (2016) 428, 194-205 and Supp Data p. 1-5). (Year: 2016).*
Musante et al. (Gene 332 (2004) 119-127). (Year: 2004).*
Harlow et al. (Antibodies, A Laboratory Manual, Cold Spring Harbor laboratory, 1988, pp. 37-47). (Year: 1988).*
Edwards et al. (J. Mol. Biol. (2003) 334, 103-118). (Year: 2003).*
Lloyd et al., Protein Engineering, Design & Selection vol. 22 No. 3 pp. 159-168, 2009. (Year: 2009).*
Meyer et al. (British Journal of Haematology, 2018, 180, 808-820, Supp Figs S1-S4 and pp. 1-5). (Year: 2018).*
Vajdos et al. (J Mol Biol. Jul. 5, 2002;320(2):415-28). (Year: 2002).*
Bedouelle et al. (FEBS J. Jan. 2006;273(1):34-46). (Year: 2006).*
Brown et al. (J Immunol. May 1, 1996;156(9):3285-91). (Year: 1996).*
Colman (Research in Immunology, 145:33-36, 1994). (Year: 1994).*
Rudikoff et al. (Proc. Natl. Acad. Sci. USA, 79: 1979-1983, Mar. 1982). (Year: 1982).*
Hughes et al., Blood. 2017;129(9):1166-1176. (Year: 2017).*
Dao et al., Sci Transl Med. Mar. 13, 2013; 5(176): 176ra33. (Year: 2013).*
Borbulevych, O.Y. et al. (2010, e-pub. Jul. 8, 2010). "Structures of Native and Affinity-Enhanced WT1 Epitopes Bound to HLA-A*0201: Implications for WT1-Based Cancer Therapeutics," Molecular Immunology 47(15):2519-2524, 13 pages.

(Continued)

*Primary Examiner* — Zachary S Skelding
(74) *Attorney, Agent, or Firm* — Nelson Mullins Riley & Scarborough LLP; Jill Gorney Sloper, Esq.

(57) ABSTRACT

Disclosed herein are methods of treating a subject exhibiting a cell that expresses Wilms tumor protein 1 (WT1). The methods typically utilize anti-WT1 antigen binding units or chimeric antigen receptor immunoresponsive cells to a subject in need thereof to effect killing of tumor cells.

10 Claims, 15 Drawing Sheets

Specification includes a Sequence Listing.

(56) References Cited

OTHER PUBLICATIONS

International Search Report, and Written Opinion, dated Jun. 28, 2018, for PCT Application No. PCT/CN2018/089061, filed May 30, 2018, 10 pages.

Rafiq, S. et al., "Optimized T-cell receptor mimic chimeric antigen receptor T cells directed toward the intracellular Wilms Tumor 1 antigen," Leukemia, vol. 31(8):1788-1797 (2017).

Zhao Q et al., "Affinity maturation of T-cell receptor-like antibodies for Wilms tumor 1 peptide greatly enhances therapeutic potential," Leukemia, Nature Publishing Group UK, London, vol. 29(11): 2238-2247 (2015).

\* cited by examiner

FIG. 6

COMPOSITIONS AND METHODS OF CELLULAR IMMUNOTHERAPY

CROSS-REFERENCE

This application is a National Phase application under 35 U.S.C. § 371 of International Application No. PCT/CN2018/089061, filed May 30, 2018, which claims the benefit of International PCT Application No. PCT/CN2017/086606, filed May 31, 2017, which application is incorporated herein by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 794922001100SEQLIST.txt, date recorded: Nov. 20, 2019, size: 99 KB).

BACKGROUND

Cancer has a major impact on society in across the globe. In 2016, an estimated 1,685,210 new cases of cancer will be diagnosed in the United States alone, and 595,690 people will die from the disease. By 2020, 18.2 million Americans, roughly 1 in 19 people, will be cancer patients or cancer survivors, up from 11.7 million (1 in 26) in 2005, according to the Journal of Oncology Practice (Erikson 2007). Cancer has a major impact on society in across the globe. In 2016, an estimated 1,685,210 new cases of cancer will be diagnosed in the United States alone, and 595,690 people will die from the disease. By 2020, 18.2 million Americans, roughly 1 in 19 people, will be cancer patients or cancer survivors, up from 11.7 million (1 in 26) in 2005, according to the *Journal of Oncology Practice* (Erikson 2007).

Chimeric antigen receptors (CARs) are recombinant receptors for antigen, which, in a single molecule, redirect the specificity and function of T cells and other immune cells. Their use in cancer immunotherapy can be to rapidly generate tumor-targeted T cells, bypassing the obstacles of active immunization. Once expressed in cells, the CAR-modified cell may exert both immediate and long-term effects in a subject.

Chimeric antigen receptor (CAR) T cell therapy, which edits a cancer patient's T cells to recognize their tumors, has shown to be effective for treating blood cancers. In recent clinical trials, CAR T cell therapy has dramatically improved the outcomes of blood cancer patients with advanced, otherwise untreatable forms of leukemia and lymphoma. In contract, CAR T cells face a unique set of challenges in the context of solid tumors. Amongst the challenges include the identification of an antigen whose expression clearly demarcates tumor from normal tissue and establishing effective killing of tumor cells within a tumor and hence reduction of tumor size.

SUMMARY OF THE INVENTION

There exists a pressing need for alternative and effective treatment for a wide variety of solid tumors. The present invention addresses this need and provides related advantages as well.

Accordingly, the present invention discloses an antigen binding unit comprising a light chain CDR and a heavy chain CDR, wherein the antigen binding unit specifically binds to a WT1 peptide complexed with HLA, wherein the WT1 peptide has the amino acid sequence of SEQ ID NO: 1, and wherein the antigen binding unit exhibits no significant binding to a reference peptide complexed with HLA, wherein the reference peptide has the amino acid sequence of SEQ ID NO: 58 or SEQ ID NO: 59. Also disclosed herein is an antigen binding unit comprising a light chain CDR and a heavy chain CDR, wherein the antigen binding unit specifically binds to a WT1 peptide complexed with HLA, wherein the WT1 peptide has the amino acid sequence of SEQ ID NO: 1, and wherein the antigen binding unit exhibits less non-specific binding to a reference peptide complexed with HLA as compared to that of a reference antigen binding unit having the amino acid sequence of SEQ ID NO: 60, wherein the reference peptide has the amino acid sequence of SEQ ID NO: 58 or SEQ ID NO: 59. In some cases, the HLA comprises HLA-A2. In some cases, binding level to the reference peptide complexed with HLA can be no more than 10% of binding level to the WT1 peptide complexed with HLA. In some cases, binding specificity can be determined by FACS. In some cases, binding specificity can be determined by ELISA. In some cases, the antigen binding unit can exhibit a $K_D$ of less than 1.5 nM. In some cases, the antigen binding unit can exhibit a $K_D$ of less than 50 pM. In some cases, the light chain CDR can comprise LCDR1, LCDR2, and LCDR3; and the heavy chain CDR can comprise HCDR1, HCDR2, and HCDR3; wherein said LCDR1, LCDR2, and LCDR3 each have a sequence selected from the group consisting of SEQ ID NO: 5-7 and 11-15; and wherein said HCDR1, HCDR2, HCDR3 each have a sequence selected from the group consisting of SEQ ID NO: 2-4, 8-10, and 16-17. In some cases, the light chain CDR can comprise amino acid sequences selected from among the following combinations of LCDR sequences: SEQ ID NO:5, SEQ ID NO:6, and SEQ ID NO:7; SEQ ID NO:11, SEQ ID NO:12, and SEQ ID NO:13; and SEQ ID NO:14, SEQ ID NO:15, and SEQ ID NO:13. In some cases, said heavy chain CDR can comprise amino acid sequences selected from among the following combinations of HCDR sequences: SEQ ID NO:2, SEQ ID NO:3, and SEQ ID NO:4; SEQ ID NO:8, SEQ ID NO:9, and SEQ ID NO:10; SEQ ID NO:8, SEQ ID NO:16, and SEQ ID NO:10; and SEQ ID NO:8, SEQ ID NO:17, and SEQ ID NO:10. In some cases, the antigen binding unit can be a monoclonal antibody, humanized antibody, chimeric antibody, or chimeric antigen receptor. In some cases, the antigen binding unit can be a sFc, Fv, Fab, or (Fab)2.

Disclosed herein is an antigen binding unit comprising a light chain CDR and a heavy chain CDR, wherein the light chain CDR comprises LCDR1, LCDR2, and LCDR3; and the heavy chain CDR comprises HCDR1, HCDR2, and HCDR3, wherein said LCDR1, LCDR2, and LCDR3 each comprises a sequence sharing at least 80% sequence homology to a sequence selected from the group consisting of SEQ ID NO: 5-7 and 11-15, and wherein said HCDR1, HCDR2, and HCDR3 each comprises a sequence having least 80% sequence homology to a sequence selected from the group consisting of SEQ ID NO: 2-4, 8-10, and 16-17. In some cases, the light chain CDR can comprise LCDR1, LCDR2, and LCDR3; and the heavy chain CDR comprises HCDR1, HCDR2, and HCDR3; wherein said LCDR1, LCDR2, and LCDR3 each have a sequence selected from the group consisting of SEQ ID NO: 5-7 and 11-15; and wherein said HCDR1, HCDR2, HCDR3 each have a sequence selected from the group consisting of SEQ ID NO: 2-4, 8-10, and 16-17. In some cases, said light chain CDR can comprise amino acid sequences selected from among the following combinations of LCDR sequences: SEQ ID NO:5, SEQ ID NO:6, and SEQ ID NO:7; SEQ ID NO:11, SEQ ID NO:12, and SEQ ID NO:13; and SEQ ID NO:14, SEQ ID NO:15, and SEQ ID NO:13. In some cases, said heavy chain CDR can comprise amino acid sequences selected from among the following combinations of HCDR sequences: SEQ ID NO:2, SEQ ID NO:3, and SEQ ID NO:4; SEQ ID NO:8, SEQ ID NO:9, and SEQ ID NO:10; SEQ ID NO:8, SEQ ID NO:16, and SEQ ID NO:10; and SEQ ID NO:8, SEQ ID NO:17, and SEQ ID NO:10. In some cases, the antigen binding unit can be a monoclonal antibody, humanized antibody, chimeric antibody, or chimeric antigen receptor. In some cases, the antigen binding unit can be a scFv, Fv, Fab, or (Fab)2.

Disclosed herein is a chimeric antigen receptor comprising an extracellular antigen binding unit, a transmembrane domain, and an intracellular domain, wherein the extracellular antigen binding unit specifically binds to a WT1 peptide complexed with HLA, wherein the WT1 peptide has the amino acid sequence of SEQ ID NO: 1, and wherein the extracellular antigen binding unit exhibits no significant binding to a reference peptide complexed with HLA, wherein the reference peptide has the amino acid sequence of SEQ ID NO: 58 or SEQ ID NO: 59. Also disclosed herein is a chimeric antigen receptor comprising an extracellular antigen binding unit, a transmembrane domain, and an intracellular domain, wherein the extracellular antigen binding unit specifically binds to a WT1 peptide complexed with HLA, wherein the WT1 peptide has the amino acid sequence of SEQ ID NO: 1, and wherein the extracellular antigen binding unit exhibits less non-specific binding to a reference peptide complexed with HLA as compared to that of a reference antigen binding unit having the amino acid sequence of SEQ ID NO: 60, wherein the reference peptide has the amino acid sequence of SEQ ID NO: 58 or SEQ ID NO: 59. In some cases, the extracellular antigen binding unit can comprise a light chain CDR and a heavy chain CDR, and wherein the light chain CDR comprises LCDR1, LCDR2, and LCDR3; and the heavy chain CDR comprises HCDR1, HCDR2, and HCDR3; wherein said LCDR1, LCDR2, and LCDR3 each have a sequence selected from the group consisting of SEQ ID NO: 5-7 and 11-15; and wherein said HCDR1, HCDR2, HCDR3 each have a sequence selected from the group consisting of SEQ ID NO: 2-4, 8-10, and 16-17. In some cases, said light chain CDR can comprise amino acid sequences selected from among the following combinations of LCDR sequences: SEQ ID NO:5, SEQ ID NO:6, and SEQ ID NO:7; SEQ ID NO:11, SEQ ID NO:12, and SEQ ID NO:13; and SEQ ID NO:14, SEQ ID NO:15, and SEQ ID NO:13. In some cases, wherein said heavy chain CDR can comprise amino acid sequences selected from among the following combinations of HCDR sequences: SEQ ID NO:2, SEQ ID NO:3, and SEQ ID NO:4; SEQ ID NO:8, SEQ ID NO:9, and SEQ ID NO:10; SEQ ID NO:8, SEQ ID NO:16, and SEQ ID NO:10; and SEQ ID NO:8, SEQ ID NO:17, and SEQ ID NO:10. In some cases, the intracellular domain can comprise the amino acid sequence of SEQ ID NO: 46, SEQ ID NO: 61, SEQ ID NO: 62, or SEQ ID NO: 66. In some cases, the chimeric antigen receptor can induce cytotoxicity of cells comprising WT1 or a WT1 peptide complexed with HLA. In some cases, the level of cytotoxicity can be at least 5%, 10%, 15%, 20%, 25%, 30%, 35%, 40%, or 45% when the ratio of chimeric antigen receptor to target cell is 20:1, 10:1, 5:1, 3:1, 2.5:1, 1:1, or 1:3.

Disclosed herein is a pharmaceutical composition comprising the antigen binding unit disclosed herein or the chimeric antigen receptor disclosed herein, and a pharmaceutically acceptable excipient. Disclosed herein is an isolated nucleic acid encoding the antigen binding unit disclosed herein or the chimeric antigen receptor disclosed herein. Disclosed herein is a vector comprising a nucleic acid sequence encoding the antigen binding unit disclosed herein or the chimeric antigen receptor disclosed herein. Disclosed herein is a host cell expressing the antigen binding unit disclosed herein or the chimeric antigen receptor disclosed herein. Disclosed herein is a host cell comprising a nucleic acid encoding the antigen binding unit disclosed herein or the chimeric antigen receptor disclosed herein. Disclosed herein is a method of producing the antigen binding unit disclosed herein, comprising: culturing the host cell disclosed herein under conditions suitable for expressing the antigen binding unit; and isolating said antigen binding unit expressed by the host cell. Disclosed herein is a method of producing the chimeric antigen receptor disclosed herein, comprising: culturing the host cell disclosed herein under conditions suitable for expressing the chimeric antigen receptor; and isolating said chimeric antigen receptor expressed by the host cell.

Disclosed herein is a method of inducing death of cells, comprising a WT1 peptide complexed with HLA, said method comprising contacting the cell with the chimeric antigen receptor disclosed herein. In some cases, the cell can be contacted with the chimeric antigen receptor in vivo. In some cases, the cell can be contacted with the chimeric antigen receptor in vitro. In some cases, the cell can be a cancer cell. In some cases, the cell can be a hematological cancer cell or a solid tumor cell. In some cases, the cell can be a nephroblastoma cell, colon cancer cell, rectal cancer cell, ovarian cancer cell, chronic myeloid leukemia cell, or intestinal cancer cell. In some cases, the cell can be a mesothelioma cancer cell.

Disclosed herein is a method of inducing death of target cells, the method comprising administering to the target cells a plurality host cells disclosed herein, wherein administering the plurality of host cells to the target cells induces a greater degree of target cell death relative to administering a comparable amount of host cells lacking said antigen binding unit, chimeric antigen receptor, or nucleic acid encoding the same. In some cases, the plurality of host cells can be administered to the target cells in vivo. In some cases, the plurality of host cells can be administered to the target cells in vitro. In some cases, the target cells can be cancer cells. In some cases, the cancer cells can be a hematological cancer cells or a solid tumor cells. In some cases, the cell can be a nephroblastoma cell, colon cancer cell, rectal cancer cell, ovarian cancer cell, chronic myeloid leukemia cell, or intestinal cancer cell. In some cases, the cell can be a mesothelioma cancer cell.

Disclosed herein is a method of treating a cancer in a subject in need thereof, said method comprising administering to the subject an effective amount of the chimeric antigen receptor disclosed herein, wherein the chimeric antigen receptor induces death of cancer cells. Disclosed herein is a method of treating a cancer in a subject in need thereof, said method comprising administering to the subject an effective amount of the antigen binding unit disclosed herein or the chimeric antigen receptor disclosed herein. Disclosed herein is a method of treating a cancer in a subject in need thereof, said method comprising administering to the subject an effective amount of the pharmaceutical composition disclosed herein. In some cases, the cancer can be a hematological cancer or a solid tumor. In some cases, the cancer can be a mesothelioma. In some cases, the cancer can be nephroblastoma, colon cancer, rectal cancer, ovarian cancer, chronic myeloid leukemia, or intestinal cancer.

Disclosed herein is an immunoresponsive cell comprising a chimeric antigen receptor as described herein, and IL-12. In some cases, the IL-12 is expressed on the surface of the immunoresponsive cell. In other cases, the IL-12 is expressed within the immunoresponsive cell. In some embodiments, the immunoresponsive cell comprising a chimeric antigen receptor as described herein and IL-12 has a cytotoxicity of at least 20%, at least 30%, at least 40%, at least 50%, or at least 60%. In some cases, the immunoresponsive cell has a cytotoxicity of at least 20%, at least 30%, at least 40%, at least 50%, or at least 60% at an effector:target (E:T) ratio of 5:1, 10:1, 15:1, 20:1, or a combination thereof. An immunoresponsive cell comprising a chimeric antigen receptor as described herein and IL-12 can induce death in a target cell. In some cases, the target cell comprises a WT1 peptide complexed with HLA. Also described herein is a method of inducing death of a cell comprising WT1 peptide complexed with HLA in a subject in need thereof, said method comprising administering to the subject an effective amount of an immunoresponsive cell comprising a chimeric antigen receptor described herein and IL-12.

INCORPORATION BY REFERENCE

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

BRIEF DESCRIPTION OF THE DRAWINGS

The novel features of the disclosure are set forth with particularity in the appended claims. A better understanding of the features and advantages of the disclosure will be obtained by reference to the following detailed description that sets forth illustrative embodiments, in which the principles of the disclosure can be utilized, and the accompanying drawings of which:

FIG. 6 depicts a sequence alignment from select antigen binding units.

DETAILED DESCRIPTION OF THE DISCLOSURE

Figure 1:
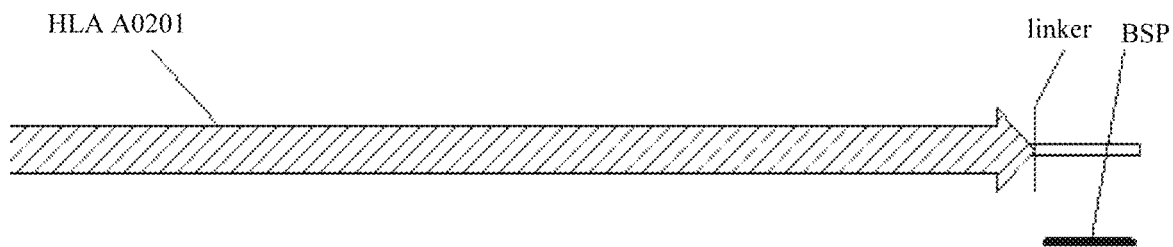
FIG. 1 depicts a cartoon image of a fusion HLA.A0201-BSP gene.

The following description and examples illustrate embodiments of the disclosure in detail. It is to be understood that this disclosure is not limited to the particular embodiments described herein and as such can vary. Those of skill in the art will recognize that there are numerous variations and modifications of the disclosure, which are encompassed within its scope. Unless otherwise indicated, any embodiment can be combined with any other embodiment.

As used herein, unless otherwise indicated, some inventive embodiments herein contemplate numerical ranges. A variety of aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range as if explicitly written out. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. When ranges are present, the ranges include the range endpoints.

Definitions

As used herein, unless otherwise indicated, the article "a" means one or more unless explicitly otherwise provided for.

As used herein, unless otherwise indicated, terms such as "contain," "containing," "include," "including," and the like mean "comprising".

The term "activation" and its grammatical equivalents as used herein can refer to a process whereby a cell transitions from a resting state to an active state. This process can comprise a response to an antigen, migration, and/or a phenotypic or genetic change to a functionally active state. For example, the term "activation" can refer to the stepwise process of T cell activation. For example, a T cell can require at least two signals to become fully activated. The first signal can occur after engagement of a TCR by the antigen-MHC complex, and the second signal can occur by engagement of co-stimulatory molecules (Table 4). Anti-CD3 can mimic the first signal and anti-CD28 can mimic the second signal in vitro. For example, an engineered T cell can be activated by an expressed CAR. T cell activation" or T cell triggering, as used herein, can refer to the state of a T cell that has been sufficiently stimulated to induce detectable cellular proliferation, cytokine production and/or detectable effector function.

The term "antigen binding unit" as used herein refers to an immunoglobulin molecule and immunologically active portions of immunoglobulin molecule, i.e., a molecule that contains an antigen-binding site which specifically binds ("immunoreacts with") an antigen. Also encompassed within the term "antigen binding unit" are immunoglobulin molecules of a variety of species origins including invertebrates and vertebrates. Structurally, the simplest naturally occurring antibody (e.g., IgG) comprises four polypeptide chains, two heavy (H) chains and two light (L) chains inter-connected by disulfide bonds. The immunoglobulins represent a large family of molecules that include several types of molecules, such as IgD, IgG, IgA, IgM and IgE. The term "immunoglobulin molecule" includes, for example, hybrid antibodies, or altered antibodies, and fragments thereof. It has been shown that the antigen binding function of an antibody can be performed by fragments of a naturally-occurring antibody. These fragments are collectively termed "antigen-binding units". Also encompassed within the term "antigen binding unit" is any polypeptide chain-containing molecular structure that has a specific shape which fits to and recognizes an epitope, where one or more non-covalent binding interactions stabilize the complex between the molecular structure and the epitope.

An antigen binding unit "specifically binds to" or "immunoreactive with" an antigen if it binds with greater affinity or avidity than it binds to other reference antigens including polypeptides or other substances.

"Antigen" as used herein means a substance that is recognized and bound specifically by an antigen binding unit. Antigens can include peptides, proteins, glycoproteins, polysaccharides, and lipids; portions thereof and combinations thereof. Non-limiting exemplary antigen included Wilms tumor protein 1 (WT1) from human, murine, and other homologues thereof. "Antigen" can also refer to a molecule that provokes the immune response. This immune response may involve either antibody production, or the activation of specific immunologically-competent cells, or both. The skilled artisan will understand that any macromolecule, including virtually all proteins or peptides, can serve as an antigen.

The term "immunoglobulin" or "Ig", as used herein can refer to a class of proteins, which function as antibodies. Antibodies expressed by B cells are sometimes referred to as the chimeric antigen receptor or antigen receptor. The five members included in this class of proteins are IgA, IgG, IgM, IgD, and IgE, of which IgG is the most common circulating antibody. It is the most efficient immunoglobulin in agglutination, complement fixation, and other antibody responses, and is important in defense against bacteria and viruses. For example, a tumor cell antigen can be recognized by a CAR.

The term "anti-WT1 antibody" can refer to an antibody or antibody binding site that is capable of binding WT1 or a WT1 peptide with sufficient affinity such that the antibody is useful for distinguishing WT1 or a WT1 peptide from other antigens expressed by a cell. In one embodiment, the extent of binding of an anti-WT1 antibody to an unrelated, non-WT1 protein is less than about 10% of the binding of the antibody to WT1 or a WT1 peptide as measured, e.g., by a radioimmunoassay (RIA). In certain embodiments, an antibody that binds to WT1 can have a dissociation constant (Kd) of <1 µM, <100 nM, <10 nM, <5 nM, <4 nM, <3 nM, <2 nM, <1 nM, <0.1 nM, <0.01 nM, or <0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-WT1 antibody binds to an epitope of WT1 that is conserved among WT1 from different species.

The term "autologous" and its grammatical equivalents as used herein can refer to as originating from the same being. For example, a sample (e.g., cells) can be removed, processed, and given back to the same subject (e.g., patient) at a later time. An autologous process is distinguished from an allogenic process where the donor and the recipient are different subjects.

"Xenotransplantation" and its grammatical equivalents as used herein can encompass any procedure that involves transplantation, implantation, or infusion of cells, tissues, or organs into a recipient, where the recipient and donor are different species. Transplantation of the cells, organs, and/or tissues described herein can be used for xenotransplantation in into humans. Xenotransplantation includes but is not limited to vascularized xenotransplant, partially vascularized xenotransplant, unvascularized xenotransplant, xenodressings, xenobandages, and xenostructures.

"Allotransplantation" and its grammatical equivalents (e.g., allogenic transplantation) as used herein can encompass any procedure that involves transplantation, implantation, or infusion of cells, tissues, or organs into a recipient, where the recipient and donor are the same species but different individuals. Transplantation of the cells, organs, and/or tissues described herein can be used for allotransplantation into humans. Allotransplantation includes but is not limited to vascularized allotransplant, partially vascularized allotransplant, unvascularized allotransplant, allodressings, allobandages, and allostructures.

"Autotransplantation" and its grammatical equivalents (e.g., autologous transplantation) as used herein can encompass any procedure that involves transplantation, implantation, or infusion of cells, tissues, or organs into a recipient, where the recipient and donor is the same individual. Transplantation of the cells, organs, and/or tissues described herein can be used for autotransplantation into humans. Autotransplantation includes but is not limited to vascularized autotransplantation, partially vascularized autotransplantation, unvascularized autotransplantation, autodressings, autobandages, and autostructures.

The term "chimeric antigen receptor" or "CAR" as used herein refers to an engineered molecule, which can be expressed by an immune cell including but not limited to T cells. CAR when expressed in T cells and can redirect T cells to induce killing of a target cell with a specificity dictated by the artificial receptor. The CAR's extracellular binding domain can be derived from a murine, humanized, or fully human monoclonal antibody. An "anti-WT1-CAR" is a CAR that is capable of binding to WT1 or a WT1 peptide.

The term "epitope" and its grammatical equivalents as used herein can refer to a part of an antigen that can be recognized by antibodies, B cells, T cells or engineered cells. For example, an epitope can be a cancer epitope that is recognized by a TCR. Multiple epitopes within an antigen can also be recognized. The epitope can also be mutated.

The term "engineered" and its grammatical equivalents as used herein can refer to one or more alterations of a nucleic acid, e.g., the nucleic acid within an organism's genome. The term "engineered" can refer to alterations, additions, and/or deletion of genes. An engineered cell can also refer to a cell with an added, deleted and/or altered gene.

The term "cell" or "engineered cell" and their grammatical equivalents as used herein can refer to a cell of human or non-human animal origin. An engineered cell can also refer to a CAR-expressing cell.

The term "good manufacturing practices" (GMP) and its grammatical equivalents as used herein can refer to products that are safe, effective, or pure according to the FDA. GMP can also sometimes be referred to as "cGMP". The "c" stands for "current." Manufacturers of a product can employ technologies and systems which are up-to-date in order to comply with regulation of GMP products. GMP compatible products are typically utilized in the clinical setting as opposed to the research setting.

A "host cell" includes an individual cell or cell culture which can be or has been a recipient for the subject vectors. Host cells include progeny of a single host cell. The progeny may not necessarily be completely identical (in morphology or in genomic of total DNA complement) to the original parent cell due to natural, accidental, or deliberate mutation. A host cell includes cells transfected in vivo with a vector of this invention. A "host cell" can refer to a prokaryotic cell, a eukaryotic cell, or cell line cultured as a unicellular entity which can be, or has been, used as a recipient for a recombinant vector or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

A "cell line" or "cell culture" denotes bacterial, plant, insect or higher eukaryotic cells grown or maintained in vitro. The descendants of a cell may not be completely identical (either morphologically, genotypically, or phenotypically) to the parent cell.

The term "transfection" as used herein refers to the introduction of foreign nucleic acid into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign nucleic acid, DNA or RNA, into the genome of the transfected cell. The term "stable transfectant" refers to a cell which has stably integrated foreign DNA into the genomic DNA.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The nucleic acid sequence thus codes for the amino acid sequence.

The terms "polypeptide", "peptide", and "protein" are used interchangeably herein to refer to polymers of amino acids of any length. The polymer may be linear, cyclic, or branched, it may comprise modified amino acids, and it may be interrupted by non-amino acids. The terms also encompass amino acid polymers that have been modified, for example, via sulfation, glycosylation, lipidation, acetylation, phosphorylation, iodination, methylation, oxidation, proteolytic processing, phosphorylation, prenylation, racemization, selenoylation, transfer-RNA mediated addition of amino acids to proteins such as arginylation, ubiquitination, or any other manipulation, such as conjugation with a labeling component. As used herein the term "amino acid" refers to either natural and/or unnatural or synthetic amino acids, including glycine and both the D or L optical isomers, and amino acid analogs and peptidomimetics. A polypeptide or amino acid sequence "derived from" a designated protein refers to the origin of the polypeptide. Preferably, the polypeptide has an amino acid sequence that is essentially identical to that of a polypeptide encoded in the sequence, or a portion thereof wherein the portion consists of at least 10-20 amino acids, or at least 20-30 amino acids, or at least 30-50 amino acids, or which is immunologically identifiable with a polypeptide encoded in the sequence. This terminology also includes a polypeptide expressed from a designated nucleic acid sequence.

The term "subject", as used herein, refers to any animal, e.g., a mammal or marsupial. Subjects of the present invention include but are not limited to humans, non-human primates (e.g., rhesus or other types of macaques), mice, pigs, horses, donkeys, cows, sheep, rats and fowl of any kind.

The term "recipient" and their grammatical equivalents as used herein can refer to a human or non-human animal in receipt of a therapy or treatment.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease.

"Treatment" as used herein covers any treatment of a disease in a mammal, e g mouse, rat, rabbit, pig, primate, including humans and other apes, particularly a human, and includes: (a) preventing the disease or symptom from occurring in a subject which may be predisposed to the disease or symptom but has not yet been diagnosed as having it; (b) inhibiting the disease symptom; (c) arresting development of the disease; (d) relieving the disease symptom; (e) causing regression of the disease or symptom; or any combination thereof.

The terms "cancer", "neoplasm", "tumor", and "carcinoma", are used interchangeably herein to refer to cells which exhibit relatively autonomous growth, so that they exhibit an aberrant growth phenotype characterized by a significant loss of control of cell proliferation. In general, cells of interest for detection or treatment in the present application include precancerous (e.g., benign), malignant, pre-metastatic, metastatic, and non-metastatic cells. The term "normal" as used in the context of "normal cell," is meant to refer to a cell of an untransformed phenotype or exhibiting a morphology of a non-transformed cell of the tissue type being examined. "Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.).

The term "peripheral blood lymphocytes" (PBL) and its grammatical equivalents as used herein can refer to lymphocytes that circulate in the blood (e.g., peripheral blood). Peripheral blood lymphocytes can refer to lymphocytes that are not localized to organs. Peripheral blood lymphocytes can comprise T cells, NK cells, B cell, or any combinations thereof.

The term "immunoresponsive cell" can refer to a cell that can elicit an immune response, including but not limited to T cells, B cells, and NKT cells, their respective precursor cells and progeny thereof. An immunoresponsive cell can also refer to a cell of a lymphoid or myeloid lineage.

The term "T cell" and its grammatical equivalents as used herein can refer to a T cell from any origin. For example, a T cell can be a primary T cell, e.g., an autologous T cell, a cell line, etc. The T cell can also be human or non-human.

The term "T cell activation" or "T cell triggering" and its grammatical equivalents as used herein can refer to the state of a T cell that has been sufficiently stimulated to induce detectable cellular proliferation, cytokine production and/or detectable effector function. In some cases, "full T cell activation" can be similar to triggering T cell cytotoxicity. T cell activation can be measured using various assays known in the art. Said assays can be an ELISA to measure cytokine secretion, an ELISPOT, flow cytometry assays to measure intracellular cytokine expression (CD107), flow cytometry assays to measure proliferation, and cytotoxicity assays (51Cr release assay) to determine target cell elimination. Said assays typically use controls (non-engineered cells) to compare to engineered cells (CAR T) to determine relative activation of an engineered cell compared to a control.

Additionally, said assays can compare engineered cells incubated or put in contact with a target cell not expressing the target antigen. For example, said comparison can be a CD19-CAR T cell incubated with a target cell that does not express CD19.

The term "sequence" and its grammatical equivalents when used to refer to a nucleotide sequence, can encompass DNA or RNA; and can be either single-stranded or double stranded. A nucleic acid sequence can be mutated. A nucleic acid sequence can be of any length, for example, between 2 and 1,000,000 or more nucleotides in length (or any integer value there between or there above), e.g., between about 100 and about 10,000 nucleotides or between about 200 and about 500 nucleotides.

As used herein, the term "isolated" means separated from constituents, cellular and otherwise, in which the polynucleotide, peptide, polypeptide, protein, antibody, or fragments thereof, are normally associated with in nature. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred. A substance can also be provided in an isolated state by a process of artificial assembly, such as by chemical synthesis or recombinant expression.

"Linked" and "fused" or "fusion" are used interchangeably herein. These terms refer to the joining together of two more chemical elements or components, by whatever means including chemical conjugation or recombinant means. An "in-frame fusion" refers to the joining of two or more open reading frames (ORFs) to form a continuous longer ORF, in a manner that maintains the correct reading frame of the original ORFs. Thus, the resulting recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence (e.g. "flexon").

"Recombinant" as applied to a polynucleotide means that the polynucleotide is the product of various combinations of cloning, restriction and/or ligation steps, and other procedures that result in a construct that is distinct from a polynucleotide found in nature.

The terms "gene" or "gene fragment" are used interchangeably herein. They refer to a polynucleotide containing at least one open reading frame that is capable of encoding a particular protein after being transcribed and translated. A gene or gene fragment may be genomic, cDNA, or synthesized, as long as the polynucleotide contains at least one open reading frame, which may cover the entire coding region or a segment thereof.

"Operably linked" or "operatively linked" refers to a juxtaposition wherein the components so described are in a relationship permitting them to function in their intended manner. For instance, a promoter sequence is operably linked to a coding sequence if the promoter sequence promotes transcription of the coding sequence.

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectively referred to as gene product. If the polynucleotide is derived from genomic DNA, expression may include splicing of the mRNA in a eukaryotic cell.

Compositions—Antigen Binding Units

In one embodiment, the present disclosure provides an antigen binding unit comprising a light chain CDR and a heavy chain CDR, wherein the antigen binding unit specifically binds to a WT1 peptide complexed with HLA, wherein the WT1 peptide has the amino acid sequence of SEQ ID NO: 1, and wherein the antigen binding unit exhibits no significant binding to a reference peptide complexed with HLA, wherein the reference peptide has the amino acid sequence of SEQ ID NO: 58 or SEQ ID NO: 59.

In another embodiment, the present disclosure provides an antigen binding unit comprising a light chain CDR and a heavy chain CDR, wherein the antigen binding unit specifically binds to a WT1 peptide complexed with HLA, wherein the WT1 peptide has the amino acid sequence of SEQ ID NO: 1, and wherein the antigen binding unit exhibits less non-specific binding to a reference peptide complexed with HLA as compared to that of a reference antigen binding unit having the amino acid sequence of SEQ ID NO: 60, wherein the reference peptide has the amino acid sequence of SEQ ID NO: 58 or SEQ ID NO: 59.

In yet another embodiment, the present disclosure provides an antigen binding unit comprising a light chain CDR and a heavy chain CDR, the light chain CDR comprises LCDR1, LCDR2, and LCDR3; and the heavy chain CDR comprises HCDR1, HCDR2, and HCDR3, wherein said LCDR1, LCDR2, and LCDR3 each comprises a sequence sharing at least 80% sequence homology to a sequence selected from the group consisting of SEQ ID NO: 5-7 and 11-15, and wherein said HCDR1, HCDR2, and HCDR3 each comprises a sequence having least 80% sequence homology to a sequence selected from the group consisting of SEQ ID NO: 2-4, 8-10, and 16-17.

In some aspects of any of the embodiments disclosed herein, an antigen binding unit comprises a light chain CDR. A light chain CDR can be a complementarity determining region of a light chain of an antigen binding unit. A light chain CDR can comprise a continuous sequence of amino acid residues, or two or more contiguous sequences of amino acid residues separated by, and optionally flanked by, non-complementarity determining regions, such as framework regions. In some examples, a light chain CDR comprises two or more light chain CDRs, which can be referred to as light chain CDR-1, CDR-2, and so on. In advantageous examples, a light chain CDR comprises three light chain CDRs, which can be referred to as light chain CDR-1, light chain CDR-2, and light chain CDR-3 respectively. In some examples, a group of CDRs present on a common light chain can collectively be referred to as light chain CDRs.

In some aspects of any of the embodiments disclosed herein, an antigen binding unit comprises a heavy chain CDR. A heavy chain CDR can be a complementarity determining region of a heavy chain of an antigen binding unit.

A heavy chain CDR can comprise a continuous sequence of amino acid residues, or two or more contiguous sequences of amino acid residues separated by, and optionally flanked by, non-complementarity determining regions, such as framework regions. In some examples, a heavy chain CDR comprises two or more heavy chain CDRs, which can be referred to as heavy chain CDR-1, CDR-2, and so on. In advantageous examples, a heavy chain CDR comprises three heavy chain CDRs, which can be referred to as heavy chain CDR-1, heavy chain CDR-2, and heavy chain CDR-3 respectively. In some examples, a group of CDRs present on a common heavy chain can collectively be referred to as heavy chain CDRs.

In some aspects of any of the embodiments disclosed herein, a subject antigen binding unit specifically binds to WT1 or a WT1 peptide. In some examples, the subject antigen binding unit specifical binds to a WT1 peptide complexed with HLA. WT1 as used herein can also refer to orthologues, homologues, codon-optimized forms, truncated forms, fragmented forms, mutated forms, or any other known derivative form of a known WT1 sequence. For example, WT1 can be human WT1, which is represented by GenBank accession number [P19544] and comprises the sequence of SEQ ID NO: 1. Additionally, WT1 can comprise a sequence sharing at least 50% identity to any one of SEQ ID NO: 1, SEQ ID NO: 58, and SEQ ID NO: 59. WT1 can comprise a sequence sharing at least 50%, 55%, 60%, 65%, 70%, 75%, 80%, 85%, 90%, 95%, 99%, or greater than 99% identity to any one of SEQ ID NO: 1, SEQ ID NO: 58, and SEQ ID NO: 59.

Binding specificity can be determined by complementarity determining regions, or CDRs, such as light chain CDRs or heavy chain CDRs. In many cases, binding specificity is determined by light chain CDRs and heavy chain CDRs. A given combination of heavy chain CDRs and light chain CDRs provides a given binding pocket that confers greater affinity and/or specificity towards WT1 or WT1 peptide complexed with HLA as compared to other reference antigens or reference peptides.

Binding of an antigen binding unit to a WT1 peptide complexed with HLA can be characterized or expressed by any method known in the art. For example, binding can be characterized by binding affinity, which can be the strength of the interaction between the antigen binding unit and the antigen. Binding affinity can be determined by any method known in the art, such as in vitro binding assays. For example, binding affinity of antigen binding units disclosed herein can be determined when assayed in an in vitro binding assay utilizing cells expressing WT1 and HLA. Binding affinity of a subject antigen binding unit can be expressed in terms of Kd, which is the equilibrium dissociation constant between an antibody and its respective antigen. In some cases, antigen binding units as disclosed herein specifically bind to a WT1 peptide complexed with HLA with a Kd within a range of about 10 µM to about 1 fM. For example, an antigen binding unit can specifically bind to CD47 with a Kd of less than about 10 µM, 1 µM, 0.1 µM, 10 nM, 1 nM, 0.1 nM, 10 pM, 1 pM, 0.1 pM, 10 fM, 1 fM, 0.1 fM, or less than 0.1 fM. In some examples, the Kd is less than 1.5 nM. In some examples, the Kd is less than 50 pM.

In some aspects, a subject antigen binding unit exhibits no significant binding to a reference peptide complexed with HLA. In some examples, the binding level of a subject antigen binding unit to a reference peptide complexed with HLA is no more than 10% of the binding level of said antigen binding unit to a WT1 peptide complexed with HLA. For example, the binding level can be 10%, 9%, 8%, 7%, 6%, 5%, 4%, 3%, 2%, 1%, or less than 1% of the binding level of said antigen binding unit to a WT1 peptide complexed with HLA. In some examples, the reference peptide has the amino acid sequence of SEQ ID NO: 58 or SEQ ID NO: 59.

In some aspects, a subject antigen binding unit exhibits less non-specific binding to a reference peptide complexed with HLA as compared to that of a reference antigen binding unit. In some examples, the subject antigen binding unit exhibits 5%, 10%, 15%, 20%, 25%, 30%, 35%, 40%, 45%, 50%, 55%, 60%, 65%, 70%, 75%, 80%, 85%, 90%, 95%, or 100% less non-specific binding to a reference peptide complexed with HLA as compared to that of a reference antigen binding unit. In some examples, the subject antigen binding unit exhibits 1 fold, 2 fold, 3 fold, 4 fold, 5 fold, 6 fold, 7 fold, 8 fold, 9 fold, 10 fold, or more than 10 fold less non-specific binding to a reference peptide complexed with HLA as compared to that of a reference antigen binding unit. In some examples, the reference antigen binding unit has the amino acid sequence of SEQ ID NO: 60. In some examples, the reference peptide has the amino acid sequence of SEQ ID NO: 58 or SEQ ID NO: 59.

In some aspects of any of the embodiments disclosed herein, a subject antigen binding unit comprises a light chain CDR and a heavy chain CDR. Subject antigen binding units can comprise any LCDR or HCDR listed in Table 1. Additionally or alternatively, a subject antigen binding unit can comprise a LCDR or a HCDR with at least 60% identity to any of the LCDR or HCDR listed in Table 1. In some aspects, a subject LCDR or HCDR can exhibit at least 65%, 70%, 75%, 80%, 85%, 90%, 95%, 99%, or greater sequence identity to any of the SEQ ID NOs listed in Table 1.

TABLE 1

| Antigen binding unit | $V_L$ | $V_H$ |
|---|---|---|
| ABU1 | SEQ ID NO: 26 | SEQ ID NO: 18 |
| ABU2 | SEQ ID NO: 28 | SEQ ID NO: 20 |
| ABU3 | SEQ ID NO: 30 | SEQ ID NO: 20 |
| ABU4 | SEQ ID NO: 28 | SEQ ID NO: 22 |
| ABU5 | SEQ ID NO: 28 | SEQ ID NO: 24 |

In some cases, the light chain (LC) CDR comprises light LCDR1, LCDR2, and LCDR3; and the heavy chain (HC) CDR comprises HCDR1, HCDR2, and HCDR3. In some examples, said LCDR1, LCDR2, and LCDR3 each have a sequence selected from the group consisting of SEQ ID NOs: 5-7 and 11-15. In some examples, said HCDR1, HCDR2, HCDR3 each have a sequence selected from the group consisting of SEQ ID NO: 2-4, 8-10, and 16-17. In some examples, said LCDR1, LCDR2, and LCDR3 each have a sequence selected from the group consisting of SEQ ID NO: 5-7 and 11-15 and said HCDR1, HCDR2, HCDR3 each have a sequence selected from the group consisting of SEQ ID NO: 2-4, 8-10, and 16-17.

In some aspects of any of the embodiments disclosed herein, an antigen binding unit comprises a light chain CDR wherein said light chain (LC) CDR comprises a combination of three LCDRs, namely LCDR1, LCDR2, and LCDR3. A combination of three LCDRs can comprise any combination listed in Table 2.

TABLE 2

| | Example LCDR | | |
|---|---|---|---|
| | LCDR1 | LCDR2 | LCDR3 |
| Example 1 | SEQ ID NO: 5 | SEQ ID NO: 6 | SEQ ID NO: 7 |
| Example 2 | SEQ ID NO: 11 | SEQ ID NO: 12 | SEQ ID NO: 13 |
| Example 3 | SEQ ID NO: 14 | SEQ ID NO: 15 | SEQ ID NO: 13 |

In some aspects of any of the embodiments disclosed herein, an antigen binding unit comprises a heavy chain CDR wherein said heavy chain (HC) CDR comprises a combination of three HCDRs, namely HCDR1, HCDR2, and HCDR3. A combination of three HCDRs can comprise any combination listed in Table 3.

TABLE 3

| Example HCDR | HCDR1 | HCDR2 | HCDR3 |
|---|---|---|---|
| Example 1 | SEQ ID NO: 2 | SEQ ID NO: 3 | SEQ ID NO: 4 |
| Example 2 | SEQ ID NO: 8 | SEQ ID NO: 9 | SEQ ID NO: 10 |
| Example 3 | SEQ ID NO: 8 | SEQ ID NO: 16 | SEQ ID NO: 10 |
| Example 4 | SEQ ID NO: 8 | SEQ ID NO: 17 | SEQ ID NO: 10 |

In some aspects of any of the embodiments disclosed herein, an antigen binding unit comprises a light chain CDR and a heavy chain CDR, wherein said light chain CDR and said heavy chain CDR comprise, respectively, the LCDR and the HCDR selected from the group consisting of any combination of LCDRs listed in Table 2 and any combination of HCDRs listed in Table 3.

In some aspects, a subject antigen binding unit is a monoclonal antigen binding unit, a polyclonal antigen binding unit, a humanized antigen binding unit, a chimeric antigen binding unit, a monovalent antigen binding unit, a multivalent antigen binding unit, a bispecific antigen binding unit, or any combination thereof. The antigen binding units can adopt a variety of formats, including but not limited to sFC, Fv, ccFv, Fab', F(ab')2, and Fd. Such antibody binding units can be generated from whole immunoglobulins by ricin, pepsin, papain, or other protease cleavage. Subject antigen binding units can also be comprised within a chimeric antigen receptor (CAR). In such examples, the antigen binding unit is often an extracellular antigen binding unit.

In addition, antigen binding units can be designed utilizing recombinant immunoglobulin techniques. For instance "Fv" immunoglobulins for use in the present invention may be produced by linking a variable light chain region to a variable heavy chain region via a peptide linker. For example, a peptide linker can be poly-glycine or another sequence which does not form an alpha helix or beta sheet motif. Fvs can also be made which comprise stabilizing disulfide bonds between the $V_H$ and $V_L$ regions, as described in U.S. Pat. No. 6,147,203, incorporated fully herein by reference. Any of these antigen binding unites can be utilized in the present invention. In some aspects, an antigen binding unit can be a whole immunoglobulin having two light chains paired with two heavy chains.

Antigen-binding units can be heteromultimers comprising a light-chain polypeptide and a heavy-chain polypeptide. Examples of an antigen binding unit include but are not limited to (i) a ccFv fragment stabilized by the heterodimerization sequences disclosed U.S. Pat. No. 6,833,441, incorporated herein in its entirety; (ii) any other monovalent and multivalent molecules comprising at least one ccFv fragment as described herein; (iii) a Fab fragment consisting of the VL, VH, CL and CH1 domains; (iv) an Fd fragment consisting of the VH and CH1 domains; (v) an Fv fragment consisting of the VL and VH domains of a single arm of an antibody; (vi) an F(ab')2 fragment, a bivalent fragment comprising two Fab fragments linked by a disulfide bridge at the hinge region; and (vii) a diabody.

Polyclonal antibodies can be raised by a standard protocol by injecting a production animal with an antigenic composition. See, e.g., Harlow and Lane, Antibodies: A Laboratory Manual, Cold Spring Harbor Laboratory, 1988. When utilizing an entire protein, or a larger section of the protein, antibodies may be raised by immunizing the production animal with the protein and a suitable adjuvant (e.g., Freund's, Freund's complete, oil-in-water emulsions, etc.). When a smaller peptide is utilized, it is advantageous to conjugate the peptide with a larger molecule to make an immunostimulatory conjugate. Commonly utilized conjugate proteins that are commercially available for such use include bovine serum albumin (BSA) and keyhole limpet hemocyanin (KLH). In order to raise antibodies to particular epitopes, peptides derived from the full sequence may be utilized. Alternatively, in order to generate antibodies to relatively short peptide portions of the protein target, a superior immune response may be elicited if the polypeptide is joined to a carrier protein, such as ovalbumin, BSA or KLH.

Polyclonal or monoclonal antigen binding units or antibodies can be produced from animals which have been genetically altered to produce human immunoglobulins. A transgenic animal can be produced by initially producing a "knock-out" animal which does not produce the animal's natural antibodies, and stably transforming the animal with a human antibody locus (e.g., by the use of a human artificial chromosome). In such cases, only human antibodies are then made by the animal. Techniques for generating such animals, and deriving antibodies therefrom, are described in U.S. Pat. Nos. 6,162,963 and 6,150,584, incorporated fully herein by reference. Such antibodies can be referred to as human xenogenic antibodies.

Alternatively, antigen binding units can be produced from phage libraries containing human variable regions. See U.S. Pat. No. 6,174,708, incorporated fully herein by reference.

In some aspects of any of the embodiments disclosed herein, an antigen binding unit is produced by a hybridoma. For example, an antigen binding unit disclosed herein can be produced by a hybridoma selected form the group consisting of hybridomas expressing one of the antigen binding units listed in Table 1.

For monoclonal antigen binding units or monoclonal antibodies, hybridomas may be formed by isolating the stimulated immune cells, such as those from the spleen of the inoculated animal. These cells can then be fused to immortalized cells, such as myeloma cells or transformed cells, which are capable of replicating indefinitely in cell culture, thereby producing an immortal, immunoglobulin-secreting cell line. The immortal cell line utilized can be selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT).

In addition, a subject antigen binding unit may be produced by genetic engineering. Humanized, chimeric, or xenogeneic human antigen binding units, which produce less of an immune response when administered to humans, are of use in the present invention.

Antigen binding units disclosed herein can have a reduced propensity to induce an undesired immune response in humans, for example, anaphylactic shock, and can also exhibit a reduced propensity for priming an immune response which would prevent repeated dosage with the antibody therapeutic or imaging agent (e.g., the human-anti-murine-antibody "HAMA" response). Such antigen binding units include, but are not limited to, humanized, chimeric, or xenogenic human antigen binding units.

By employing genetic engineering, an antigen binding unit may be modified in a variety of ways. In some cases, an antigen binding unit can be mutated, so that the antigen binding unit may be selected for higher affinity to its target (eg. a WT1 peptide complexed with HLA). In some cases, the affinity of the antigen binding unit for its target can be optimized for targets that can be expressed at low levels on normal tissues. This optimization can be performed to minimize potential toxicities. In other cases, the cloning of an antigen binding unit that has a higher affinity for the membrane bound form of a target can be preferable over its soluble form counterpart. This modification can be performed because some targets can also be detected in soluble form at different levels and their targeting can cause unintended toxicity.

In some cases, a subject antigen binding unit can be murine, humanized, or fully human. An antigen binding unit can be from about 1% to about 100% human. In some cases, an antigen binding unit can be from about 10%, 20%, 30%, 40%, 50%, 60%, 70%, 80%, 90%, or up to about 100% human.

Chimeric antigen binding units or chimeric antibodies can be made, for example, by recombinant means by combining the murine variable light and heavy chain regions (VK and VH), obtained from a murine (or other animal-derived) hybridoma clone, with the human constant light and heavy chain regions, in order to produce an antibody with predominantly human domains. The production of such chimeric antibodies is well known in the art, and may be achieved by standard means (as described, e.g., in U.S. Pat. No. 5,624,659, incorporated fully herein by reference).

The term "humanized" as applies to a non-human (e.g. rodent or primate) antibodies are hybrid immunoglobulins, immunoglobulin chains or fragments thereof which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, rabbit or primate having the desired specificity, affinity and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance and minimize immunogenicity when introduced into a human body. In some examples, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody may also comprise at least a portion of an immunoglobulin constant region (Fc), typically that of a human immunoglobulin.

Humanized antibodies can be engineered to contain human-like immunoglobulin domains, and incorporate only the complementarity-determining regions of the animal-derived antibody. This can be accomplished by carefully examining the sequence of the hyper-variable loops of the variable regions of a monoclonal antigen binding unit or monoclonal antibody, and fitting them to the structure of a human antigen binding unit or human antibody chains. See, e.g., U.S. Pat. No. 6,187,287, incorporated fully herein by reference.

Methods for humanizing non-human antibodies are well known in the art. "Humanized" antibodies are antibodies in which at least part of the sequence has been altered from its initial form to render it more like human immunoglobulins. In some versions, the heavy (H) chain and light (L) chain constant (C) regions are replaced with human sequence. This can be a fusion polypeptide comprising a variable (V) region and a heterologous immunoglobulin C region. In some versions, the complementarity determining regions (CDRs) comprise non-human antibody sequences, while the V framework regions have also been converted to human sequences. See, for example, EP 0329400. In some versions, V regions are humanized by designing consensus sequences of human and mouse V regions, and converting residues outside the CDRs that are different between the consensus sequences.

In principle, a framework sequence from a humanized antibody can serve as the template for CDR grafting; however, it has been demonstrated that straight CDR replacement into such a framework can lead to significant loss of binding affinity to the antigen. Glaser et al. (1992) *J. Immunol.* 149:2606; Tempest et al. (1992) *Biotechnology* 9:266; and Shalaby et al. (1992) *J. Exp. Med.* 17:217. The more homologous a human antibody (HuAb) is to the original murine antibody (muAb), the less likely that the human framework will introduce distortions into the murine CDRs that could reduce affinity. Based on a sequence homology search against an antibody sequence database, the HuAb IC4 provides good framework homology to muM4TS.22, although other highly homologous HuAbs would be suitable as well, especially kappa L chains from human subgroup I or H chains from human subgroup III. Kabat et al. (1987). Various computer programs such as ENCAD (Levitt et al. (1983) *J. Mol. Biol.* 168:595) are available to predict the ideal sequence for the V region. The invention thus encompasses HuAbs with different variable (V) regions. It is within the skill of one in the art to determine suitable V region sequences and to optimize these sequences. Methods for obtaining antibodies with reduced immunogenicity are also described in U.S. Pat. No. 5,270,202 and EP 699,755.

Humanized antibodies can be prepared by a process of analysis of the parental sequences and various conceptual humanized products using three dimensional models of the parental and humanized sequences. Three dimensional immunoglobulin models are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved.

A process for humanization of subject antigen binding units can be as follows. The best-fit germline acceptor heavy and light chain variable regions is selected based on homology, canonical structure and physical properties of the human antibody germlines for grafting. Computer modeling of mVH/VL versus grafted hVH/VL is performed and prototype humanized antibody sequence is generated. If modeling indicated a need for framework back-mutations, second variant with indicated FW changes is generated. DNA fragments encoding the selected germline frameworks and murine CDRs are synthesized. The synthesized DNA fragments are subcloned into IgG expression vectors and sequences are confirmed by DNA sequencing. The humanized antibodies are expressed in cells, such as 293F and the proteins are tested, for example in MDM phagocytosis assays and antigen binding assays. The humanized antigen binding units are compared with parental antigen binding units in antigen binding affinity, for example, by FACS on cells expressing the target antigen. If the affinity is greater than 2-fold lower than parental antigen binding unit, a second round of humanized variants can be generated and tested as described above.

As noted above, an antigen binding units can be either "monovalent" or "multivalent." Whereas the former has one binding site per antigen-binding unit, the latter contains multiple binding sites capable of binding to more than one antigen of the same or different kind. Depending on the number of binding sites, antigen binding units may be bivalent (having two antigen-binding sites), trivalent (having three antigen-binding sites), tetravalent (having four antigen-binding sites), and so on.

Multivalent antigen binding units can be further classified on the basis of their binding specificities. A "monospecific" antigen binding unit is a molecule capable of binding to one or more antigens of the same kind. A "multispecific" antigen binding unit is a molecule having binding specificities for at least two different antigens. While such molecules normally will only bind two distinct antigens (i.e. bispecific antigen binding units), antibodies with additional specificities such as trispecific antibodies are encompassed by this expression when used herein. This disclosure further provides multispecific antigen binding units. Multispecific antigen binding units are multivalent molecules capable of binding to at least two distinct antigens. Preferred multispecific antigen binding units are bispecific and trispecific molecules exhibiting binding specificities to two and three distinct antigens, respectively.

In some aspects of an embodiment disclosed herein, an antigen binding unit is a bispecific antigen binding unit, wherein the antigen binding unit specifically binds to a WT1 peptide complexed with HLA and a second antigen. In some examples, the second antigen is not WT1. In some examples, the second antigen is CD3. In some examples, the second antigen is PD1 or PD-L1. In some examples, the second antigen is other immune checkpoint molecules including CTLA-4, OX40, OX40L, 4-1BB (CD137), CD40, CD40L, ICOS, CD70, CD27, GITR, GITRL, TL1A, TNFRSF25, VISTA, TIM-3, LAG-3, TIGIT, CD112, CD112R, CD226, CD96, B7-H3, B7-H4, CD48, CD244, CD200R, CD200, HVEM, BTLA, CD160, LIGHT, HHLA2, TMIGD2, BTNL2, CD39, CD73, NKG2A, NKG2D, MICA/B, KIR2DL-1, KIR2DL-2, KIR2DL-3, and KIR3DL2. In some examples, the second antigen is EGFR. In some examples, the second antigen is CD19, CD20, CD22, CD33, CD44, CD52, CD79b, CD96, CD97, CD99, CD123, CD138, CD155, CD171, PTHR2, HAVCR2, or other known cancer cell marker. Additional examples of suitable second antigens include, though are not limited to, FcγRI, CD 15, p185 HER2, HER3, FcγRIII (CD16), CD3, malignant B-cell (1D10), p9'7, claudin18.2, OVCAR-3, glypican-3, mesothelin, L-D1 (colon carcinoma), Trop2, melanocyte stimulating hormone analog, ErbB2, CAMA1, MoV18, CAIX (carboxyanhydrase-IX), neural cell adhesion molecule (NCAM), folate binding protein (FBP), GD2, GD3, EpCAM, EGP-40, VEGFR2, MUC-1, MUC-16, STEAP1 (six-transmembrane epithelial antigen of the prostate), PSMA, PSCA (prostate stem cell antigen), GPC-3, LMP-1, DNAM-1 (DNAX accessory molecule-1), pan carcinoma associated antigen (AMOC-31), saporin, Id-1, CD7, CD38, CD30, CD44v7/8, CEA, ricin A chain, interferon-α (IFN-α), hybridoma idiotype, vinca alkaloid, alkaline phosphatase, fibrin, tissue plasminogen activator (tPA), urokinase-type plasminogen activator (uPA), low density lipoprotein (LDL), Fc receptor (e.g. FcγRI, FcγRII or FcγRIII), herpes simplex virus (HSV), T-cell receptor, influenza, FcγR, HIV, EOTUBE, DPTA, hapten, rabbit IgG, ferritin, horse radish peroxidase (HRP), hormone, somatostatin, substance P, FITC, and beta-galactosidase. Other suitable second antigens include, though are not limited to, a tumor cell antigen, a cytotoxic trigger molecule, a toxin a fibrinolytic agent, a cell surface receptor, infectious disease target, a vaccine adjuvants, a diagnostic agent, a detection molecule, and a reporter molecule.

Compositions—Chimeric Antigen Receptors

In one embodiment, the present disclosure provides a chimeric antigen receptor comprising an extracellular antigen binding unit, a transmembrane domain, and an intracellular domain, wherein the extracellular antigen binding unit specifically binds to a WT1 peptide complexed with HLA, wherein the WT1 peptide has the amino acid sequence of SEQ ID NO: 1, and wherein the extracellular antigen binding unit exhibits no significant binding to a reference peptide complexed with HLA, wherein the reference peptide has the amino acid sequence of SEQ ID NO: 58 or SEQ ID NO: 59

In one embodiment, the present disclosure provides a chimeric antigen receptor comprising an extracellular antigen binding unit, a transmembrane domain, and an intracellular domain, wherein the extracellular antigen binding unit specifically binds to a WT1 peptide complexed with HLA, wherein the WT1 peptide has the amino acid sequence of SEQ ID NO: 1, and wherein the extracellular antigen binding unit exhibits less non-specific binding to a reference peptide complexed with HLA as compared to that of a reference antigen binding unit having the amino acid sequence of SEQ ID NO: 60, wherein the reference peptide has the amino acid sequence of SEQ ID NO: 58 or SEQ ID NO: 59.

A subject anti-WT1 chimeric antigen receptor (CAR) typically comprises an extracellular antigen binding unit, a transmembrane domain, and an intracellular signaling region that controls immunoresponsive cell activation. In some cases, the anti-WT1 CAR further comprises a hinge or spacer. In some cases, the anti-WT1 CAR further comprises one or more co-stimulatory domains In one aspect of any of the embodiments disclosed here, a subject chimeric antigen receptor comprises any subject antigen binding unit disclosed herein. In some examples, a subject antigen binding unit comprises an extracellular antigen binding unit is a subject antigen binding unit or comprises a subject antigen binding unit.

A chimeric antigen receptor typically comprises an extracellular antigen binding unit. In one embodiment, the extracellular antigen binding unit can be fully human. In other cases, the extracellular antigen binding unit can be humanized. In other cases, the extracellular antigen binding unit can be murine or a chimeric in the extracellular antigen binding unit is composed of amino acid sequences derived from at least two different animal species. In some cases, the extracellular antigen binding unit can be non-human. A variety of antigen binding units can be designed to target a WT1 peptide complexed with HLA. Non-limiting examples include single-chain variable fragments (scFv's) derived from antibodies, fragment antigen binding unit (Fab) selected from libraries, single domain fragment, or nature ligands that engage their cognate receptor. An extracellular antigen binding unit can encompass a scFv, a Fab, or a nature ligand, as well as any of their derivatives. An extracellular antigen binding unit can refer to a molecule other than an intact antibody that can comprise a portion of an intact antibody and that can bind an antigen to which an intact antibody binds. Examples of antibody fragments can include but are not limited to Fv, Fab, Fab', Fab'-SH, F (ab') 2; diabodies; linear antibodies; single-chain antibody molecules (e.g. scFv); and multispecific antibodies formed from antibody fragments.

An extracellular antigen binding unit, for example the scFv, Fab, or natural ligand, can be a portion of a CAR that determines antigen specificity. An extracellular antigen binding unit can bind to any complementary target. An extracellular antigen binding unit can be derived from an antibody for which sequences of a variable region are known. An extracellular antigen binding unit can be derived from an antibody sequence obtained from an available mouse hybridoma. Alternatively, an extracellular antigen binding unit can be obtained from whole-exomic sequencing of a tumor cell or primary cell, such as a tumor infiltrating lymphocyte (TIL).

In some cases, binding specificity of an extracellular antigen binding unit can be determined by complementarity determining regions, or CDRs, such as light chain CDRs or heavy chain CDRs. In many cases, binding specificity can be determined by light chain CDRs and heavy chain CDRs. A given combination of heavy chain CDRs and light chain CDRs can provide a given binding pocket that can confer a greater affinity and/or specificity towards an antigen, such as a WT1 peptide complexed with HLA, as compared to other reference antigens or reference peptides complexed with HLA. For example, a CDR specific to a WT1 peptide complexed with HLA can be expressed in an extracellular binding region of a CAR such that the CAR targeting the WT1 peptide complexed with HLA can target the immunoresponsive cell to a tumor cell expressing WT1 peptide complexed with HLA.

In some aspects of any of the embodiments disclosed herein, an extracellular antigen binding unit, such as a scFv, can comprise a light chain CDR specific for a WT1 peptide complexed with HLA. A light chain CDR can be a complementarity determining region of a light chain of an antigen binding unit, such as a scFv of a CAR. A light chain CDR can comprise a continuous sequence of amino acid residues, or two or more contiguous sequences of amino acid residues separated by, and optionally flanked by, non-complementarity determining regions, such as framework regions. In some cases, a light chain CDR can comprise two or more light chain CDRs, which can be referred to as light chain CDR-1, CDR-2, and so on. In some cases, a light chain CDR can comprise three light chain CDRs, which can be referred to as light chain CDR-1, light chain CDR-2, and light chain CDR-3 respectively. In some examples, a group of CDRs present on a common light chain can collectively be referred to as light chain CDRs.

In some aspects of any of the embodiments disclosed herein, extracellular antigen binding unit, such as a scFv, can comprise a heavy chain CDR specific for a WT1 peptide complexed with HLA. A heavy chain CDR can be a complementarity determining region of a heavy chain of an antigen binding unit such as a scFv. A heavy chain CDR can comprise a continuous sequence of amino acid residues, or two or more contiguous sequences of amino acid residues separated by, and optionally flanked by, non-complementarity determining regions, such as framework regions. In some cases, a heavy chain CDR can comprise two or more heavy chain CDRs, which can be referred to as heavy chain CDR-1, CDR-2, and so on. In some cases, a heavy chain CDR can comprise three heavy chain CDRs, which can be referred to as heavy chain CDR-1, heavy chain CDR-2, and heavy chain CDR-3 respectively. In some cases, a group of CDRs present on a common heavy chain can collectively be referred to as heavy chain CDRs.

In some cases, an extracellular antigen binding unit specifically recognizes a WT1 peptide complexed with HLA. In some cases, extracellular antigen binding unit can target an N-terminal peptide, a C-terminal peptide, or any peptide of WT1. In some cases, the WT1 peptide has the amino acid sequence of SEQ ID NO:1.

In some cases, an extracellular antigen binding unit targeting a WT1 peptide complexed with HLA can be expressed by an anti-WT1 CAR immunoresponsive cell. In some cases, CDRs, light chain and/or heavy chain that bind a WT1 peptide complexed with HLA can be comprised within an extracellular antigen binding unit of a CAR immunoresponsive cell, such as CAR T cells. In some cases, modified anti-WT1 CDRs can be expressed on an extracellular antigen binding unit of a CAR immunoresponsive cell and have from about 50% homology to about 100% homology to original anti-WT1 CDRs. In some cases, a modified anti-WT1 CDR can comprise from about 50%, 55%, 60%, 65%, 70%, 75%, 80%, 85%, 90%, 91%, 92%, 93%, 94%, 95%, 96%, 97%, 98%, 99%, or up to about 100% homology to an unmodified anti-WT1 CDR.

By employing genetic engineering, an extracellular antigen binding unit may be modified in a variety of ways. In some cases, an extracellular antigen binding unit can be mutated, so that the extracellular antigen binding unit may be selected for higher affinity to its target. In some cases, the affinity of the extracellular antigen binding unit for its target can be optimized for targets that can be expressed at low levels on normal tissues. This optimization can be performed to minimize potential toxicities. In other cases, the cloning of an extracellular antigen binding unit that has a higher affinity for the membrane bound form of a target can be preferable over its soluble form counterpart. This modification can be performed because some targets can also be detected in soluble form at different levels and their targeting can cause unintended toxicity.

In some cases, extracellular antigen binding unit can be murine, humanized, or fully human. An extracellular antigen binding unit can be from about 1% to about 100% human. In some cases, a extracellular antigen binding unit can be from about 10%, 20%, 30%, 40%, 50%, 60%, 70%, 80%, 90%, or up to about 100% human.

In some examples, a subject chimeric antigen receptor can comprise an extracellular antigen binding unit which comprises a light chain (LC) CDR and a heavy chain (HC) CDR.

In some cases, a subject extracellular antigen binding unit can comprise any LCDR or HCDR listed in Table 1. Additionally or alternatively, the extracellular antigen binding unit can comprise a LCDR or a HCDR with at least 60% identity to any of the LCDR or HCDR listed in Table 1. In some aspects, a subject LCDR or HCDR can exhibit at least 65%, 70%, 75%, 80%, 85%, 90%, 95%, 99%, or greater sequence identity to any of the SEQ ID NOs listed in Table 1.

In some cases, the light chain (LC) CDR comprises LCDR1, LCDR2, and LCDR3; and the heavy chain (HC) CDR comprises HCDR1, HCDR2, and HCDR3. In some examples, said LCDR1, LCDR2, and LCDR3 each have a sequence selected from the group consisting of SEQ ID NOs: 5-7 and 11-15. In some examples, said HCDR1, HCDR2, HCDR3 each have a sequence selected from the group consisting of SEQ ID NO: 2-4, 8-10, and 16-17. In some examples, said LCDR1, LCDR2, and LCDR3 each have a sequence selected from the group consisting of SEQ ID NO: 5-7 and 11-15 and said HCDR1, HCDR2, HCDR3 each have a sequence selected from the group consisting of SEQ ID NO: 2-4, 8-10, and 16-17.

In some aspects of any of the embodiments disclosed herein, an extracellular antigen binding unit comprises a light chain CDR wherein said light chain (LC) CDR comprises a combination of three LCDRs, namely LCDR1, LCDR2, and LCDR3. A combination of three LCDRs can comprise any combination listed in Table 2.

In some aspects of any of the embodiments disclosed herein, an extracellular antigen binding unit comprises a heavy chain CDR wherein said heavy chain (HC) CDR comprises a combination of three HCDRs, namely HCDR1, HCDR2, and HCDR3. A combination of three HCDRs can comprise any combination listed in Table 3.

In some aspects of any of the embodiments disclosed herein, an extracellular antigen binding unit comprises a light chain CDR and a heavy chain CDR, wherein said light chain CDR and said heavy chain CDR comprise, respectively, the LCDR and the HCDR selected from the group consisting of any combination of LCDRs listed in Table 2 and any combination of HCDRs listed in Table 3.

In some cases, an extracellular antigen binding unit comprises a hinge or spacer. The terms hinge and spacer can be used interchangeably. A hinge can be considered a portion of a CAR used to provide flexibility to an extracellular antigen binding unit. In some cases, a hinge can be used to detect a CAR on the cell surface of a cell, particularly when antibodies to detect the extracellular antigen binding unit are not functional or available. For instance the length of the hinge derived from an immunoglobulin may require optimization depending on the location of the epitope on the target that the extracellular antigen binding unit is targeting.

In some cases, a hinge may not belong to an immunoglobulin but instead to another molecule such the native hinge of a CD8 alpha molecule. A CD8 alpha hinge can contain cysteine and proline residues known to play a role in the interaction of a CD8 co-receptor and MHC molecule. Said cysteine and proline residues can influence the performance of said CAR. In some examples, a CD8 alpha hinge comprises the amino acid sequence of SEQ ID NO: 35.

A CAR hinge can be size tunable and can compensate to some extent in normalizing the orthogonal synapse distance between CAR immunoresponsive cell and a target cell. This topography of the immunological synapse between an immunoresponsive cell and a target cell also defines a distance that cannot be functionally bridged by a CAR due to a membrane-distal epitope on a cell-surface target molecule that, even with a short hinge CAR, cannot bring the synapse distance in to an approximation for signaling. Likewise, membrane-proximal CAR target antigen epitopes have been described for which signaling outputs are only observed in the context of a long hinge CAR. A hinge can be tuned according to the extracellular antigen binding unit that is used. A hinge can be of any length.

A transmembrane domain can anchor a CAR to the plasma membrane of a cell. A native transmembrane portion of CD28 can be used in a CAR. In other cases, a native transmembrane portion of CD8 alpha can also be used in the CAR. By "CD8" it can be meant a protein having at least 85, 90, 95, 96, 97, 98, 99 or 100% identity to NCBI Reference No: NP_001759 or a fragment thereof that has stimulatory activity. By "CD8 nucleic acid molecule" it can be meant a polynucleotide encoding a CD8 polypeptide. In some cases, a transmembrane region can be a native transmembrane portion of CD28. By "CD28" it can be meant a protein having at least 85, 90, 95, 96, 97, 98, 99 or 100% identity to NCBI Reference No: NP_006130 or a fragment thereof that has stimulatory activity. By "CD28 nucleic acid molecule" can be meant a polynucleotide encoding a CD28 polypeptide. In some cases, the transmembrane portion can comprise CD8α region.

An intracellular signaling region of a CAR can be responsible for activation of at least one of an effector function of the immunoresponsive cell in which the CAR has been placed in. A CAR can induce the effector function of a T cell, for example, which may be cytolytic activity or helper activity including the secretion of cytokines. Thus the term intracellular signaling region refers to the portion of a protein which transduces the effector function signal and directs the cell to perform a specialized function. While usually the entire intracellular signaling region can be employed, in many cases it is not necessary to use the entire chain of a signaling domain. In some cases, a truncated portion of the intracellular signaling region is used. In some cases, the term intracellular signaling region is thus meant to include any truncated portion of the intracellular signaling region sufficient to transduce the effector function signal.

Preferred examples of signaling domains for use in a CAR can include a cytoplasmic sequence of the T cell receptor (TCR) and co-receptors that act in concert to initiate signal transduction following target-receptor engagement, as well as any derivative or variant of these sequences and any synthetic sequence that has the same functional capability.

In some cases, said intracellular signaling region may contain signaling motifs which are known as immunoreceptor tyrosine-based activation motifs (ITAMs). Examples of ITAM containing cytoplasmic signaling sequences include those derived from TCR zeta, FcR gamma, FcR beta, CD3 gamma, CD3 delta, CD3 epsilon, CD5, CD22, CD79a, CD79b, and CD66d. However, in preferred embodiments, the intracellular signaling domain is derived from CD3 zeta chain.

An example of a T cell signaling domain containing one or more ITAM motifs is the CD3 zeta domain, also known as T cell receptor T3 zeta chain or CD247. This domain is part of the T cell receptor-CD3 complex and plays an important role in coupling antigen recognition to several intracellular signal-transduction pathways with primary effector activation of the T cell. As used herein, CD3 zeta is primarily directed to human CD3 zeta and its isoforms as known from Swissprot entry P20963, including proteins having a substantially identical sequence. As part of the chimeric antigen receptor, again the full T cell receptor T3 zeta chain is not required and any derivatives thereof comprising the signaling domain of T cell receptor T3 zeta chain are suitable, including any functional equivalents thereof.

An intracellular signaling domain can be selected from any one of the domains of Table 4. In some cases, a domain may be modified so that homology to any one of the referenced domains may from about 50% to about 100%. Any one of the domains of Table 4 may be modified such that a modified version may comprise from about 50, 60, 70, 80, 90, 95, 96, 97, 98, 99, or up to about 100% homology.

An intracellular signaling region of a CAR can further comprise one or more costimulatory domains. An intracellular signaling region can comprise a single co-stimulatory domain, for example a zeta-chain ($1^{st}$ generation CAR), or CD28 or 4-1BB ($2^{nd}$ generation CAR). In other examples, an intracellular signaling region can comprise two co-stimulatory domains, such as CD28/OX40 or CD28/4-1BB ($3^{rd}$ generation).

Together with intracellular signaling domains such as CD8, these co-stimulatory domains can produce downstream activation of kinase pathways, which support gene transcription and functional cellular responses. Co-stimulatory domains of CARs can activate proximal signaling proteins related to either CD28 (Phosphatidylinositol-4, 5-bisphosphate 3-kinase) or 4-1BB/OX40 (TNF-receptor-associated-factor adapter proteins) pathways, and MAPK and Akt activation.

In some cases, signals generated through the CAR can be complexed with secondary or co-stimulatory signals. With respect to the co-stimulatory signaling domain, the chimeric antigen receptor like complex can be designed to comprise several possible co-stimulatory signaling domains. As is well known in the art, in naïve T cells the mere engagement of the T cell receptor is not sufficient to induce full activation of T cells into cytotoxic T cells. Full, productive T cell activation requires a second co-stimulatory signal. Several receptors that have been reported to provide co-stimulation for T-cell activation, include, but are not limited to CD28, OX40, CD27, CD2, CD5, ICAM-1, LFA-1 (CD11a/CD18), 4-1BBL, MyD88 and 4-1BB. The signaling pathways utilized by these co-stimulatory molecules share the common property of acting in synergy with the primary T cell receptor activation signal. These co-stimulatory signaling regions provide a signal that can be synergistic with the primary effector activation signal originating from one or more ITAM motifs, for example a CD3 zeta signaling domain, and can complete the requirements for activation of the T cell.

In some cases, addition of co-stimulatory domains to a chimeric antigen receptor-like complex can enhance efficacy and durability of engineered cells. In another embodiment the T cell signaling domain and the co-stimulatory domain are fused to one another thereby composing the signaling region.

TABLE 4

Co-stimulatory domains

| Gene Symbol | Abbreviation | Name |
|---|---|---|
| CD27 | CD27; T14; S152; Tp55; TNFRSF7; S152. LPFS2 | CD27 molecule |
| CD28 | Tp44; CD28; CD28 antigen | CD28 molecule |
| TNFRSF9 | ILA; 4-1BB; CD137; CDwl37 | tumor necrosis factor receptor superfamily, member 9 |
| TNFRSF4 | OX40; ACT35; CD134; IMD16; TXGP1L | tumor necrosis factor receptor superfamily, member 4 |
| TNFRSF8 | CD30; Ki-1; D1S166E | tumor necrosis factor receptor superfamily, member 8 |
| CD40LG | IGM; IMD3; TRAP; gp39; CD154; CD40L; HIGM1; T-BAM; TNFSF5; hCD40L | CD40 ligand |
| ICOS | AILIM; CD278; CVID1 | inducible T-cell co-stimulator |
| ITGB2 | LAD; CD18; MF17; MFI7; LCAMB; LFA-1; MAC-1 | integrin, beta 2 (complement component 3 receptor 3 and 4 subunit) |
| CD2 | T11; SRBC; LFA-2 | CD2 molecule |
| CD7 | GP40; TP41; Tp40; LEU-9 | CD7 molecule |
| KLRC2 | NKG2C; CD159c; NKG2-C | killer cell lectin-like receptor subfamily C, member 2 |
| TNFRSF18 | AITR; GITR; CD357; GITR-D | tumor necrosis factor receptor superfamily, member 18 |
| TNFRSF14 | TR2; ATAR; HVEA; HVEM; CD270; LIGHTR | tumor necrosis factor receptor superfamily, member 14 |
| HAVCR1 | TIM; KIM1; TIM1; CD365; HAVCR; KIM-1; TIM-1; TIMD1; TIMD-1; HAVCR-1 | hepatitis A virus cellular receptor 1 |
| LGALS9 | HUAT; LGALS9A, Galectin-9 | lectin, galactoside-binding, soluble, 9 |
| CD83 | BL11; HB15 | CD83 molecule |

In some cases, a subject CAR can comprise a sequence or portion thereof exhibiting from about 50% to about 100% sequence identity to any one of SEQ ID NO: 46, SEQ ID NO: 61, SEQ ID NO: 62 and SEQ ID NO: 66. In some cases, a subject CAR can comprise a sequence exhibiting about 50%, 60%, 70%, 80%, 90%, 91%, 92%, 93%, 94%, 95%, 96%, 97%, 98%, 99%, or up to about 100% sequence identity to any one of SEQ ID NO: 46, SEQ ID NO: 61 to SEQ ID NO: 62 and SEQ ID NO: 66.

In some cases, a subject CAR can comprise a sequence having from about 50% to about 100% sequence identity to any one of SEQ ID NO: 67 to SEQ ID NO: 75 (Table 5). In some cases, a subject CAR can comprise a sequence exhibiting about 50%, 60%, 70%, 80%, 90%, 91%, 92%, 93%, 94%, 95%, 96%, 97%, 98%, 99%, or up to about 100% sequence identity to any one of SEQ ID NO: 67 to SEQ ID NO: 75.

TABLE 5

Exemplary Anti-WT1 CARs

| SEQ ID NO: | Construct |
|---|---|
| 67 | ABU3-28Z |
| 68 | ABU3-BBZ |
| 69 | ABU3-28BBZ |
| 70 | ABU2-28Z |
| 71 | ABU2-BBZ |
| 72 | ABU2-28BBZ |
| 73 | ABU4-28Z |
| 74 | ABU4-BBZ |
| 75 | ABU4-28BBZ |

Polynucleotides and Vectors of the Present Invention

In some embodiments, the present disclosure provides isolated nucleic acids encoding any of the antigen binding units or chimeric antigen receptors disclosed herein. In another embodiment, the present disclosure provides vectors comprising a nucleic acid sequence encoding any antigen binding unit or chimeric antigen receptor disclosed herein. In some embodiments, this invention provides isolated nucleic acids that encode a light-chain CDR and a heavy-chain CDR of an antigen binding unit or extracellular antigen binding unit disclosed herein.

The subject antigen binding units or chimeric antigen receptors can be prepared by recombinant DNA technology, synthetic chemistry techniques, or a combination thereof. For instance, sequences encoding the desired components of the antigen binding unit or chimeric antigen receptor, including light chain CDRs and heavy chain CDRs are typically assembled cloned into an expression vector using standard molecular techniques know in the art. These sequences may be assembled from other vectors encoding the desired protein sequence, from PCR-generated fragments using respective template nucleic acids, or by assembly of synthetic oligonucleotides encoding the desired sequences. Expression systems can be created by transfecting a suitable cell with an expressing vector comprising the antigen binding unit of interest.

Nucleotide sequences corresponding to various regions of light or heavy chains of an existing antibody can be readily obtained and sequenced using convention techniques including but not limited to hybridization, PCR, and DNA sequencing. Hybridoma cells that produce monoclonal antibodies serve as a preferred source of antibody nucleotide sequences. A vast number of hybridoma cells producing an array of monoclonal antibodies may be obtained from public or private repositories. The largest depository agent is American Type Culture Collection (atcc.org), which offers a diverse collection of well-characterized hybridoma cell lines. Alternatively, antibody nucleotides can be obtained from immunized or non-immunized rodents or humans, and form organs such as spleen and peripheral blood lymphocytes. Specific techniques applicable for extracting and synthesizing antibody nucleotides are described in Orlandi et al. (1989) *Proc. Natl. Acad. Sci. U.S.A.* 86: 3833-3837; Larrick et al. (1989) *Biochem. Biophys. Res. Commun.* 160:1250-1255; Sastry et al. (1989) *Proc. Natl. Acad. Sci., U.S.A.* 86: 5728-5732; and U.S. Pat. No. 5,969,108.

Polynucleotides encoding antigen binding units or chimeric antigen receptors can also be modified, for example, by substituting the coding sequence for human heavy and light chain constant regions in place of the homologous non-human sequences. In that manner, chimeric antibodies are prepared that retain the binding specificity of the original antigen binding unit.

It is also understood that the polynucleotides embodied in the invention include those coding for functional equivalents and fragments thereof of the exemplified polypeptides. Functionally equivalent polypeptides include those that enhance, decrease or not significantly affect properties of the polypeptides encoded thereby. Functional equivalents may be polypeptides having conservative amino acid substitutions, analogs including fusions, and mutants.

Due to the degeneracy of the genetic code, there can be considerable variation in nucleotides of an antigen binding unit coding sequence, as well as sequences suitable for construction of the polynucleotide and vectors of the present invention. Sequence variants may have modified DNA or amino acid sequences, one or more substitutions, deletions, or additions, the net effect of which is to retain the desired antigen-binding activity. For instance, various substitutions can be made in the coding region that either do not alter the amino acids encoded or result in conservative changes. These substitutions are encompassed by the present invention. Conservative amino acid substitutions include substitutions within the following groups: glycine, alanine; valine, isoleucine, leucine; aspatic acid, glutamic acid; asparagine, glutamine; serine, threonine; lysine, arginine; and phenylalanine, tyrosine. While conservative substitutions do effectively change one or more amino acid residues contained in the polypeptide to be produced, the substitutions are not expected to interfere with the antigen-binding activity of the resulting antigen binding units to be produced. Nucleotide substitutions that do not alter the amino acid residues encoded are useful for optimizing gene expression in different systems. Suitable substitutions are known to those of skill in the art and are made, for instance, to reflect preferred codon usage in the expression systems. Exemplary conservation substitutions are illustrated in the table below.

TABLE 6

| Original AA | Typical Cons. Subst. | Preferred Cons. Subst. |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Where desired, the recombinant polynucleotides of the present disclosure may comprise heterologous sequences that facilitate detection of the expression and purification of the gene product. Examples of such sequences are known in the art and include those encoding reporter proteins such as β-galactosidase, β-lactamase, chloramphenicol acetyltransferase (CAT), luciferase, green fluorescent protein (GFP) and their derivatives. Other heterologous sequences that facilitate purification may code for epitopes such as Myc, HA (derived from influenza virus hemagglutinin), His-6, FLAG, or the Fc portion of immunoglobulin, glutathione S-transferase (GST), and maltose-binding protein (MBP).

Polynucleotides disclosed herein can be conjugated to a variety of chemically functional moieties described above. Commonly employed moieties include labels capable of producing a detectable signal, signal peptides, agents that enhance immunologic reactivity, agents that facilitate coupling to a solid support, vaccine carriers, bioresponse modifiers, paramagnetic labels and drugs. The moieties can be covalently linked polynucleotide recombinantly or by other means known in the art.

Polynucleotides of the invention can comprise additional sequences, such as additional encoding sequences within the same transcription unit, controlling elements such as promoters, ribosome binding sites, and polyadenylation sites, additional transcription units under control of the same or a different promoter, sequences that permit cloning, expression, and transformation of a host cell, and any such construct as may be desirable to provide embodiments of this invention.

Polynucleotides embodied in this invention can be obtained using chemical synthesis, recombinant cloning methods, PCR, or any combination thereof. Methods of chemical polynucleotide synthesis are well known in the art and need not be described in detail herein. One of skill in the art can use the sequence data provided herein to obtain a desired polynucleotide by employing a DNA synthesizer or ordering from a commercial service.

Polynucleotides comprising a desired sequence can be inserted into a suitable vector which in turn can be introduced into a suitable host cell for replication and amplification. Accordingly, the invention encompasses a variety of vectors comprising one or more of the polynucleotides of the present invention. Also provided are selectable libraries of expression vectors comprising at least one vector encoding an antigen binding units disclosed herein.

Vectors of the present invention generally comprises a transcriptional or translational control sequences required for expressing the antigen binding units. Suitable transcription or translational control sequences include but are not limited to replication origin, promoter, enhancer, repressor binding regions, transcription initiation sites, ribosome binding sites, translation initiation sites, and termination sites for transcription and translation.

The choice of promoters will largely depend on the host cells in which the vector is introduced. It is also possible, to utilize promoters normally associated with a desired light or heavy chain gene, provided that such control sequences are compatible with the host cell system. Cell-specific or tissue-specific promoters may also be used. A vast diversity of tissue specific promoters have been described and employed by artisans in the field. Exemplary promoters operative in selective animal cells include hepatocyte-specific promoters and cardiac muscle specific promoters. Depending on the choice of the recipient cell types, those skilled in the art will know of other suitable cell-specific or tissue-specific promoters applicable for the construction of the expression vectors of the present invention.

Using known molecular cloning or gene engineering techniques, appropriate transcriptional control sequences, enhancers, terminators, or any other genetic element known in the art can integrated in operative relationship, optionally additionally with intact selectable fusion genes to be expressed in accordance with the present invention. In addition to the above-described elements, the vectors may contain a selectable marker (for example, a gene encoding a protein necessary for the survival or growth of a host cell transformed with the vector), although such a marker gene can be carried on another polynucleotide sequence co-introduced into the host cell.

The polynucleotides and vectors of this invention have several specific uses. They are useful, for example, in expression systems for the production of antigen binding units or chimeric antigen receptors. Such polynucleotides are useful as primers to effect amplification of desired polynucleotides. Furthermore, polynucleotides of this invention are also useful in pharmaceutical compositions including vaccines, diagnostics, and drugs.

The host cells of this invention can be used, inter alia, as repositories of the subject polynucleotides, vectors, or as vehicles for producing and screening desired antigen binding units or chimeric antigen receptors based on their antigen binding specificities.

Accordingly, the invention provides a method of identifying an antigen binding unit or chimeric antigen receptor that is immunoreactive with a desired antigen. Such a method can involve the following steps: (a) preparing a genetically diverse library of antigen binding units, wherein the library comprises at least one subject antigen binding unit; (b) contacting the library of antigen binding units with the desired antigen; (c) detecting a specific binding between antigen binding units and the antigen, thereby identifying the antigen binding unit that is immunoreactive with the desired antigen.

The ability of an antigen binding unit or chimeric antigen receptor to specifically bind to a desired antigen can be tested by a variety of procedures well established in the art. See Harlow and Lane (1988) Antibodies: A Laboratory Manual, Cold Spring Harbor Laboratory, New York; Gherardi et al. (1990) *J. Immunol. Meth.* 126:61-68. Typically, antigen binding units exhibiting desired binding specificities can be detected directly by immunoassays, for example, by reacting labeled antigen binding units with the antigens that are immobilized on a solid support or substrate. In general, the substrate to which the antigen is adhered is fabricated with material exhibiting a low level of non-specific binding during immunoassay. An example solid support is made from one or more of the following types of materials: plastic polymers, glass, cellulose, nitrocellulose, semi-conducting material, and metal. In some examples, the substrate is petri dish, chromatography beads, magnetic beads, and the like.

For such solid-phase assays, the unreacted antigen binding units are removed by washing. In a liquid-phase assay, however, the unreacted antigen binding units are removed by some other separation technique, such as filtration or chromatography. After binding the antigen to the labeled antigen binding units, the amount of bound label is determined. A variation of this technique is a competitive assay, in which the antigen is bound to saturation with an original binding molecule. When a population of the subject antigen binding unit is introduced to the complex, only those that exhibit higher binding affinity will be able to compete, and thus remain bound to the antigen.

Alternatively, specific binding to a given antigen can be assessed by cell sorting, which involves presenting the desired antigen on the cells to be sorted, then labeling the target cells with antigen binding units that are coupled to detectable agents, followed by separating the labeled cells from the unlabeled ones in a cell sorter. A sophisticated cell separation method is fluorescence-activated cell sorting (FACS). Cells traveling in single file in a fine stream are passed through a laser beam, and the fluorescence of each cell bound by the fluorescently labeled antigen binding unit is then measured.

Subsequent analysis of the eluted antigen binding units may involve protein sequencing for delineating the amino acid sequences of the light chains and heavy chains. Based on the deduced amino acid sequences, the cDNA encoding the antibody polypeptides can then be obtained by recombinant cloning methods including PCR, library screening, homology searches in existing nucleic acid databases, or any combination thereof. Commonly employed databases include but are not limited to GenBank, EMBL, DDBJ, PDB, SWISS-PROT, EST, STS, GSS, and HTGS.

When a library of antigen binding units is displayed on phage or bacterial particles, selection is preferably performed using affinity chromatography. The method typically proceeds with binding a library of phage antigen binding units to an antigen coated plates, column matrices, cells or to biotinylated antigen in solution followed by capture. The phages or bacteria bound to the solid phase are washed and then eluted by soluble hapten, acid or alkali. Alternatively, increasing concentrations of antigen can be used to dissociate the antigen binding units from the affinity matrix. For certain antigen binding units with extremely high affinity or avidity to the antigen, efficient elution may require high pH or mild reducing solution as described in WO 92/01047.

The efficiency of selection is likely to depend on a combination of several factors, including the kinetics of dissociation during washing, and whether multiple antigen binding units on a single phage or bacterium can simultaneously bind to antigens on a solid support. For example, antibodies with fast dissociation kinetics (and weak binding affinities) can be retained by use of short washes, multivalent display and a high coating density of antigen at the solid support. Conversely, the selection of antigen binding units with slow dissociation kinetics (and good binding affinities) can be favored by use of long washes, monovalent phages, and a low coating density of antigen.

Where desired, the library of antigen binding units can be pre-selected against an unrelated antigen to counter-select the undesired antigen binding units. The library may also be pre-selected against a related antigen in order to isolate, for example, anti-idiotypic antigen binding units.

Host Cells of the Present Invention

In some embodiments, the present disclosure provides host cells expressing any one of the antigen binding units disclosed herein. A subject host cell typically comprises a nucleic acid encoding any one of the antigen binding units disclosed herein.

The invention provides host cells transfected with the polynucleotides, vectors, or a library of the vectors described above. The vectors can be introduced into a suitable prokaryotic or eukaryotic cell by any of a number of appropriate means, including electroporation, microprojectile bombardment; lipofection, infection (where the vector is coupled to an infectious agent), transfection employing calcium chloride, rubidium chloride, calcium phosphate, DEAE-dextran, or other substances. The choice of the means for introducing vectors will often depend on features of the host cell.

For most animal cells, any of the above-mentioned methods is suitable for vector delivery. Preferred animal cells are vertebrate cells, preferably mammalian cells, capable of expressing exogenously introduced gene products in large quantity, e.g. at the milligram level. Non-limiting examples of preferred cells are NIH3T3 cells, COS, HeLa, and CHO cells.

Once introduced into a suitable host cell, expression of the antigen binding units can be determined using any nucleic acid or protein assay known in the art. For example, the presence of transcribed mRNA of light chain CDRs or heavy chain CDRs, or the antigen binding unit can be detected and/or quantified by conventional hybridization assays (e.g. Northern blot analysis), amplification procedures (e.g. RT-PCR), SAGE (U.S. Pat. No. 5,695,937), and array-based technologies (see e.g. U.S. Pat. Nos. 5,405,783, 5,412,087 and 5,445,934), using probes complementary to any region of antigen binding unit polynucleotide.

Expression of the vector can also be determined by examining the antigen binding unit expressed. A variety of techniques are available in the art for protein analysis. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunofluorescent assays, and SDS-PAGE.

Preparation of Antigen-Binding Units

In some embodiments, the present disclosure provides methods of producing any antigen binding unit or chimeric antigen receptor disclosed herein, wherein the method comprises culturing host cells expressing the antigen binding unit or chimeric antigen receptor under conditions suitable for expressing the antigen binding unit or chimeric antigen receptor, and isolating the antigen binding unit or chimeric antigen receptor expressed by the host cell.

The expressed antigen binding units or chimeric antigen receptors can be isolated using a variety of protein purification techniques known in the art. Generally, the antigen binding unit is isolated from culture media as secreted polypeptides, although they can be recovered from host cell lysates or bacterial periplasm, when directly produced without signal peptides. If the antigen binding units are membrane-bound, they can be solubilized by suitable detergent solutions commonly employed by artisans in the field. The recovered antigen binding units may be further purified by salt precipitation (e.g., with ammonium sulfate), ion exchange chromatography (e.g. on a cationic or anionic exchange column run at neutral pH and eluted with step gradients of increasing ionic strength), gel filtration chromatography (including gel filtration HPLC), and chromatography on tag-affinity column, or on affinity resins such as protein A, protein G, hydroxyapatite, and anti-immunoglobulin.

In addition, derivatized immunoglobulins with added chemical linkers, detectable moieties such as fluorescent dyes, enzymes, substrates, chemiluminescent moieties, specific binding moieties such as streptavidin, avidin, or biotin, or drug conjugates can be utilized in the methods and compositions of the present invention.

Additionally disclosed herein are antigen binding units or chimeric antigen receptors conjugated to a chemically functional moiety. Typically, the moiety is a label capable of producing a detectable signal. These conjugated antigen binding units or chimeric antigen receptors are useful, for example, in detection systems such as quantitation of tumor burden, and imaging of metastatic foci and tumor imaging. Such labels are known in the art and include, but are not limited to, radioisotopes, enzymes, fluorescent compounds, chemiluminescent compounds, bioluminescent compounds substrate cofactors and inhibitors. See, for examples of patents teaching the use of such labels, U.S. Pat. Nos. 3,817,837; 3,850,752; 3,939,350; 3,996,345; 4,277,437; 4,275,149; and 4,366,241. The moieties can be covalently linked to antigen binding units, recombinantly linked, or conjugated to antigen binding units through a secondary reagent, such as a second antibody, protein A, or a biotin-avidin complex.

Other functional moieties include signal peptides, agents that enhance immunologic reactivity, agents that facilitate coupling to a solid support, vaccine carriers, bioresponse modifiers, paramagnetic labels and drugs. Signal peptides is a short amino acid sequence that directs a newly synthesized protein through a cellular membrane, usually the endoplasmic reticulum in eukaryotic cells, and either the inner membrane or both inner and outer membranes of bacteria. Signal peptides can be at the N-terminal portion of a polypeptide or the C-terminal portion of a polypeptide, and can be removed enzymatically between biosynthesis and secretion of the polypeptide from the cell. Such a peptide can be incorporated into an antigen binding units to allow secretion of the synthesized molecules.

Agents that enhance immunologic reactivity include, but are not limited to, bacterial superantigens. Agents that facilitate coupling to a solid support include, but are not limited to, biotin or avidin. Immunogen carriers include, but are not limited to, any physiologically acceptable buffers. Bioresponse modifiers include cytokines, particularly tumor necrosis factor (TNF), interleukin-2, interleukin-4, granulocyte macrophage colony stimulating factor and γ-interferons.

Suitable drug moieties include antineoplastic agents. Non-limiting examples include radioisotopes, vinca alkaloids such as the vinblastine, vincristine and vindesine sulfates, adriamycin, bleomycin sulfate, carboplatin, cisplatin, cyclophosphamide, cytarabine, dacarbazine, dactinomycin, duanorubicin hydrochloride, doxorubicin hydrochloride, etoposide, fluorouracil, lomustine, mechlororethamine hydrochloride, melphalan, mercaptopurine, methotrexate, mitomycin, mitotane, pentostatin, pipobroman, procarbaze hydrochloride, streptozotocin, taxol, thioguanine, and uracil mustard.

Immunotoxins, including antigen binding units, can be produced by recombinant means. Production of various immunotoxins is well-known in the art, and methods can be found, for example, in "Monoclonal Antibody-toxin Conjugates: Aiming the Magic Bullet," Thorpe et al. (1982) *Monoclonal Antibodies in Clinical Medicine*, Academic Press, pp. 168-190; Vitatta (1987) *Science* 238:1098-1104; and Winter and Milstein (1991) *Nature* 349:293-299. Suitable toxins include, but are not limited to, ricin, radionuclides, pokeweed antiviral protein, *Pseudomonas* exotoxin A, diphtheria toxin, ricin A chain, fungal toxins such as restrictocin and phospholipase enzymes. See, generally, "Chimeric Toxins," Olsnes and Pihl, *Pharmac. Ther.* 15:355-381 (1981); and "Monoclonal Antibodies for Cancer Detection and Therapy," eds. Baldwin and Byers, pp. 159-179, 224-266, Academic Press (1985).

Chemically functional moieties can be made recombinantly for instance by creating a fusion gene encoding the antigen binding unit and the functional moiety. Alternatively, the antigen binding unit can be chemically bonded to the moiety by any of a variety of well-established chemical procedures. For example, when the moiety is a protein, the linkage can be by way of heterobifunctional cross linkers, e.g., SPDP, carbodiimide glutaraldehyde, or the like. The moieties can be covalently linked, or conjugated, through a secondary reagent, such as a second antibody, protein A, or a biotin-avidin complex. Paramagnetic moieties and the conjugation thereof to antibodies are well-known in the art. See, e.g., Miltenyi et al. (1990) *Cytometry* 11:231-238.

Methods of Use

In one embodiment, the present disclosure provides methods of inducing cell death of cells comprising a WT1 peptide complexed with HLA, said method comprising contacting the cell with a subject chimeric antigen receptor.

In some examples, the cell is contacted with the chimeric antigen receptor in vivo. In other examples, the cell is contacted with the chimeric antigen receptor in vitro or ex vivo.

In some examples, the cell is a cancer cell. For example, the cancer cell can be a hematological cancer cell, a solid tumor cancer cell, a mesothelioma cancer cell, a colon cancer cell, or an intestinal cancer cell.

In one embodiment, the present disclosure provides methods of inducing death of target cells, the method comprising administering to the target cells a plurality of host cells expressing a subject antigen binding unit or chimeric antigen receptor, wherein administering the plurality of host cells to the target cells induces a greater degree of target cell death relative to administering a comparable amount of host cells lacking said antigen binding unit or chimeric antigen receptor or nucleic acid encoding the same.

In some examples, the plurality of host cells is administered to the target cells in vivo. In some examples, the plurality of host cells is administered to the target cells in vitro or ex vivo.

In some examples, the target cells are a cancer cells. For example, the cancer cells can be hematological cancer cells, solid tumor cancer cells, a mesothelioma cancer cells, a colon cancer cells, or an intestinal cancer cells In one embodiment, the present disclosure provides methods of treating a cancer in a subject, said method comprising administering to the subject an effective amount of a subject chimeric antigen receptor, or host cell comprising the same, wherein the chimeric antigen receptor induces death of the cancer cells. In some examples, the cancer is a hematological cancer, solid tumor cancer, mesothelioma cancer, colon cancer, or intestinal cancer.

In one embodiment, the present disclosure provides methods of treating a cancer in a subject in need thereof, said method comprising administering to the subject an effective amount of a subject antigen binding unit, or host cell comprising the same. In some examples, the cancer is a hematological cancer, solid tumor cancer, mesothelioma cancer, colon cancer, or intestinal cancer.

In one embodiment, the present disclosure provides methods of treating a cancer in a subject in need thereof, said method comprising administering to the subject an effective amount of a pharmaceutical composition comprising a subject pharmaceutical excipient and either a subject antigen binding unit or a subject chimeric antigen receptor. In some examples, the cancer is a hematological cancer, solid tumor cancer, mesothelioma cancer, colon cancer, or intestinal cancer.

Subjects treated by methods disclosed herein can exhibit a cancer or a solid tumor. Often, cancer cells or solid tumor cells express one or more tumor antigens. Typically, the tumor antigen is WT1 or a WT1 peptide, such as a WT1 peptide having the amino acid sequence of SEQ ID NO: 1. A subject exhibiting a cancer or solid tumor expressing a WT1 peptide complexed with HLA can be referred to as exhibiting a WT1-positive cancer.

Cancers that express a WT1 peptide complexed with HLA include but are not limited to liver cancer, stomach cancer, esophageal cancer, lung cancer, breast cancer, head and neck cancer, ovarian cancer, kidney cancer, bladder cancer, cervical cancer, pancreatic cancer, liposarcoma, testicular noneminomatous germ cell cancer, melanoma, adenoma, adrenal cancer, schwannoma, malignant, fibrous histiochytoma, mesothelioma, colon, intestinal, or any combination thereof. The subject methods are also applicable for treating squamous cell carcinoma or adenocarcinoma, neuroendocrine carcinoma of a GI tract. Additionally immunoresponsive cells disclosed herein, such as an anti-WT1-CAR-T cells disclosed herein, can be utilized to target ovarian carcinoma, cholangiocarcinoma, mesothelioma, breast cancer, squamous cell carcinoma of the lung, cervical intraethithelial neoplasia, squamous cell carcinoma of the cervix, intrahepatic and extrahepatic cancer, gallbladder carcinoma, invasive ductal carcinoma, clear cell carcinoma, oncocytoma, papillary carcinoma, adenocarcinoma, papillary carcinoma, and lobular and medullary carcinoma of the breast.

In some cases, a cancer or tumor cell can be evaluated for WT1 expression by flow cytometry or immunohistochemistry. A level of WT1 on a cancer or tumor cell can be classified as low, medium, or high.

In some cases, a cancer or tumor cell can express a WT1 peptide complexed with HLA on the cell surface. Expression of a WT1 peptide complexed with HLA on a cell surface can be determined, for example, using antibodies to WT1 in a method such as immunohistochemistry or flow cytometric analysis. Alternatively, WT1 mRNA expression can be considered to correlate to WT1 expression on a cell surface and can be determined by a method selected from in situ hybridization and RT-PCR.

A transgene encoding a subject anti-WT1 CAR can be incorporated into a cell. For example, a transgene can be incorporated into an immunoresponsive cell, such as a T cell. When inserted into a cell, a transgene can be either a complementary DNA (cDNA) segment, which is a copy of messenger RNA (mRNA), or a gene itself residing in its original region of genomic DNA (with or without introns).

A nucleic acid, e.g., DNA, encoding a transgene sequence can be randomly inserted into a chromosome of a cell. A random integration can result from any method of introducing a nucleic acid, e.g., DNA, into a cell. For example, the method can be, but is not limited to, electroporation, sonoporation, use of a gene gun, lipotransfection, calcium phosphate transfection, use of dendrimers, microinjection, and use of viral vectors including adenoviral, AAV, and retroviral vectors, and/or group II ribozymes.

A DNA encoding a transgene can be introduced into a cell via electroporation. A DNA can also be introduced into a cell via lipofection, infection, or transformation. Electroporation and/or lipofection can be used to transfect primary cells. Electroporation and/or lipofection can be used to transfect primary hematopoietic cells. A DNA can also be introduced into a cell genome without the use of homologous recombination. In some cases, a DNA can be flanked by engineered sites that are complementary to the targeted double strand break region in a genome. In some cases, a DNA can be excised from a polynucleic acid so it can be inserted at a double strand break region without homologous recombination.

A transgene to be inserted can be flanked by engineered sites analogous to a targeted double strand break site in the genome to excise the transgene from a polynucleic acid so it can be inserted at the double strand break region.

A DNA encoding a transgene can also be designed to include a reporter gene so that the presence of a transgene or its expression product can be detected via activation of the reporter gene. Any reporter gene can be used, such as those disclosed above. By selecting in cell culture those cells in which a reporter gene has been activated, cells can be selected that contain a transgene.

Expression of a subject anti-WT1 CAR can be verified by an expression assay, for example, qPCR or by measuring levels of RNA. Expression level can be indicative also of copy number. For example, if expression levels are extremely high, this can indicate that more than one copy of a CAR was integrated in a genome. Alternatively, high expression can indicate that a transgene was integrated in a highly transcribed area, for example, near a highly expressed promoter. Expression can also be verified by measuring protein levels, such as through Western blotting.

A subject anti-WT1 CAR immunoresponsive cell can comprise one or more transgenes. One or more transgenes can express a CAR protein recognizing and binding to at least one epitope (e.g., a WT1 peptide complexed with HLA) on an antigen or bind to a mutated epitope on an antigen. A CAR can be a functional CAR. A subject anti-WT1 CAR immunoresponsive cell can also comprise one or more CARs, or it can comprise a single CAR and a secondary engineered receptor.

A transgene can encode for a suicide gene. As evidenced in many effective treatments in cancer patients, objective tumor regressions in response to CAR immunoresponsive cells can be accompanied by toxicities. In some cases, a CAR immunoresponsive cell may be unable to distinguish between tumor and normal tissues when the targeted antigen is shared between them ("on-target/off-tumor" toxicity). In other cases, systemic perturbation of the immune system, known as cytokine release syndrome (CRS), can occur. Said CRS can comprise systemic inflammatory response syndrome or cytokine storm, which can be consequences of the rapid in vivo expansion of CAR immunoresponsive cells. CRS is a condition characterized by fever and hypotension that, in severe cases, can lead to multiple organ failure. In most cases, said toxicity correlates with the in vivo expansion of infused CAR immunoresponsive cells, which can cause a general perturbation of the immune system, and release of high levels of pro-inflammatory cytokines, such as TNF alpha and IL-6.

In some cases, CAR immunoresponsive cells targeting antigens shared with normal tissues can be generated such that they transiently express the CAR, for example after electroporation of mRNA encoding the receptor. In addition, there are significant efforts to further engineer CAR immunoresponsive cells by including safety switches that can allow the drastic elimination of CAR immunoresponsive cells in case of severe on-target toxicity. Vectors encoding a CAR can be combined with safety switches, such as the inducible caspase-9 gene (activated by a chemical inducer of dimerization) or a truncated form of the EGF receptor R (activated by the monoclonal antibody cetuximab) or RQR8.

A subject anti-WT1 CAR immunoresponsive cell can encode a suicide gene transgene. Said transgene can also comprise a CAR receptor or another similar receptor. A suicide gene can induce elimination of CAR immunoresponsive cells. A suicide gene can be any gene that induces apoptosis in said CAR immunoresponsive cell. A suicide gene can be encoded within a viral vector along with an anti-WT1 CAR.

One or more transgenes can be from different species. For example, one or more transgenes can comprise a human gene, a mouse gene, a rat gene, a pig gene, a bovine gene, a dog gene, a cat gene, a monkey gene, a chimpanzee gene, or any combination thereof. For example, a transgene can be from a human, having a human genetic sequence. One or more transgenes can comprise human genes. In some cases, one or more transgenes are not adenoviral genes.

A transgene can be inserted into a genome of an immunoresponsive cell in a random or site-specific manner, as described above. For example, a transgene can be inserted to a random locus in a genome of an immunoresponsive cell. These transgenes can be functional, e.g., fully functional if inserted anywhere in a genome. For instance, a transgene can encode its own promoter or can be inserted into a position where it is under the control of an endogenous promoter. Alternatively, a transgene can be inserted into a gene, such as an intron of a gene or an exon of a gene, a promoter, or a non-coding region. A transgene can be inserted such that the insertion disrupts a gene, e.g., an endogenous immune checkpoint.

Sometimes, more than one copy of a transgene can be inserted into more than a random locus in a genome. For example, multiple copies can be inserted into a random locus in a genome. This can lead to increased overall expression than if a transgene was randomly inserted once. Alternatively, a copy of a transgene can be inserted into a gene, and another copy of a transgene can be inserted into a different gene. A transgene can be targeted so that it could be inserted to a specific locus in a genome of a immunoresponsive cell.

In some cases, a polynucleic acid comprising a sequence encoding a subject anti-WT1 CAR, can take the form of a plasmid vector. A plasmid vector can comprise a promoter. In some cases, a promotor can be constitutive. In some cases, a promoter can be inducible. A promoter can be or can be derived from CMV, U6, MND, or EF1a. In some cases, a promoter can be adjacent to a CAR sequence. In some cases, a plasmid vector further comprises a splicing acceptor. In some cases, a splicing acceptor can be adjacent to a subject CAR sequence. A promoter sequence can be a PKG or an MND promoter. An MND promoter can be a synthetic promoter that contains a U3 region of a modified MoMuLV LTR with a myeloproliferative sarcoma virus enhancer.

In some cases, a polynucleic acid, encoding a subject anti-WT1 CAR, can be designed to be delivered to a cell by non-viral techniques. In some cases, a polynucleic acid can be a good manufacturing practices (GMP) compatible reagent.

Expression of a polynucleic acid encoding for a subject anti-WT1 CAR can be controlled by one or more promoters. A promoter can be a ubiquitous, constitutive (unregulated promoter that allows for continual transcription of an associated gene), tissue-specific promoter or an inducible promoter. Expression of a transgene that is inserted adjacent to or near a promoter can be regulated. For example, a transgene can be inserted near or next to a ubiquitous promoter. Some ubiquitous promoters can be a CAGGS promoter, an hCMV promoter, a PGK promoter, an SV40 promoter, or a ROSA26 promoter.

A promoter can be endogenous or exogenous. For example, one or more transgenes can be inserted adjacent or near to an endogenous or exogenous ROSA26 promoter. Further, a promoter can be specific to an immunoresponsive cell. For example, one or more transgenes can be inserted adjacent or near to a porcine ROSA26 promoter.

Tissue specific promoter or cell-specific promoters can be used to control the location of expression. For example, one or more transgenes can be inserted adjacent or near to a tissue-specific promoter. Tissue-specific promoters can be a FABP promoter, an Lck promoter, a CamKII promoter, a CD19 promoter, a Keratin promoter, an Albumin promoter, an aP2 promoter, an insulin promoter, an MCK promoter, a MyHC promoter, a WAP promoter, or a Col2A promoter.

Tissue specific promoter or cell-specific promoters can be used to control the location of expression. For example, one or more transgenes can be inserted adjacent or near to a tissue-specific promoter. Tissue-specific promoters can be a FABP promoter, an Lck promoter, a CamKII promoter, a CD19 promoter, a Keratin promoter, an Albumin promoter, an aP2 promoter, an insulin promoter, an MCK promoter, a MyHC promoter, a WAP promoter, or a Col2A promoter.

Inducible promoters can be used as well. These inducible promoters can be turned on and off when desired, by adding or removing an inducing agent. It is contemplated that an inducible promoter can be, but is not limited to, a Lac, tac, trc, trp, araBAD, phoA, recA, proU, cst-1, tetA, cadA, nar, PL, cspA, T7, VHB, Mx, and/or Trex.

Furthermore, although not required for expression, transgene sequence may also include transcriptional or translational regulatory sequences, for example, promoters, enhancers, insulators, internal ribosome entry sites, sequences encoding 2A peptides and/or polyadenylation signals.

In some instances, a transgene encodes a subject anti-WT1 CAR wherein the transgene is inserted into a safe harbor such that an anti-WT1 CAR is expressed. In some instances, the transgene is inserted into a PD1 and/or a CTLA-4 locus. In other cases, a transgene is delivered to the cell in a lentivirus for random insertion while the PD1- or CTLA-4 specific nucleases can be supplied as mRNAs. In some instances, the transgene is delivered via a viral vector system such as a retrovirus, AAV or adenovirus along with mRNA encoding nucleases specific for a safe harbor (e.g. AAVS1, CCR5, albumin or HPRT). The cells can also be treated with mRNAs encoding PD1 and/or CTLA-4 specific nucleases. In some cases, the polynucleotide encoding a CAR is supplied via a viral delivery system together with mRNA encoding HPRT specific nucleases and PD1- or CTLA-4 specific nucleases. CARs that can be used with the methods and compositions disclosed herein can include all types of these chimeric proteins, including first, second and third generation designs. Other agents such as CCR2 or siRNA can be applied to reduce PD-1 expression.

In some cases, a retroviral vector (either gamma-retroviral or lentiviral) can be employed for the introduction of the transgene into an immunoresponsive cell. For example, a transgene encoding a subject CAR (e.g., anti-WT1 CAR), or any receptor that binds a WT1 peptide complexed with HLA, can be cloned into a retroviral vector and expression can be driven from its endogenous promoter, from the retroviral long terminal repeat, or from a promoter specific for a target cell type of interest. Non-viral vectors may be used as well. Non-viral vector delivery systems can include DNA plasmids, naked nucleic acid, and nucleic acid complexed with a delivery vehicle such as a liposome or poloxamer.

A number of viral based systems have been developed for gene transfer into mammalian cells. For example, retroviruses provide a convenient platform for gene delivery systems. A selected gene can be inserted into a vector and packaged in retroviral particles using techniques known in the art. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells. They also have the added advantage of low immunogenicity. Adenoviral vectors have the advantage that they do not integrate into the genome of the target cell thereby bypassing negative integration-related events.

A cell can be transfected with a transgene encoding a subject CAR. A transgene concentration can be from about 100 picograms to about 50 micrograms. In some cases, the amount of nucleic acid (e.g., ssDNA, dsDNA, RNA) that may be introduced into a cell may be varied to optimize transfection efficiency and/or cell viability. For example, 1 microgram of dsDNA may be added to each cell sample for electroporation. In some cases, the amount of nucleic acid (e.g., dsDNA) required for optimal transfection efficiency and/or cell viability may be specific to the cell type. In some cases, the amount of nucleic acid (e.g., dsDNA) used for each sample may directly correspond to the transfection efficiency and/or cell viability. For example, a range of concentrations of transfections. A transgene encoded by a vector can integrate into a cellular genome. In some cases, integration of a transgene encoded by a vector is in the forward direction. In other cases, integration of a transgene encoded by a vector is in the reverse direction.

In some cases, the starting cell density for cellular modification, such as viral delivery of a subject CAR, may be varied to optimize transfection efficiency and/or cell viability. In some cases, the starting cell density for transfection or transduction of cells with a viral vector may be less than about $1 \times 10^5$ cells. In some cases, the starting cell density for cellular modification with a viral vector may be at least about $1 \times 10^5$ cells to at least about $5 \times 10^7$ cells. In some cases, the starting cell density for optimal transfection efficiency and/or cell viability may be specific to the cell type. For example, a starting cell density of $1.5 \times 10^6$ cells may optimal (e.g., provide the highest viability and/or transfection efficiency) for macrophage cells. In another example, a starting cell density of $5 \times 10^6$ cells may optimal (e.g., provide the highest viability and/or transfection efficiency) for human cells. In some cases, a range of starting cell densities may be optimal for a given cell type. For example, a starting cell density between of $5.6 \times 10^6$ and $5 \times 10^7$ cells may optimal (e.g., provide the highest viability and/or transfection efficiency) for human cells such as T cells.

The efficiency of integration of a nucleic acid sequence encoding a subject CAR into a genome of a cell with, for example, a viral system, can be or can be about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or more than 99.9%. In some cases, detection of a subject CAR on a cellular membrane of an engineered cell can be or can be about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or more than 99.9% as measured by flow cytometry.

In some cases, the immunoresponsive cell can be a stem memory $T_{SCM}$ cell comprised of CD45RO (−), CCR7(+), CD45RA (+), CD62L+ (L-selectin), CD27+, CD28+ and/or IL-7Rα+, said stem memory cells can also express CD95, IL-2Rβ, CXCR3, and/or LFA-1, and show numerous functional attributes distinctive of said stem memory cells. Alternatively, the immunoresponsive cell can also be central memory $T_{CM}$ cells comprising L-selectin and CCR7, where the central memory cells can secrete, for example, IL-2, but not IFNγ or IL-4. The immunoresponsive cells can also be effector memory $T_{EM}$ cells comprising L-selectin or CCR7 and produce, for example, effector cytokines such as IFNγ and IL-4.

Vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, T cells, bone marrow aspirates, tissue biopsy), followed by reimplantation of the cells into a patient, usually after selection for cells which have incorporated the vector. Prior to or after selection, the cells can be expanded.

A suitable immunoresponsive cell for expressing anti-WT1 CAR can be a cell that may be autologous or non-autologous to a subject in need thereof.

A source of suitable immunoresponsive cells can be obtained from a subject. In some cases T cells can be obtained. Said T cells can be obtained from a number of sources, including PBMCs, bone marrow, lymph node tissue, cord blood, thymus tissue, and tissue from a site of infection, ascites, pleural effusion, spleen tissue, and tumors. In certain cases, T cells can be obtained from a unit of blood collected from a subject using any number of techniques known to the skilled artisan, such as Ficoll™ separation. In one embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps.

Alternatively, a cell can be derived from a healthy donor, from a patient diagnosed with cancer, or from a patient diagnosed with an infection. In another embodiment, a cell can be part of a mixed population of cells which present different phenotypic characteristics. A cell line can also be obtained from a transformed T cell according to the method previously described. A cell can also be obtained from a cell therapy bank. Modified cells resistant to an immunosuppressive treatment can be obtained by any of the method described herein. A desirable cell population can also be selected prior to modification. An engineered cell population can also be selected after modification. An engineered cell can be used in autologous transplantation. Alternatively, a cell can be used in allogeneic transplantation. In some instances, a cell is administered to the same patient whose sample was used to identify the cancer-related target sequence. In other instances, a cell is administered to a patient different from the patient whose sample was used to identify the cancer-related target sequence.

In some cases, an immune responsive cell can be a primary cell including primary T cell, a stem cell, or a progenitor cell. A progenitor cell can be a hematopoietic progenitor cell. A cell of the present invention can be a human cell. Suitable cells can be expanded ex vivo. A suitable cell can also be CD45RO(−), CCR7(+), CD45RA(+), CD62L(+), CD27(+), CD28(+), IL-7Rα(+), or combinations thereof.

In some cases, suitable primary cells include peripheral blood mononuclear cells (PBMC), peripheral blood lymphocytes (PBL), and other blood cell subsets such as, but not limited to, T cell, a natural killer cell, a monocyte, a natural killer T cell, a monocyte-precursor cell, a hematopoietic stem cell or a non-pluripotent stem cell. In some cases, the cell can be any immune cells including any T cell such as tumor infiltrating cells (TILs), such as CD3+ T cells, CD4+ T cells, CD8+ T-cells, or any other type of T cell. The T cell can also include memory T cells, memory stem T cells, or effector T cells. The T cells can also be selected from a bulk population, for example, selecting T cells from whole blood. The T cells can also be expanded from a bulk population. The T cells can also be skewed towards particular populations and phenotypes. For example, the T cells can be skewed to phenotypically comprise, CD45RO (−), CCR7 (+), CD45RA (+), CD62 L(+), CD27 (+), CD28 (+) and/or IL-7Rα (+). Suitable cells can be selected that comprise one of more markers selected from a list comprising: CD45Rα (−), CCR7 (+), CD45RA (+), CD62L (+), CD27 (+), CD28 (+) and/or IL-7Rα (+). Suitable cells also include stem cells such as, by way of example, embryonic stem cells, induced pluripotent stem cells, hematopoietic stem cells, neuronal stem cells and mesenchymal stem cells. Suitable cells can comprise any number of primary cells, such as human cells, non-human cells, and/or mouse cells. Suitable cells can be progenitor cells. Suitable cells can be derived from the subject to be treated (e.g., patient). Suitable cells can be derived from a human donor. Suitable cells can be stem memory $T_{SCM}$ cells comprised of CD45RO (−), CCR7(+), CD45RA (+), CD62L+ (L-selectin), CD27+, CD28+ and IL-7Rα+, said stem memory cells can also express CD95, IL-2Rβ, CXCR3, and LFA-1, and show numerous functional attributes distinctive of said stem memory cells. Suitable cells can be central memory $T_{CM}$ cells comprising L-selectin and CCR7, said central memory cells can secrete, for example, IL-2, but not IFNγ or IL-4. Suitable cells can also be effector memory $T_{EM}$ cells comprising L-selectin or CCR7 and produce, for example, effector cytokines such as IFNγ and IL-4.

In some cases, a method can include enriching cultured T cells for CD8+ T cells prior to rapid expansion of cells. Following culture of T cells in IL-2, the T cells can be depleted of CD4+ cells and enriched for CD8+ cells using, for example, a CD8 microbead separation (e.g., using a CliniMACS$^{plus}$ CD8 microbead system (Miltenyi Biotec)). Without being bound to a particular theory, it can be believed that CD4+, CD25+ regulatory T-cells can impede anti-tumor responses. Accordingly, it can be believed that enriching cultured T cells for CD8+ T cells and reducing or eliminating CD4+ cells may improve the impact of adoptively transferred anti-tumor CD8+ cells, improve the response rates in patients, and/or reduce the toxicities seen by production of cytokines by CD4+ cells. Additionally, enriched CD8+ "young" T cells can be believed to behave more reliably and predictably in clinical scale rapid expansions than the bulk T cells.

A cell can be a good manufacturing practices (GMP) compatible reagent. A cell can be part of a combination therapy to treat cancer, infections, autoimmune disorders, or graft-versus-host disease (GVHD) in a subject in need thereof. In some cases, a cell of the present invention can be administered of a subject in need thereof as a monotherapy.

In some cases, cells expressing a subject CAR include heterogeneous T cell populations. In some cases, cells used can be largely composed of a heterogeneous proportion of CD4 and CD8 T cells. Said CD4 and CD8 cells can have phenotypic characteristics of circulating effector T cells. Said CD4 and CD8 cells can also have a phenotypic characteristic of effector-memory cells. In another embodiment, cells can be central-memory cells.

Suitable cells that can be isolated from a donor can be at any stage of development including, but not limited to, fetal, neonatal, young and adult. For example, donor immunoresponsive cells can be isolated from adult human Donor human immunoresponsive cells can be under the age of 10, 9, 8, 7, 6, 5, 4, 3, 2, or 1 year(s). For example, immunoresponsive cells can be isolated from a human under the age of 6 years. Immunoresponsive cells can also be isolated from a human under the age of 3 years. A donor can be older than 10 years.

A method of attaining suitable cells can comprise selecting based on a given marker. For example, such marker can comprise GFP, a resistance gene, a cell surface marker, or an endogenous tag. Cells can be selected using any endogenous marker. Applicable cell selection techniques include flow cytometry and/or magnetic columns. Selected cells can subsequently be infused into a subject. Selected cells can also be expanded to large numbers. Selected cells can be expanded prior to infusion.

The amount of cells that are necessary to be therapeutically effective in a patient may vary depending on the viability of the cells, and the efficiency with which the cells have been genetically modified (e.g., the efficiency with which a transgene has been integrated into one or more cells, or a level of expression of a protein encoded by the transgene). In some cases, the product (e.g., multiplication) of the viability of cells post genetic modification and the efficiency of integration of a transgene may correspond to the therapeutic aliquot of cells available for administration to a subject. In some cases, an increase in the viability of cells post genetic modification may correspond to a decrease in the amount of cells that are necessary for administration to be therapeutically effective in a patient. In some cases, an increase in the efficiency with which a transgene has been integrated into one or more cells may correspond to a decrease in the amount of cells that are necessary for administration to be therapeutically effective in a patient. In some cases, determining an amount of cells that are necessary to be therapeutically effective may comprise determining a function corresponding to a change in the viability of cells over time. In some cases, determining an amount of cells that are necessary to be therapeutically effective may comprise determining a function corresponding to a change in the efficiency with which a transgene may be integrated into one or more cells with respect to time dependent variables (e.g., cell culture time, electroporation time, cell stimulation time). In some cases, therapeutically effective cells can be a population of cells that comprise from about 30% to about 100% expression of an anti-WT1 CAR on a cellular surface. In some cases, therapeutically effective cells can express an anti-WT1 CAR on a cellular surface from about 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, to more than about 99.9% as measured by flow cytometry.

A variety of cells can be used to express the subject CAR, as described above. Anti-WT1 CAR can be present in the plasma membrane of a eukaryotic cell, e.g., a mammalian cell, where suitable mammalian cells include, but are not limited to, a cytotoxic cell, a T lymphocyte, a stem cell, a progeny of a stem cell, a progenitor cell, a progeny of a progenitor cell, and an NK cell.

When present in the plasma membrane of a eukaryotic cell, a subject CAR can be active in the presence of its binding target. For example, an anti-WT1 CAR can be active in the presence of a WT1 peptide complexed with HLA. A target, such as a WT1 peptide complexed with HLA, can be expressed on a membrane. A target can also be soluble (e.g., not bound to a cell). A target can be present on the surface of a cell such as a target cell. A target can be presented on a solid surface such as a lipid bilayer; and the like. A target can be soluble, such as a soluble antigen. A target can be an antigen. An antigen can be present on the surface of a cell such as a target cell. An antigen can be presented on a solid surface such as a lipid bilayer; and the like. In some cases, a target cell can be an epitope of an antigen. In methods disclosed herein, the antigen is typically a WT1 peptide complexed with HLA and the a WT1 peptide complexed with HLA expressing target cell is a cancer or tumor cell.

In some instances, a subject CAR, when present on the plasma membrane of a cell, and when activated by binding its target, can result in cytotoxic activity by the cell toward a target that expresses on its cell surface an antigen to which the binding domain of the CAR binds. For example, in some cases a cell can be a cytotoxic cell (e.g., an NK cell or a cytotoxic T lymphocyte), a CAR of the present disclosure, when present in the plasma membrane of a cell, and when activated by binding its target, can increase cytotoxic activity of a cytotoxic cell toward a target cell that expresses on its cell surface an antigen to which the binding domain of a CAR binds. For example, in some cases a cell can be an NK cell or a T lymphocyte, a CAR of the present disclosure, when present in the plasma membrane of a cell, and when activated by binding of its target, can increase cytotoxic activity of a cell by at least 10%, at least 15%, at least 20%, at least 25%, at least 30%, at least 40%, at least 50%, at least 75%, at least 2-fold, at least 2.5-fold, at least 5-fold, at least 10-fold, or more 10-fold, compared to the cytotoxic activity of the cell in the absence of the binding target.

In some cases, a subject CAR, when activated by binding its target, can result in other CAR activation related events such as proliferation and expansion (either due to increased cellular division or anti-apoptotic responses). Cellular proliferation can be visually measured by the observance of cellular clumping as seen under a microscope. Cellular expansion can be measured by a hemocytometer measurement. In some cases, a CAR-T cell can have increased cellular proliferation and expansion when compared to a comparable T cell, a non-CAR T cell. Increased cellular expansion can be from about 1 fold to about 20 hold over that of a comparable cell. Increased cellular expansion can be from about 1 fold, 2 fold, 3 fold, 4 fold, 5 fold, 6 fold, 7 fold, 8 fold, 9 fold, 10 fold, 11 fold, 12 fold, 13 fold, 14 fold, 15 fold, 16 fold, 17 fold, 18 fold, 19 fold, or up to 20 fold over that of a comparable cell. Cellular expansion can be measured over a period of time. For example, cellular expansion can take place from cellular acquisition to the time of infusion into a subject. In other cases, cellular expansion can take place from about 1 day to up to about 30 days after acquisition. Cellular expansion can take place from about 1, 2, 3, 4, 5, 6, 7, 8, 9, 10, 11, 12, 13, 14, 15, 16, 17, 18, 19, 20, 21, 22, 23, 24, 25, 26, 27, 28, 29, or up to 30 days after acquisition. In some cases, a rapid expansion protocol (REP) can be utilized to expand cells prior to infusion into a subject. A REP can occur over a period of about 14 days in some cases.

In some cases, a CAR, when activated by binding its target, can result in other CAR activation related events such as intracellular signaling modulation, cellular differentiation, or cell death. In some cases, expression of a CAR on a cell may alter intracellular signaling of a cell. In other cases, expression of a CAR may alter cellular differentiation.

One or more cytokines can be introduced with a subject CAR or host cell comprising the same. Cytokines can be utilized to boost transferred cells (including adoptively transferred tumor-specific cells) to expand within a tumor microenvironment. In some cases, IL-2 can be used to facilitate expansion of the cells described herein. Cytokines such as IL-15 can also be employed. Other relevant cytokines in the field of immunotherapy can also be utilized, such as IL-2, IL-7, IL-12, and, IL-21, or any combination thereof. In some cases, recombinant cytokines are used.

In some embodiments, a function of an immunoresponsive cell (e.g. T cell or an NK cell) comprising a subject CAR described herein may be enhanced by exposing the immunoresponsive cell to IL-12. In some cases, IL-12 can have immunomodulatory activity and can enhance the function of effector T cells, activated NK cells, or both.

Figure 11:
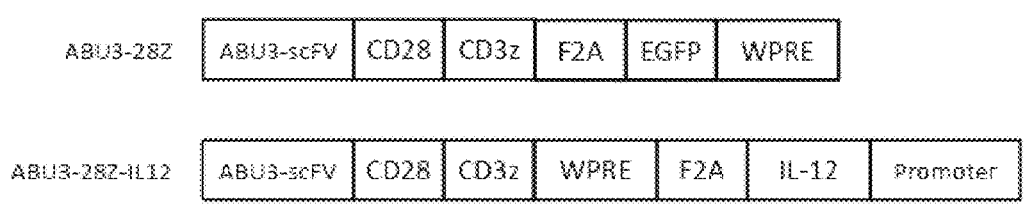
FIG. 11 depicts an example gene construct for a CAR-T cell expressing IL-12.

In some embodiments, the immunoresponsive cell comprising a subject CAR comprises IL-12, hereby exposing the immunoresponsive cell to IL-12. In some cases, the IL-12 is expressed on a surface of the immunoresponsive cell. In some cases, the IL-12 is expressed within the immunoresponsive cell. For example, FIG. 11 depicts an exemplary gene construct comprising a subject CAR and IL-12.

In some embodiments, the immunoresponsive cell is co-administered with cells that secrete IL-12. Examples of cells that secrete IL-12 include dendritic cells, and macrophages.

In other cases, IL-12 can be administered with the immunoresponsive cell comprising a subject CAR as described herein. In some cases, IL-12 is administered before, with, after, or a combination thereof, administration of the immunoresponsive cell comprising a subject CAR. In some cases, IL-12 can be administered with another cytokine, simultaneously or sequentially, in any order, and by the same route or different routes. In some embodiments, exposing the immunoresponsive cell to IL-12 enhances the cytotoxic effector function of the immunoresponsive cell. In some cases, the cytotoxicity of an immunoresponsive cell exposed to IL-12 may be at least 10%, at least 20%, at least 30%, at least 40%, at least 50%, at least 60%, at least 70% greater than the cytotoxicity of an immunoresponsive cell not exposed to IL-12.

In some cases, an immunoreponsive cell comprising a subject CAR described herein can be exposed to IL-12 and can have cytotoxicity of at least 20%, at least 30%, at least 40%, at least 50%, at least 60%, at least 70%, at least 80%, at least 90% or at least 90% in an in vitro cytotoxicity assay at an effector-to-target (E:T) ratio of 5:1.

In some cases, an immunoreponsive cell comprising a subject CAR described herein can be exposed to IL-12 and can have cytotoxicity of at least 20%, at least 30%, at least 40%, at least 50%, at least 60%, at least 70%, at least 80%, at least 90% or at least 90% in an in vitro cytotoxicity assay at an effector-to-target (E:T) ratio of 10:1.

In some cases, an immunoreponsive cell comprising a subject CAR described herein can be exposed to IL-12 and can have cytotoxicity of at least 20%, at least 30%, at least 40%, at least 50%, at least 60%, at least 70%, at least 80%, at least 90% or at least 90% in an in vitro cytotoxicity assay at an effector-to-target (E:T) ratio of 15:1.

In some cases, an immunoreponsive cell comprising a subject CAR described herein can be exposed to IL-12 and can have cytotoxicity of at least 20%, at least 30%, at least 40%, at least 50%, at least 60%, at least 70%, at least 80%, at least 90% or at least 90% in an in vitro cytotoxicity assay at an effector-to-target (E:T) ratio of 20:1.

In some embodiments, exposing the immunoresponsive cell to IL-12 enhances the cytokine-producing and/or secreting ability of the immunoresponsive cell. In some cases, the cytokine being produced and/or secreted is interferon-gamma (IFN-γ), tumor necrosis factor alpha (TNF-α), or IL-2. In other cases, exposing the immunoresponsive cell to IL-12 reduces IL-4 mediated suppression of IFN-γ.

In some cases, a T-cell growth factor can be administered with a subject CAR or host cell comprising the same. A growth factor can be administered by any suitable route. If more than one T cell growth factor is administered, they can be administered simultaneously or sequentially, in any order, and by the same route or different routes. A T cell growth factor, such as Aldesleukin (IL-2), can be administered intravenously as a bolus injection. A dosage of a T cell growth factor, such as IL-2, is what is considered by those of ordinary skill in the art to be high. Preferably, a dose of about 720,000 IU/kg of IL-2 can be administered three times daily until tolerance. Is come cases, about 5 to about 15 doses of IL-2 are administered, with an average of around 9 doses. A dosage of a T cell growth factor can be from about 0 to about 20. A T cell growth factor can be administered 1, 2, 3, 4, 5, 6, 7, 8, 9, 10, 11, 12, 13, 14, 15, 16, 17, 18, 19, or up to about 20 times.

IL-2 can be administered at a dose of 720,000 IU/kg (based on total body weight) as an intravenous bolus. In some cases, IL-2 can be administered over a 15-minute period. In some cases, IL-2 can be administered over a 20-minute period. IL-2 can be administered by immediate injection. In some cases IL-2 can be administered over 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 1 hour, 2 hours, 3 hours, 4 hours, 5 hours, or up to a period of 6 hours.

In some cases, IL-2 can be administered beginning within 24 hours of cell infusion and continuing for up to about 4 days (maximum 12 doses). In some cases, IL-2 can be administered for up to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 days after an initial administration.

Doses of IL-2 can be administered every eight hours. In some cases, IL-2 can be administered from about every 1, 2, 3, 4, 5, 6, 7, 8, 9, 10, 11, 12, 13, 14, 15, 16, 17, 18, 19, 20, 21, 22, 23, 24 hours after an initial administration. In some cases, IL-2 dosing can be stopped if toxicities are detected. In some cases, doses can be delayed or stopped if patients reach Grade 3 or 4 toxicity due to aldesleukin except for the reversible Grade 3 toxicities common to Aldesleukin such as diarrhea, nausea, vomiting, hypotension, skin changes, anorexia, mucositis, dysphagia, or constitutional symptoms and laboratory changes. In some cases, if these toxicities can be easily reversed within 24 hours by supportive measures, then additional doses may be given. In addition, dosing may be held or stopped at the discretion of the treating physician.

In some cases, an immunoresponsive cell that expresses an anti-WT1 CAR can have increased anti-tumor efficacy compared to a comparable immunoresponsive cell that does not express the anti-WT1 CAR.

In some cases, anti-tumor efficacy can refer to cytotoxic activity. In other cases, anti-tumor efficacy can refer to persistence. Anti-tumor efficacy can also refer to the ability of a cell to target a tumor. Anti-tumor efficacy can be measured using various in vitro assays. For example, cytotoxic ability can be measured by an ELISA that measures release of interleukin-2 (IL-2) or Interferon-γ (IFNγ). Cytotoxic activity can be measured by a killing assay such as a chromium-51 release assay or a co-culture assay. In some cases, anti-WT1 CAR immunoresponsive cells can have increased anti-tumor efficacy and ability when compared to comparable cells.

An anti-WT1 CAR treatment efficacy can be evaluated using multiple modalities. Efficacy can refer to anti-tumor efficacy that is the extent to which a tumor, such as a WT1-positive tumor, is controlled, reduced, or eliminated. Treatment efficacy can also refer to CAR immunoresponsive cell expansion, persistence, tumor-targeting, and any combination thereof.

A subject that can be administered an anti-WT1 CAR immunoresponsive cell therapy, such as anti-WT1 CAR T cell therapy, can be evaluated during an infusion, immediately after an infusion, or up to years following an infusion. For example, a treated subject can return to a clinic for evaluation for a period of about 1 day to the length of the subject's life. A treated subject can be evaluated from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, or up to 90 years after an initial administration of the subject CAR immunoresponsive cells. In some cases, an evaluation schedule can include daily monitoring, weekly monitoring, monthly monitoring, or yearly monitoring. In some cases, a subject can be seen more frequently as clinically indicated. An evaluation can include a physical exam, chemistry evaluation, complete blood count, thyroid panel, toxicity assessment, computerized tomography (CT) scan of a bodily area, apheresis, and any combination thereof.

In some cases, apheresis may be performed prior to and from about 1 to about 10 weeks following administration of a subject CAR immunoresponsive cell infusion. At other time points, a subject's peripheral blood lymphocytes (PBL) can be obtained from whole blood by purification using centrifugation on a Ficoll gradiant. Aliquots of peripheral blood mononuclear cells (PBMCs) can be cryopreserved for immunological monitoring of cell function. In some cases, a variety of tests can include evaluation of specific lysis and cytokine release, metabolomic and bioenergetic studies (using Seahorse), intracellular FACS of cytokine production, ELISA-spot assays, and lymphocyte subset analysis may be used to evaluate the immunological correlates of a subject CAR immunoresponsive cell treatment. In general, differences of about 2 to about 3 fold in these assays may be indicative of true biologic differences. In some cases, different of about 1, 1.5, 2, 2.5, 3, 3.5, 4, 4.5, up to about 5 fold of in vitro assays, post anti-WT1 CAR immunoresponsive cell therapy, may be indicative of treatment efficacy.

In some cases, a subject CAR immunoresponsive cell treatment may reduce tumor size as measured by computerized tomography (CT) scan or an MRI. An anti-WT1 CAR immunoresponsive cell treatment may reduce tumor size by at least about 5%, 10%, 15%, 20%, 25%, 30%, 35%, 40%, 45%, 50%, 55%, 60%, 65%, 70%, 75%, 80%, 85%, 90%, 95%, or up to about 100%. A CAR-T treatment may eliminate a tumor as measured by CT scan. In some cases, an anti-WT1 CAR immunoresponsive cell treatment may stabilize a tumor size as measured by a less than 10% change in a baseline measurement of a diameter of a tumor lesion as measured by computerized tomography (CT) scan. For example, a tumor may not expand in size after administration of anti-WT1 CAR immunoresponsive cells. In some cases, stabilization may be considered a less than 10%, 9%, 8%, 7%, 6%, 5%, 4%, 3%, 2%, or 1% change in tumor size as compared to a pre-treatment measurement.

In some cases, anti-WT1 CAR immunoresponsive cell efficacy can be considered in terms of subject survival time. For example, a subject that is treated with anti-WT1 CAR immunoresponsive cells, such as an anti-WT1 CAR T cells, can survive longer than an untreated subject or a subject treated with a different therapy.

In some cases, anti-WT1 CAR immunoresponsive cell efficacy can be improved by the addition of a secondary treatment. A secondary treatment can synergize with an anti-WT1 CAR immunoresponsive cell therapy. In some cases, a secondary treatment can produce additive effects of anti-WT1 CAR immunoresponsive cell therapy. A secondary treatment can be lymphocyte reduction, additional forms of cellular therapy, antibody therapy, chemotherapy, radiation therapy, surgery, anti-angiogenic therapy, and any combination thereof.

Treatment response can be evaluated using the international criteria proposed by the revised Response Evaluation Criteria in Solid Tumors (RECIST) guideline (Version 1.1). Changes in the largest diameter (unidimensional measurement) of a tumor lesion and the shortest diameter in the case of malignant lymph nodes can be used in the RECIST criteria. For example, measurable lesions can be those defined as those that can be accurately measured in at least one dimension (longest diameter to be recorded) as >20 mm by chest x-ray, as >10 mm with CT scan, or >10 mm with calipers by clinical exam. To be considered pathologically enlarged and measurable, a lymph node can be >15 mm in short axis when assessed by CT scan. All other lesions (or sites of disease), including small lesions (longest diameter <10 mm or pathological lymph nodes with ≥10 to <15 mm short axis), can be considered non-measurable disease. Bone lesions, leptomeningeal disease, ascites, pleural/pericardial effusions, lymphangitis cutis/pulmonitis, inflammatory breast disease, can be considered as non-measurable.

All measurable lesions up to a maximum of 2 lesions per organ and 5 lesions in total, representative of all involved organs, can be identified as target lesions and recorded and measured at baseline. Target lesions can be selected on the basis of their size (lesions with the longest diameter), be representative of all involved organs, but in addition should be those that lend themselves to reproducible repeated measurements. It may be the case that, on occasion, the largest lesion does not lend itself to reproducible measurement in which circumstance the next largest lesion which can be measured reproducibly should be selected. A sum of the diameters (longest for non-nodal lesions, short axis for nodal lesions) for all target lesions can be calculated and reported as the baseline sum diameters. If lymph nodes are to be included in the sum, then only the short axis can be added into the sum. A baseline sum diameter will be used as reference to further characterize any objective tumor regression in the measurable dimension of the disease.

In some cases, a clinical lesion can be considered measurable when it can be superficial (e.g., skin nodules and palpable lymph nodes) and about 10 mm diameter as assessed using calipers (e.g., skin nodules). In cases, where a caliper cannot be used to measure a lesion, a CT scan or MRI can also be used. In some cases, a CT scan can yield slices of tissue from about 5 mm or less. A CT scan can have 5 mm, 4 mm, 3 mm, 2 mm, 1 mm or 0.5 mm scan thickness in some cases. If a CT scan has a slice thickness greater than 5 mm, a minimum size for a measurable lesion can be twice the slice thickness. In some cases, an MRI can also be performed to evaluate a subject. Ideally, the same type of scanner should be used and the image acquisition protocol should be followed as closely as possible to prior scans when determining treatment efficacy. Body scans should be performed with breath-hold scanning techniques, if possible. In some cases, a fluorodeoxyglucose (FDG)-positron emission tomography (PET) can be used to measure treatment efficacy.

Once a subject has been evaluated, target lesions can be grouped into stable disease (SD), progressive disease (PD), partial response (PR), and/or a complete response (CR). A SD can be considered neither sufficient shrinkage to qualify for PR nor sufficient increase to qualify for PD, taking as reference the smallest sum of diameters. A PD can be considered at least a 20% increase in the sum of the diameters of target lesions, taking as reference the smallest sum (this can include the baseline sum if that may be the smallest). In some cases, in addition to a relative increase of about 20%, a sum must also demonstrate an absolute increase of at least about 5 mm A PR can be at least about 30% decrease in a sum of the diameters of target lesions, taking as reference the baseline sum of diameters. A CR can be elimination of target lesions.

Subject anti-WT1 antigen binding units or subject anti-WT1 CAR immunoresponsive cells can be formulation into a pharmaceutical medicament and be used to treat a human or mammal, in need thereof, diagnosed with a disease, e.g., cancer. These pharmaceutical medicaments can be co-administered to a human or mammal, together with one or more chemotherapeutic agent or chemotherapeutic compound.

Populations of subject CAR immunoresponsive cells, such as CAR T cells, may be formulated for administration to a subject using techniques known to the skilled artisan. Formulations comprising populations of CAR immunoresponsive cells may include pharmaceutically acceptable excipient(s). Excipients included in the formulations will have different purposes depending, for example, on the subpopulation of T cells used and the mode of administration. Examples of generally used excipients included, without limitation: saline, buffered saline, dextrose, water-for-injection, glycerol, ethanol, and combinations thereof, stabilizing agents, solubilizing agents and surfactants, buffers and preservatives, tonicity agents, bulking agents, and lubricating agents. The formulations comprising populations of CAR immunoresponsive cells will typically have been prepared and cultured in the absence of any non-human components, such as animal serum. A formulation may include one population of CAR immunoresposive cells, or more than one, such as two, three, four, five, six or more populations of CAR immunoresposive cells. For example, a formulation may include one population of CAR T cells, or more than one, such as two, three, four, five, six or more populations of CAR T cells.

Formulations comprising population(s) of anti-WT1 CAR immunoresponsive cells may be administered to a subject using modes and techniques known to the skilled artisan. Exemplary modes include, but are not limited to, intravenous injection. Other modes include, without limitation, intratumoral, intradermal, subcutaneous (S.C., s.q., sub-Q, Hypo), intramuscular (i.m.), intraperitoneal (i.p.), intra-arterial, intramedullary, intracardiac, intra-articular (joint), intrasynovial (joint fluid area), intracranial, intraspinal, and intrathecal (spinal fluids). Any known device useful for parenteral injection of infusion of the formulations can be used to effect such administration.

Formulations comprising population(s) of subject CAR immunoresponsive cells that are administered to a subject comprise a number of CAR immunoresponsive cells that is effective for the treatment and/or prophylaxis of the specific indication or disease. Thus, therapeutically-effective populations of CAR immunoresponsive cells can be administered to subjects. In general, formulations are administered that comprise between about $1 \times 10^4$ and about $1 \times 10^{10}$ CAR immunoresponsive cells. In most cases, the formulation will comprise between about $1 \times 10^5$ and about $1 \times 10^9$ CAR immunoresponsive cells, from about $5 \times 10^5$ to about $5 \times 10^8$ CAR immunoresponsive cells, or from about $1 \times 10^6$ to about 1×10⁷ CAR immunoresponsive cells. However, the number of CAR immunoresponsive cells administered to a subject will vary between wide limits, depending upon the location, source, identity, extent and severity of the cancer, the age and condition of the individual to be treated etc. A physician will ultimately determine appropriate dosages to be used.

Tumor-targeting molecules can be administered to a subject prior to, or concurrent with, or after administration of subject CAR immunoresponsive cells. The tumor-targeting molecules can bind to target cells in the subject by association to a tumor-associated antigen or a tumor-specific antigen. The tumor-targeting molecules may be formulated for administration to a subject using techniques known to the skilled artisan. Formulations of the tumor-targeting molecules may include pharmaceutically acceptable excipient(s). Examples of generally used excipients include, without limitation: saline, buffered saline, dextrose, water-for-injection, glycerol, ethanol, and combinations thereof, stabilizing agents, solubilizing agents and surfactants, buffers and preservatives, tonicity agents bulking agents, and lubricating agents.

The tumor-targeting molecules may be administered to a subject using modes and techniques known to the skilled artisan. Exemplary modes include, but are not limited to, intravenous, intraperitoneal, and intratumoral injection. Other modes include, without limitation, intradermal, subcutaneous (S.C., s.q., sub-Q, Hypo), intramuscular (i.m.), intra-arterial, intramedullary, intracardiac, intra-articular (joint), intrasynovial (joint fluid area), intracranial, intraspinal, and intrathecal (spinal fluids). In some cases, a CAR-T may be locally administered at a tumor lesion, such as a liver lesion. Any known device useful for parenteral injection or infusion of the formulations can be used to effect such administration.

Formulations comprising the tumor-targeting molecules are administered to a subject in an amount that is effective for treating and/or prophylaxis of the specific indication or disease. In general, formulations comprising at least about 0.1 mg/kg to about 100 mg/kg body weight of the tumor-targeting molecules are administered to a subject in need of treatment. In most cases, the dosage is from about 1 mg/kg to about 100 mg/kg body weight of the tagged proteins daily, taking into account the routes of administration, symptoms, etc. A physician will determine appropriate dosages to be used.

In one embodiment, a subject chimeric antigen receptor is used for stimulating an immunoresponsive cell-mediated immune response. For example, a T cell-mediated immune response is an immune response that involves the activation of T cells. Activated antigen-specific cytotoxic T cells are able to induce apoptosis in target cells displaying epitopes of foreign antigens on their surface, such as for example cancer cells displaying tumor antigens. In another embodiment, a chimeric antigen receptor is used to provide anti-tumor immunity in the mammal. Due to a T cell-mediated immune response the subject will develop an anti-tumor immunity.

In certain cases, methods of treating a subject having cancer can involve administering to a subject in need of treatment one or more formulations of tumor-targeting molecules, wherein these molecules bind to a cancer cell, and administering one or more therapeutically-effective populations of subject CAR immunoresponsive cells, wherein the CAR immunoresponsive cells can bind the tumor-targeting molecules and induce cancer cell death. Another embodiment can relate to methods of treating a subject having cancer comprising administering to a subject in need of treatment one or more therapeutically-effective populations of subject anti-WT1 CAR immunoresponsive cells, wherein the CAR immunoresponsive cells bind to a cancer cell, thereby inducing cancer cell death.

Administration frequencies of both formulations comprising anti-WT1 CAR immunoresponsive cells and anti-WT1 CAR immunoresponsive cells in combination with tumor-targeting molecules will vary depending on factors that include the disease being treated, the elements comprising the CAR immunoresponsive cells and the tumor-targeting molecules, and the modes of administration. Each formulation may be independently administered 4, 3, 2, or once daily, every other day, every third day, every fourth day, every fifth day, every sixth day, once weekly, every eight days, every nine days, every ten days, bi-weekly, monthly and bi-monthly.

A "chemotherapeutic agent" or "chemotherapeutic compound" and their grammatical equivalents as used herein, can be a chemical compound useful in the treatment of cancer. The chemotherapeutic cancer agents that can be used in combination with the disclosed CAR immunoresponsive cell include, but are not limited to, mitotic inhibitors (vinca alkaloids). These include vincristine, vinblastine, vindesine and Navelbine™ (vinorelbine, 5'-noranhydroblastine). In yet other embodiments, chemotherapeutic cancer agents include topoisomerase I inhibitors, such as camptothecin compounds. As used herein, "camptothecin compounds" include Camptosar™ (irinotecan HCL), Hycamtin™ (topotecan HCL) and other compounds derived from camptothecin and its analogues. Another category of chemotherapeutic cancer agents that can be used in the methods and compositions disclosed herein are podophyllotoxin derivatives, such as etoposide, teniposide and mitopodozide. The present disclosure further encompasses other chemotherapeutic cancer agents known as alkylating agents, which alkylate the genetic material in tumor cells. These include without limitation cisplatin, cyclophosphamide, nitrogen mustard, trimethylene thiophosphoramide, carmustine, busulfan, chlorambucil, belustine, uracil mustard, chlomaphazin, and dacarbazine. The disclosure encompasses antimetabolites as chemotherapeutic agents. Examples of these types of agents include cytosine arabinoside, fluorouracil, methotrexate, mercaptopurine, azathioprime, and procarbazine. An additional category of chemotherapeutic cancer agents that may be used in the methods and compositions disclosed herein includes antibiotics. Examples include without limitation doxorubicin, bleomycin, dactinomycin, daunorubicin, mithramycin, mitomycin, mytomycin C, and daunomycin. There are numerous liposomal formulations commercially available for these compounds. The present disclosure further encompasses other chemotherapeutic cancer agents including without limitation anti-tumor antibodies, dacarbazine, azacytidine, amsacrine, melphalan, ifosfamide and mitoxantrone.

Subject anti-WT1 CAR immunoresponsive cells can be administered in combination with other anti-tumor agents, including cytotoxic/antineoplastic agents and anti-angiogenic agents. Cytotoxic/anti-neoplastic agents can be defined as agents who attack and kill cancer cells. Some cytotoxic/anti-neoplastic agents can be alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents can be antimetabolites for tumor cells, e.g., cytosine arabinoside, fluorouracil, methotrexate, mercaptopuirine, azathioprime, and procarbazine. Other cytotoxic/anti-neoplastic agents can be antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents can be mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents can also be used. Suitable anti-angiogenic agents for use in the disclosed methods and compositions include anti-VEGF antibodies, including humanized and chimeric antibodies, anti-VEGF aptamers and antisense oligonucleotides. Other inhibitors of angiogenesis include angiostatin, endostatin, interferons, interleukin 1 (including a and 13) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with subject anti-WT1 CAR immunoresponsive cells include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; avastin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; CAR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

In some cases, subject anti-WT1 CAR immunoresponsive cell can be introduced by injection, catheter, or the like. In some cases, immunostimulatory agents can also be included, including, but not limited to, interleukins, e.g. IL-2, IL-3, IL-6, and IL-11, as well as the other interleukins, the colony stimulating factors, such as G-, M- and GM-CSF, interferons, e.g. .gamma.-interferon and erythropoietin. In some cases, a subject can be treated with a CAR-T, immunodepletant, and immunostimulant. A subject can be treated with IL-2 to boost performance of a CAR-T cellular product. In some cases, an immunostimulant can be a recombinant protein. An immunostimulant can also comprise an active portion of a protein. In some cases, an immunostimulant may only comprise a portion of a protein. A portion of a protein can be from about 50%, 60%, 70%, 80%, 90%, or up to about 100% of a protein.

Compositions comprising subject anti-WT1 CAR immunoresponsive cells, such as CAR T cells, can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof. Sterile injectable solutions can be prepared by incorporating genetically modified CAR immunoresponsive cells utilized in practicing the present invention in a required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation. Various additives which may enhance stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the genetically modified CAR immunoresponsive cells or their progenitors.

In some cases, compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions. Viscosity of compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

In some cases, for example, in the compositions, formulations and methods of treating cancer, the unit dosage of the composition or formulation administered can be 5, 10, 15, 20, 25, 30, 35, 40, 45, 50, 55, 60, 65, 70, 75, 80, 85, 90, 95 or 100 mg. In some cases, the total amount of the composition or formulation administered can be 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 40, 50, 60, 70, 80, 90, or 100 g.

In some cases, a pharmaceutical composition comprising a subject anti-WT1 CAR immunoresponsive cell, such as a CAR T cell, can be administered either alone or together with a pharmaceutically acceptable carrier or excipient, by any routes, and such administration can be carried out in both single and multiple dosages. More particularly, the pharmaceutical composition can be combined with various pharmaceutically acceptable inert carriers in the form of tablets, capsules, lozenges, troches, hand candies, powders, sprays, aqueous suspensions, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes.

For example, cells can be administered to a patient in conjunction with (e.g., before, simultaneously, or following) any number of relevant treatment modalities, including but not limited to treatment with agents such as antiviral therapy, cidofovir and interleukin-2, or Cytarabine (also known as ARA-C). In some cases, the engineered cells can be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. The engineered cell composition can also be administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In some cases, the engineered cell compositions can be administered following B-cell ablative therapy such as agents that react with CD20, e.g., Rituxan. For example, subjects can undergo standard treatment with high dose chemotherapy followed by peripheral blood stem cell transplantation. In certain embodiments, following the transplant, subjects can receive an infusion of the engineered cells, e.g., expanded engineered cells. Additionally, expanded engineered cells can be administered before or following surgery. The engineered cells obtained by any one of the methods described herein can be used for treating patients in need thereof against Host versus Graft (HvG) rejection and Graft versus Host Disease (GvHD). Therefore, a method of treating patients in need thereof against Host versus Graft (HvG) rejection and Graft versus Host Disease (GvHD) comprising treating said patient by administering to said patient an effective amount of engineered cells comprising inactivated TCR alpha and/or TCR beta genes can be contemplated.

Kits

Disclosed herein can be kits comprising compositions. Disclosed herein can also be kits for the treatment or prevention of a cancer, pathogen infection, immune disorder or allogeneic transplant. In one embodiment, a kit can include a therapeutic or prophylactic composition containing an effective amount of a cell comprising one or more anti-WT1 antigen binding unit or anti-WT1 CARs in unit dosage form. In some embodiments, a kit comprises a sterile container which may contain a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments. In some cases, a subject anti-WT1 CAR immunoresponsive cell, such as a CAR T cell, can be provided together with instructions for administering the CAR immunoresponsive cell to a subject having or at risk of developing a cancer, pathogen infection, immune disorder or allogeneic transplant. The instructions will generally include information about the use of the composition for the treatment or prevention of cancer, pathogen infection, immune disorder or allogeneic transplant. In some cases, a kit can include from about $1 \times 10^4$ cells to about $1 \times 10^{12}$ cells. In some cases a kit can include at least about $1 \times 10^5$ cells, at least about $1 \times 10^6$ cells, at least about $1 \times 10^7$ cells, at least about $4 \times 10^7$ cells, at least about $5 \times 10^7$ cells, at least about $6 \times 10^7$ cells, at least about $6 \times 10^7$ cells, at least about $8 \times 10^7$ cells, at least about $9 \times 10^7$ cells, at least about $1 \times 10^8$ cells, at least about $2 \times 10^8$ cells, at least about $3 \times 10^8$ cells, at least about $4 \times 10^8$ cells, at least about $5 \times 10^8$ cells, at least about $6 \times 10^8$ cells, at least about $6 \times 10^8$ cells, at least about $8 \times 10^8$ cells, at least about $9 \times 10^8$ cells, at least about $1 \times 10^9$ cells, at least about $2 \times 10^9$ cells, at least about $3 \times 10^9$ cells, at least about $4 \times 10^9$ cells, at least about $5 \times 10^9$ cells, at least about $6 \times 10^9$ cells, at least about $6 \times 10^9$ cells, at least about $8 \times 10^9$ cells, at least about $9 \times 10^9$ cells, at least about $1 \times 10^{10}$ cells, at least about $2 \times 10^{10}$ cells, at least about $3 \times 10^{10}$ cells, at least about $4 \times 10^{10}$ cells, at least about $5 \times 10^{10}$ cells, at least about $6 \times 10^{10}$ cells, at least about $6 \times 10^{10}$ cells, at least about $8 \times 10^{10}$ cells, at least about $9 \times 10^{10}$ cells, at least about $1 \times 10^{11}$ cells, at least about $2 \times 10^{11}$ cells, at least about $3 \times 10^{11}$ cells, at least about $4 \times 10^{11}$ cells, at least about $5 \times 10^{11}$ cells, at least about $6 \times 10^{11}$ cells, at least about $6 \times 10^{11}$ cells, at least about $8 \times 10^{11}$ cells, at least about $9 \times 10^{11}$ cells, or at least about $1 \times 10^{12}$ cells. For example, about $5 \times 10^{10}$ cells may be included in a kit. In another example, a kit may include $3 \times 10^6$ cells; the cells may be expanded to about $5 \times 10^{10}$ cells and administered to a subject.

In some cases, a kit may include allogenic cells. In some cases, a kit may include cells that may comprise a genomic modification. In some cases, a kit may comprise "off-the-shelf" cells. In some cases, a kit may include cells that may be expanded for clinical use. In some cases, a kit may contain contents for a research purpose.

In some cases, the instructions include at least one of the following: description of the therapeutic agent; dosage schedule and administration for treatment or prevention of a neoplasia, pathogen infection, immune disorder or allogeneic transplant or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container. In some cases, instructions provide procedures for administering the anti-WT1 antigen binding unit or anti-WT1 CAR immunoresponsive cells, such as CAR T cells, after administering a chemotherapeutic agent. In some cases, instructions provide procedures for administering the anti-WT1 antigen binding unit or anti-WT1 CAR immunoresponsive cells before administering a chemotherapeutic agent. In some cases, instructions provide procedures for administering the anti-WT1 antigen binding unit or anti-WT1 CAR immunoresponsive cells concurrent with administering a chemotherapeutic agent. In some cases, instructions provide procedures for administering anti-WT1 antigen binding unit or anti-WT1 CAR immunoresponsive cells at least 12 hours after administering a chemotherapeutic agent. In some cases, instructions provide procedures for administering anti-WT1 antigen binding unit or anti-WT1 CAR immunoresponsive cells at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or up to 2 days, 3 days, 4 days, 5 days, 6 days, or 7 days after administering a chemotherapeutic agent. In some cases, instructions provide procedures for administering anti-WT1 antigen binding unit or anti-WT1 CAR immunoresponsive cells at least 24 hours after administering a chemotherapeutic agent. Anti-WT1 antigen binding unit or anti-WT1 CAR immunoresponsive cells can be formulated for intravenous injection. Anti-WT1 antigen binding unit or anti-WT1 CAR immunoresponsive cells can be formulated for intra-arterial injection to a subject's liver that can comprise a solid tumor.

In some cases, a kit may contain cyclophosphamide and/or fludarabine, formulated for administration to a subject in need thereof at about 60 mg/kg to about 80 mg/kg and at about 25 mg/m$^2$ to about 35 mg/m$^2$, respectively. In some cases a kit may contain products at a pediatric dosage.

Recombinant methods are well known in the art. The practice of the invention employs, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (Gait, ed., 1984); "Animal Cell Culture" (Freshney, ed., 1987); "Methods in Enzymology" (Academic Press, Inc.); "Handbook of Experimental Immunology" (Wei & Blackwell, eds.); "Gene Transfer Vectors for Mammalian Cells" (Miller & Calos, eds., 1987); "Current Protocols in Molecular Biology" (Ausubel et al., eds., 1987); "PCR: The Polymerase Chain Reaction", (Mullis et al., eds., 1994); and "Current Protocols in Immunology" (Coligan et al., eds., 1991). These techniques are applicable to the production of the polynucleotides and polypeptides, and, as such, can be considered in making and practicing the invention. Particularly useful techniques for are discussed in the sections that follow.

The method disclosed herein can comprise transplanting. Transplantation can refer to adoptive transplantation of a cellular product. Transplanting can be autotransplanting, allotransplanting, xenotransplanting, or any other transplanting. For example, transplanting can be xenotransplanting. Transplanting can also be allotransplanting.

In some cases, about $5 \times 10^{10}$ subject anti-WT1 CAR immunoresponsive cells are administered to a subject. In some embodiments, about $5 \times 10^{10}$ cells represents a median amount of cells administered to a subject. In some embodiments, about $5 \times 10^{10}$ cells are necessary to affect a therapeutic response in a subject. In some embodiments, at least about at least about $1 \times 10^7$ cells, at least about $2 \times 10^7$ cells, at least about $3 \times 10^7$ cells, at least about $4 \times 10^7$ cells, at least about $5 \times 10^7$ cells, at least about $6 \times 10^7$ cells, at least about $6 \times 10^7$ cells, at least about $8 \times 10^7$ cells, at least about $9 \times 10^7$ cells, at least about $1 \times 10^8$ cells, at least about $2 \times 10^8$ cells, at least about $3 \times 10^8$ cells, at least about $4 \times 10^8$ cells, at least about $5 \times 10^8$ cells, at least about $6 \times 10^8$ cells, at least about $6 \times 10^8$ cells, at least about $8 \times 10^8$ cells, at least about $9 \times 10^8$ cells, at least about $1 \times 10^9$ cells, at least about $2 \times 10^9$ cells, at least about $3 \times 10^9$ cells, at least about $4 \times 10^9$ cells, at least about $5 \times 10^9$ cells, at least about $6 \times 10^9$ cells, at least about $6 \times 10^9$ cells, at least about $8 \times 10^9$ cells, at least about $9 \times 10^9$ cells, at least about $1 \times 10^{10}$ cells, at least about $2 \times 10^{10}$ cells, at least about $3 \times 10^{10}$ cells, at least about $4 \times 10^{10}$ cells, at least about $5 \times 10^{10}$ cells, at least about $6 \times 10^{10}$ cells, at least about $6 \times 10^{10}$ cells, at least about $8 \times 10^{10}$ cells, at least about $9 \times 10^{10}$ cells, at least about $1 \times 10^{11}$ cells, at least about $2 \times 10^{11}$ cells, at least about $3 \times 10^{11}$ cells, at least about $4 \times 10^{11}$ cells, at least about $5 \times 10^{11}$ cells, at least about $6 \times 10^{11}$ cells, at least about $6 \times 10^{11}$ cells, at least about $8 \times 10^{11}$ cells, at least about $9 \times 10^{11}$ cells, or at least about $1 \times 10^{12}$ cells. For example, about $5 \times 10^{10}$ cells may be administered to a subject. In another example, starting with $3 \times 10^6$ cells, the cells may be expanded to about $5 \times 10^{10}$ cells and administered to a subject. In some cases, cells are expanded to sufficient numbers for therapy. For example, $5 \times 10^7$ cells can undergo rapid expansion to generate sufficient numbers for therapeutic use. In some cases, sufficient numbers for therapeutic use can be $5 \times 10^{10}$. Any number of cells can be infused for therapeutic use. For example, a subject may be infused with a number of cells between $1 \times 10^6$ to $5 \times 10^{12}$ inclusive. A patient may be infused with as many cells that can be generated for them. In some cases, cells that are infused into a patient are not all engineered. For example, at least 90% of cells that are infused into a patient can be engineered. In other instances, at least 40% of cells that are infused into a patient can be engineered. In some embodiments, a method can comprise calculating and/or administering to a subject an amount of engineered cells necessary to affect a therapeutic response in the subject. In some embodiments, calculating the amount of engineered cells necessary to affect a therapeutic response comprises the viability of the cells and/or the efficiency with which an anti-WT1 CAR transgene has been integrated into the genome of a cell. In some embodiments, in order to affect a therapeutic response in a subject, the cells administered to the subject may be viable cells. In some embodiments, in order to effect a therapeutic response in a subject, at least about 95%, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20%, at least about 15%, at least about 10% of the cells are viable cells. In some embodiments, in order to affect a therapeutic response in a subject, the cells administered to a subject may be cells that have had one or more transgenes successfully integrated into the genome of the cell. In some embodiments, in order to effect a therapeutic response in a subject, at least about 95%, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20%, at least about 15%, at least about 10% of the cells have had one or more CAR transgenes successfully integrated into a genome of a cell.

In some cases, a subject can be administered subject anti-WT1 CAR immunoresponsive cells, wherein CAR immunoresponsive cells that can be administered may be about 1 to about 35 days old. For example, administered cells may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or up to about 40 days old. An age of a CAR immunoresponsive cell can be considered from a time of stimulation. An age of a CAR immunoresponsive cell can be considered from a time of apheresis. An age of a CAR immunoresponsive cell can be considered from a time of transduction. In some embodiments, CAR immunoresponsive cell that can be administered to a subject are about 10 to about 14 or about 20 days old. In some cases, an "age" of a CAR immunoresponsive cell can be determined by a length of a telomere. For example, a "young" CAR immunoresponsive cell can have a longer telomere length than an "exhausted" or "old" CAR immunoresponsive cell. Without being bound to a particular theory, it can be believed that immunoresponsive cells lose an estimated telomere length of about 0.8 kb per week in culture, and that young CAR immunoresponsive cell cultures can have telomeres that are about 1.4 kb longer than immunoresponsive cells that are about 44 days old. Without being bound to a particular theory, it is believed that longer telomere lengths can be associated with positive objective clinical responses in patients and persistence of the cells in vivo.

In some cases, cells are isolated from the subject organism, transfected with a nucleic acid (e.g., gene or cDNA), and re-infused back into the subject organism (e.g., patient).

Cells (e.g., engineered cells or engineered primary T cells) before, after, and/or during transplantation can be functional. For example, transplanted cells can be functional for at least or at least about 1, 2, 3, 4, 5, 6, 7, 8, 9, 10, 11, 12, 13, 14, 15, 16, 17, 18, 19, 20, 21, 22, 23, 24, 25, 6, 27, 28, 29, 30, 40, 50, 60, 70, 80, 90, or 100 days after transplantation. Transplanted cells can be functional for at least or at least about 1, 2, 3, 4, 5, 6, 7, 8, 9, 10, 11, or 12 months after transplantation. Transplanted cells can be functional for at least or at least about 1, 2, 3, 4, 5, 6, 7, 8, 9, 10, 15, 20, 25, or 30 years after transplantation. In some cases, transplanted cells can be functional for up to the lifetime of a recipient.

Further, transplanted cells can function at 100% of their normal intended function. Transplanted cells can also function 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or up to about 100% of their normal intended function.

Transplanted cells can also function over 100% of their normal intended function. For example, transplanted cells can function 110, 120, 130, 140, 150, 160, 170, 180, 190, 200, 250, 300, 400, 500, 600, 700, 800, 900, 1000, or up to about 5000% of their normal intended function.

Transplanting can be by any type of transplanting. Sites can include, but not limited to, liver subcapsular space, splenic subcapsular space, renal subcapsular space, omentum, gastric or intestinal submucosa, vascular segment of small intestine, venous sac, testis, brain, spleen, or cornea. For example, transplanting can be subcapsular transplanting. Transplanting can also be intramuscular transplanting. Transplanting can be intraportal transplanting.

After treatment (e.g., any of the treatment as disclosed herein), transplant rejection can be improved as compared to when one or more wild-type cells is transplanted into a recipient. For example, transplant rejection can be hyperacute rejection. Transplant rejection can also be acute rejection. Other types of rejection can include chronic rejection. Transplant rejection can also be cell-mediated rejection or T cell-mediated rejection. Transplant rejection can also be natural killer cell-mediated rejection.

Improving transplantation can mean lessening hyperacute rejection, which can encompass a decrease, lessening, or diminishing of an undesirable effect or symptom. Transplantation can refer to adoptive transplantation of a cellular product.

Another indication of successful transplantation can be the days a recipient does not require immunosuppressive therapy. For example, after treatment (e.g., transplantation) provided herein, a recipient can require no immunosuppressive therapy for at least or at least about 1, 2, 3, 4, 5, 6, 7, 8, 9, 10 or more days. This can indicate that transplantation was successful. This can also indicate that there is no rejection of the transplanted cells, tissues, and/or organs.

In some cases, a recipient can require no immunosuppressive therapy for at least 1 day. A recipient can also require no immunosuppressive therapy for at least 7 days. A recipient can require no immunosuppressive therapy for at least 14 days. A recipient can require no immunosuppressive therapy for at least 21 days. A recipient can require no immunosuppressive therapy for at least 28 days. A recipient can require no immunosuppressive therapy for at least 60 days. Furthermore, a recipient can require no immunosuppressive therapy for at least 1, 2, 3, 4, 5, 6, 7, 8, 9, 10, or more years.

Another indication of successful transplantation can be the days a recipient requires reduced immunosuppressive therapy. For example, after the said treatment provided herein, a recipient can require reduced immunosuppressive therapy for at least 1, 2, 3, 4, 5, 6, 7, 8, 9, 10 or more days. This can indicate that transplantation was successful. This can also indicate that there is no or minimal rejection of the transplanted cells, tissues, and/or organs.

For example, a recipient can require reduced immunosuppressive therapy for at least 1 day. A recipient can also require reduced immunosuppressive therapy for at least 7 days. A recipient can require reduced immunosuppressive therapy for at least 14 days. A recipient can require reduced immunosuppressive therapy for at least 21 days. A recipient can require reduced immunosuppressive therapy for at least 28 days. A recipient can require reduced immunosuppressive therapy for at least 60 days. Furthermore, a recipient can require reduced immunosuppressive therapy for at least 1, 2, 3, 4, 5, 6, 7, 8, 9, 10 or more years.

Reduced immunosuppressive therapy can refer to less immunosuppressive therapy compared to a required immunosuppressive therapy when one or more wild-type cells is transplanted into a recipient.

Immunosuppressive therapy can comprise any treatment that suppresses the immune system. Immunosuppressive therapy can help to alleviate, minimize, or eliminate transplant rejection in a recipient. For example, immunosuppressive therapy can comprise immuno-suppressive drugs. Immunosuppressive drugs that can be used before, during and/or after transplant, but are not limited to, MMF (mycophenolate mofetil (Cellcept)), ATG (anti-thymocyte globulin), anti-CD154 (CD40L), anti-CD40 (2C10, ASKP1240, CCFZ533X2201), alemtuzumab (Campath), anti-CD20 (rituximab), anti-IL-6R antibody (tocilizumab, Actemra), anti-IL-6 antibody (sarilumab, olokizumab), CTLA4-Ig (Abatacept/Orencia), belatacept (LEA29Y), sirolimus (Rapimune), everolimus, tacrolimus (Prograf), daclizumab (Ze-napax), basiliximab (Simulect), infliximab (Remicade), cyclosporin, deoxyspergualin, soluble complement receptor 1, cobra venom factor, compstatin, anti C5 antibody (eculizumab/Soliris), methylprednisolone, FTY720, everolimus, leflunomide, anti-IL-2R-Ab, rapamycin, anti-CXCR3 antibody, anti-ICOS antibody, anti-OX40 antibody, and anti-CD122 antibody. Furthermore, one or more than one immunosuppressive agents/drugs can be used together or sequentially. One or more than one immunosuppressive agents/drugs can be used for induction therapy or for maintenance therapy. The same or different drugs can be used during induction and maintenance stages. In some cases, daclizumab (Zenapax) can be used for induction therapy and tacrolimus (Prograf) and sirolimus (Rapimune) can be used for maintenance therapy. Daclizumab (Zenapax) can also be used for induction therapy and low dose tacrolimus (Prograf) and low dose sirolimus (Rapimune) can be used for maintenance therapy. Immunosuppression can also be achieved using non-drug regimens including, but not limited to, whole body irradiation, thymic irradiation, and full and/or partial splenectomy. These techniques can also be used in combination with one or more immuno-suppressive drugs.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: Preparation of HLA-Peptide Complex

HLA.A0201-BSP gene was synthesized in vitro (SEQ ID NO: 32). As shown in FIG. 1, the fusion gene comprises, from N terminal to C terminal, sections for encoding extracellular region of HLA.A0201 molecular without signaling peptide (SEQ ID NO: 34), a short "GS" linker, and biotin protein ligase BirA substrate peptide (BSP). pET22b-HLA.A0201-BSP was constructed by inserting the NdeI/Bam H I digested fusion gene into the pET-22b expression vector.

Human β2m expression vector (pET22b-β2m) was constructed similarly by synthesizing in vitro human β2m gene (SEQ ID NO: 33), and inserting the NdeI/Bam H I digested gene into pET-22b expression plasmid.

pET22b-HLA.A0201-BSP and pET22b-β2m were then transformed into BL21, and the strains with high expression level of pET22b-HLA and pET22b-β2m were grown overnight in 2YT medium at 37° C. on a shaker. On day 2, the overnight culture was seeded in 2YT medium at a final concentration of 50 μg/ml, and grown on a shaker at 250 rpm, at 37° C. for 3 h. Isopropyl β-D-1-thiogalactopyranoside (IPTG) was added to a final concentration of 1 mM once $OD_{600}$ was about 0.8. The mixture was cultivated to peptide for 4 h at 37° C. and 220 rpm. Cells were collected by centrifugation (8,000 rpm) at 4° C., and re-suspended in a buffer (50 mM Tris, 25% sucrose, 10 mM DTT, 1 mM EDTA, 1% Triton X-100, and 1 mM PMSF, pH8.0) at 40 ml buffer/400 ml cells. The suspension was then homogenized by ultrasound (99*3 s at 3 s interval, 400 W) for a total of three times. The supernatant was collected by centrifugation at 13,000 rpm (15 min).

Cells were harvested from 200 μl of control culture and expression culture respectively and centrifugated (8,000 rpm) at 4° C. The cells were then re-suspended into 30 μl loading buffer, boiled for 10 min, and centrifugated at 13,000 rpm for 2 min. 6 μl of supernatant was used in electrophoresis to verify expression.

The homogenized cells (6 μl) were subject to electrophoresis for both the supernatant (Soluble, S) and the precipitation (Insoluble, I), respectively. SDS-PAGE verified expression of HLA and β2m, both in inclusion bodies.

The precipitation resulted from homogenization was re-suspended into a buffer (50 mMTris, 1 mMDTT, 1 mMEDTA, 0.5% Triton X-100, and 0.1M NaCl; pH8.0), shaken at 4° C. for 2 h, and then centrifugated at 13,000 rpm for 15 min to collect the precipitation. The precipitation was washed 5 times till the inclusion bodies turned white.

The washed inclusion bodies were then re-suspended into 30 ml of 10 mM Tris and 8M urea at pH 8.0. The supernatant was loaded on 1.5 ml Q column after shaking and centrifugation. The column was equilibrated with a buffer (10 mM Tris and 8M urea; pH8.0) for 5 column volume (CV). 30 ml of sample was eluted through the Q column, flow-through collected. E1 was collected by flowing through the column another 15 ml of buffer with a conductivity of 3 (10 mM Tris and 8M urea; pH8.0); E2 was collected by flowing through another 15 ml buffer with a conductivity of 5 (10 mM Tris and 8M urea; pH8.0); and E3 was collected by another 15 ml buffer with a conductivity of 7 (10 mM Tris and 8M urea; pH8.0).

HLA fraction was obtained by combining E1 and E2, and β2m fraction was obtained by combining flow-through and E2. 2 mM DTT and 1 mM EDTA were added into the fractions and the proteins were refolded at room temperature for 2 h. HLA and β2m were concentrated with ultrafiltration to a final concentration of about 10 mg/ml each, and kept in −80° C.

Peptides of Table 7, purchased from GL Biochem (Shanghai) Ltd., were used to prepare different HLA-peptide complex. RMF is the 126-134 fragment of WT1. Irrelevant peptide YLL is from LMP-1. These complexes were used to confirm the specificity of the antibodies disclosed herein.

TABLE 7

| SEQ ID NO: | Abbreviation | Source protein |
| --- | --- | --- |
| SEQ ID NO: 1 | RMF | WT1 |
| SEQ ID NO: 58 | RMFS1 | Mediator complex subunit 13-like (MED13L) |
| SEQ ID NO: 59 | RMFS2 | Phosphatidylinositol glycan anchor biosynthesis, class Q (PIGQ) |
| SEQ ID NO: 65 | YLL | Latent membrane protein-1 (LMP-1) |

Figure 2A:
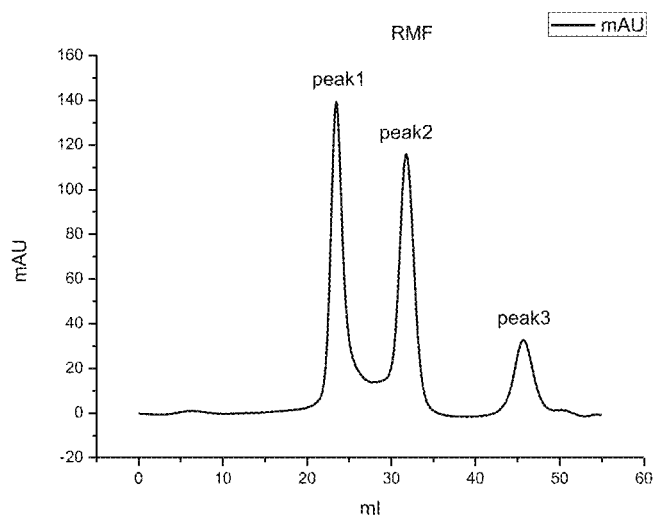
FIG. 2A and FIG. 2B depict an example chromatogram and agarose gel purification, respectively, of isolated polypeptides.
Figure 2B:
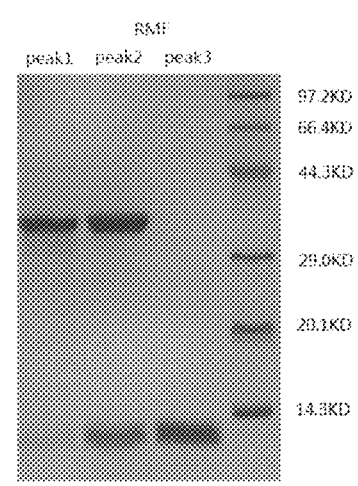

The peptides of Table 6 were refolded with a refolding buffer (0.1M Tris, 2 mM EDTA, 5 mM GSH, 0.5 mM SSG, and 0.2 mM PMSF; pH8.0), and dialyzed against PBS buffer supplemented with 5% glycerol. The peptides were then concentrated by ultrafiltration, and each arrived at a final volume of around 1.8 ml. The concentrated peptides were purified with Superdex75 chromatography. Result is shown in FIG. 2. Peak one corresponds to the uncomplexed HLA polypeptide. Peak 2 corresponds to a HLA-WT1 peptide complex. Peak 3 corresponds to the uncomplexed β2m.

The complexes were then labeled with biotinylation kit (BirA, Solution A, Solution B, d-biotin; Avidity, Colo., USA).

Example 2: Screening scFvs that Specifically Bind to RMF/HLA Complex Using Fully Human Phage Display Library A library of phage displaying the WT1 peptide (RMF) (SEQ ID NO: 1) complexed with HLA was generated and used to screen for scFvs that specifically bind to the complex. Numerous scFvs were isolated having a linker (SEQ ID NO: 53) that connects $V_H$ and $V_L$ fragments.

Example 3: Binding Affinity Analysis of ABU1 and ABU2

Figure 3:
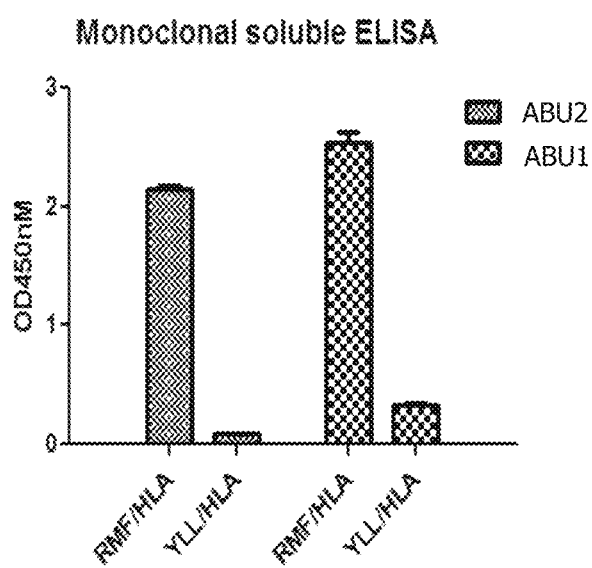
FIG. 3 depicts data from an example ELISA assay.
Figure 4:
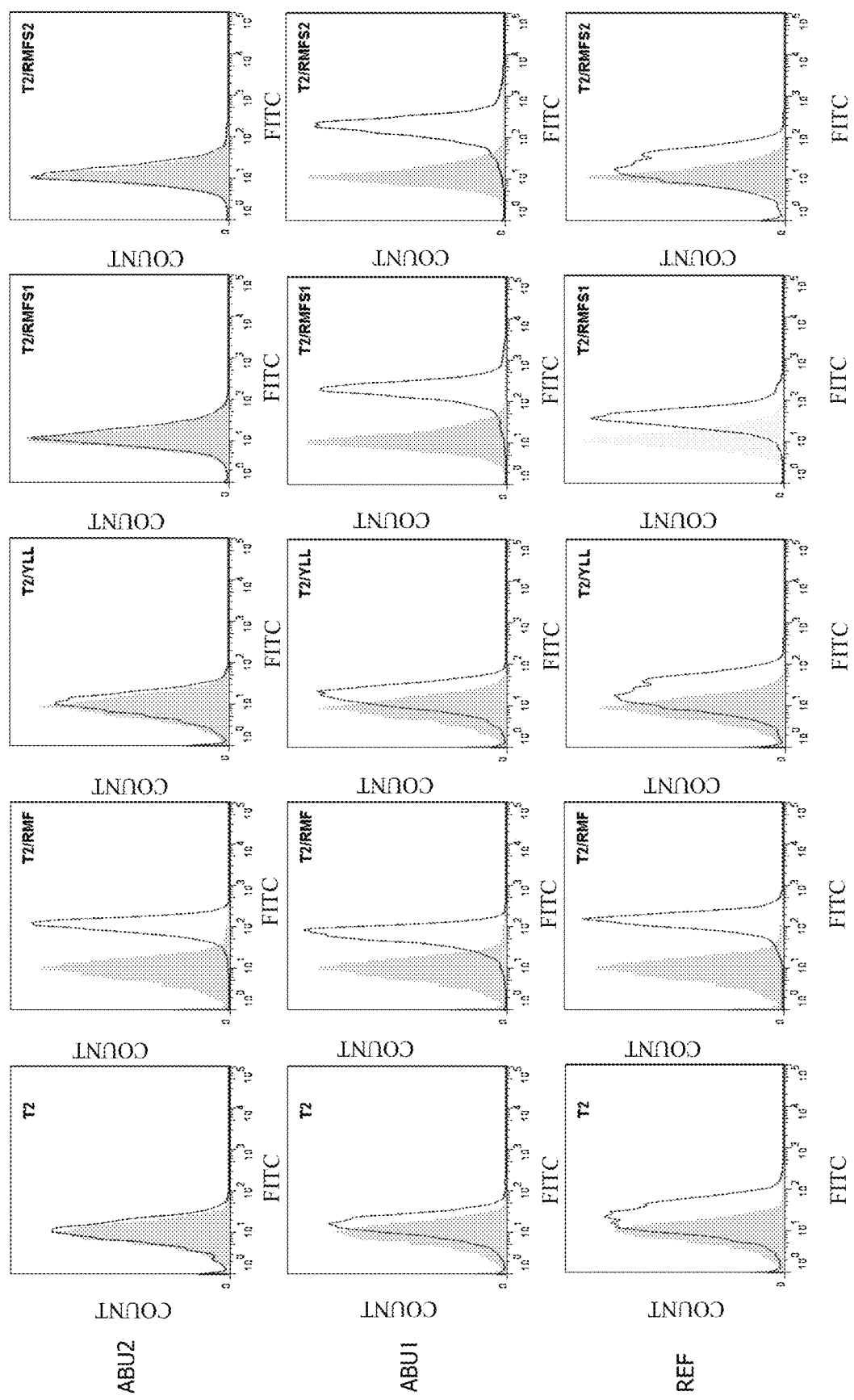
FIG. 4 depicts data from an example binding assay.

Select scFvs termed antigen binding unit 1 (ABU1) and ABU2 were assessed for their binding affinity to the WT1 peptide (RMF) complexed with HLA by performing ELISA assays (FIG. 3) and FACS analysis (FIG. 4).

FIG. 3 depicts the results from an example ELISA assay. As shown in FIG. 3, both ABUT and ABU2 were proved to be highly specific to RMF/HLA.A0201 complex.

FIG. 4 depicts the FACS results from an example binding affinity assay. ABU1 and ABU2 along with the reference (REF) scFv (SEQ ID NO: 60) were assessed in this example. T2 cell line was used which are inherently WT1 negative and HLA positive. T2 was then engineered to express the WT1 peptide (T2/RMF), the YLL negative control (T2/YLL), reference peptide RMFS1 (T2/RMFS1), or reference peptide RMFS2 (T2/RMFS2). ABU1 and ABU2 both specifically bind to the WT1 peptide complexed with HLA (T2/RMF). The reference antigen binding unit (REF) has higher non-specific binding to RMFS1 and RMFS2 than ABU2 does.

Example 4: Affinity Maturation

Figure 5:
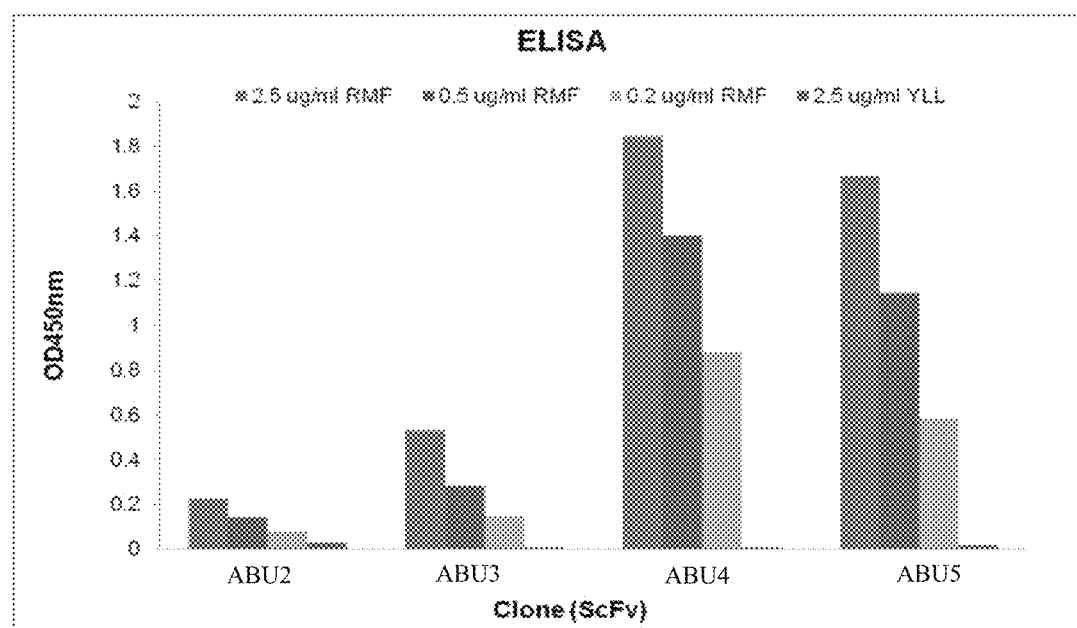
FIG. 5 depicts data from an example ELISA assay.

Affinity maturation was conducted, and resulted in the generation of ABU3, ABU4, and ABU5. ABU3-5 along with ABU2 were assessed for their binding affinity to WT1 peptide (RMF/HLA complex). The data from an example ELISA experiment using either 2.5 μg/ml RMF, 0.5 μg/ml RMF, 0.2 μg/ml RMF, or 2.5 μg/ml YLL is depicted in FIG. 5. As shown in FIG. 5, specificity was retained in all the antigen binding units tested.

Figure 6:
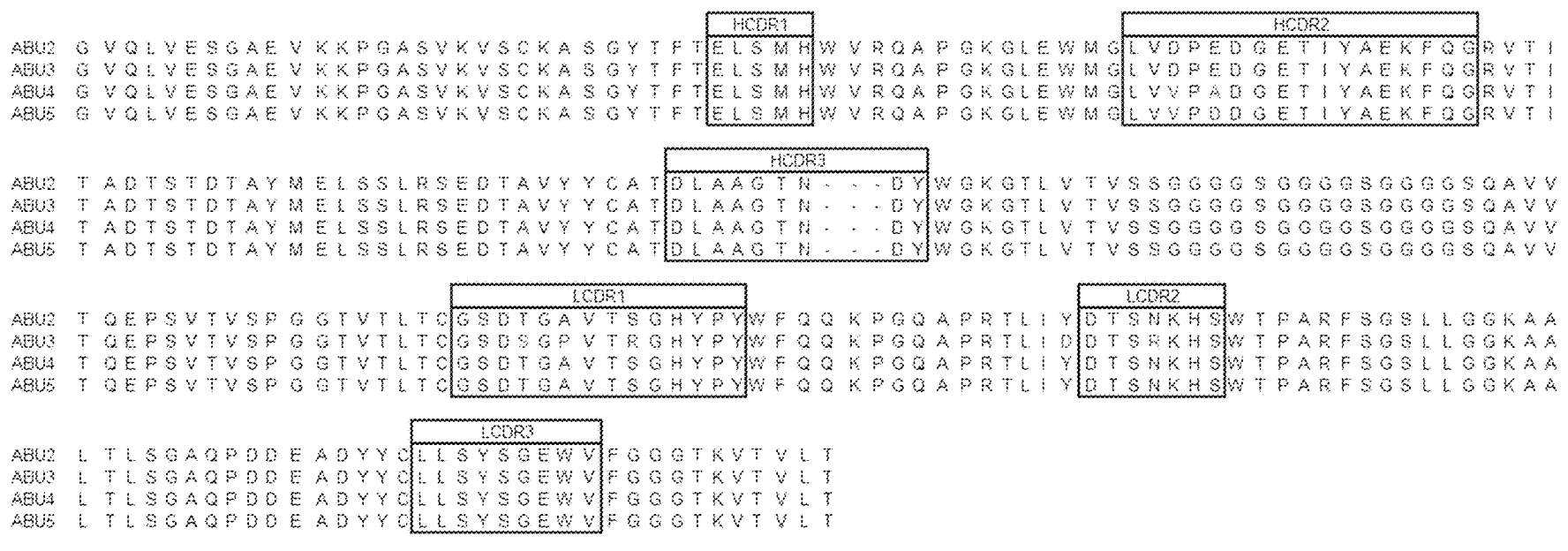

ABU2, ABU3, ABU4, and ABU5 were sequenced and an example alignment of the variable light chain and variable heavy chain regions is depicted in FIG. 6. These regions comprise the heavy chain CDRs HCDR1, HCDR2, and HCDR3, as well as the light chain CDRs LCDR1, LCDR2, and LCDR3.

Example 5: Affinity Assay Using Surface Plasmon Resonance

Figure 7:
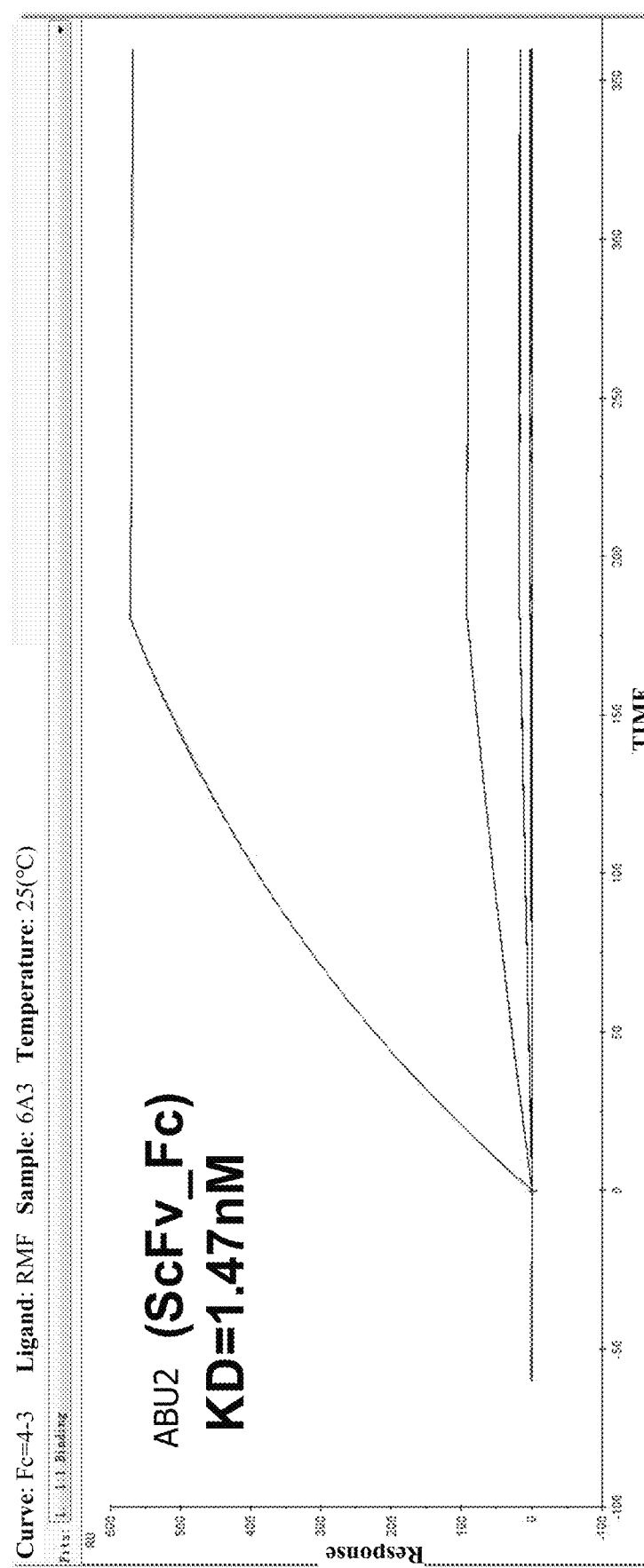
FIG. 7 depicts data from an example $K_D$ experiment.
Figure 7:
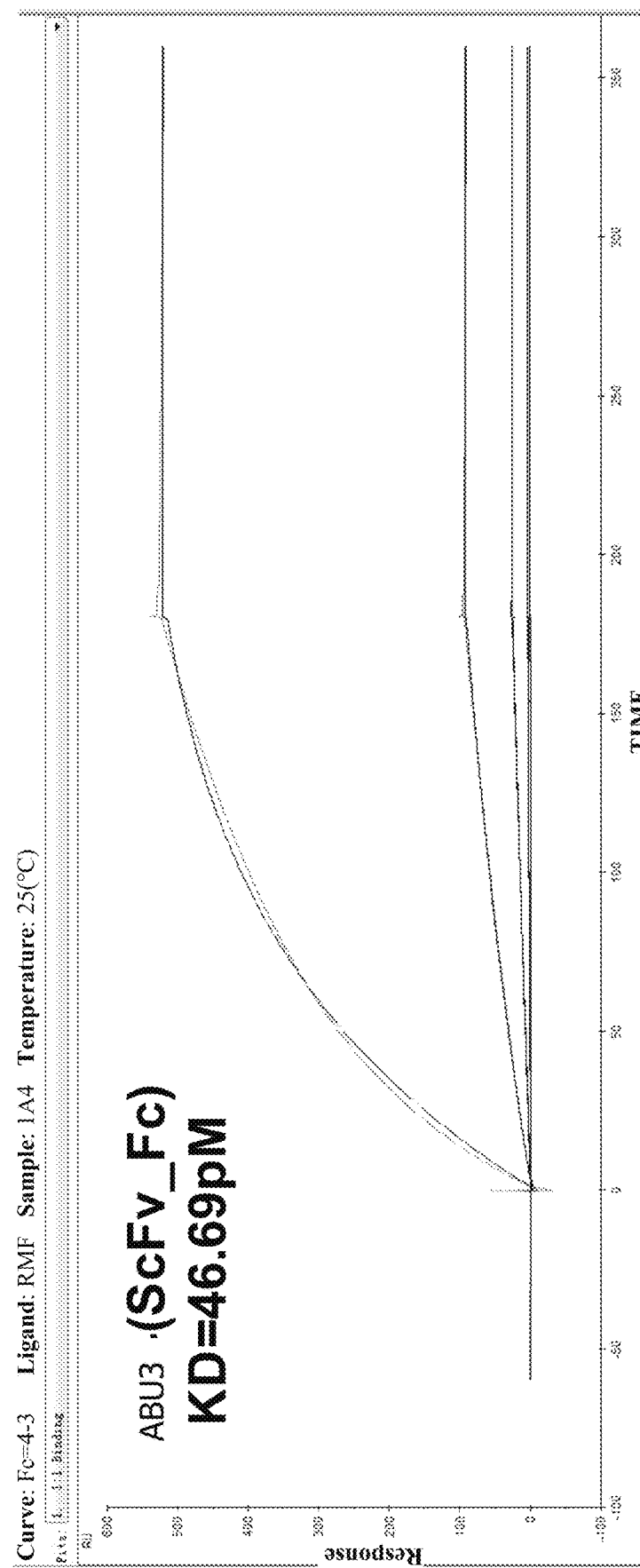

Binding affinity of the affinity matured ABU3 was further assess by surface plasmon resonance (Biacore® T200, BIAcore, Inc) and compared to parent ABU2. The data from an example experiment, analyzed with BIAevaluation3.2 and kinetic curve fitted with 1:1 Langmuir model, are depicted in FIG. 7.

Example 6: Binding Assay of Antibodies to Different Cell Lines Using Frontal Affinity Chromatography (FACs)

Figure 8:
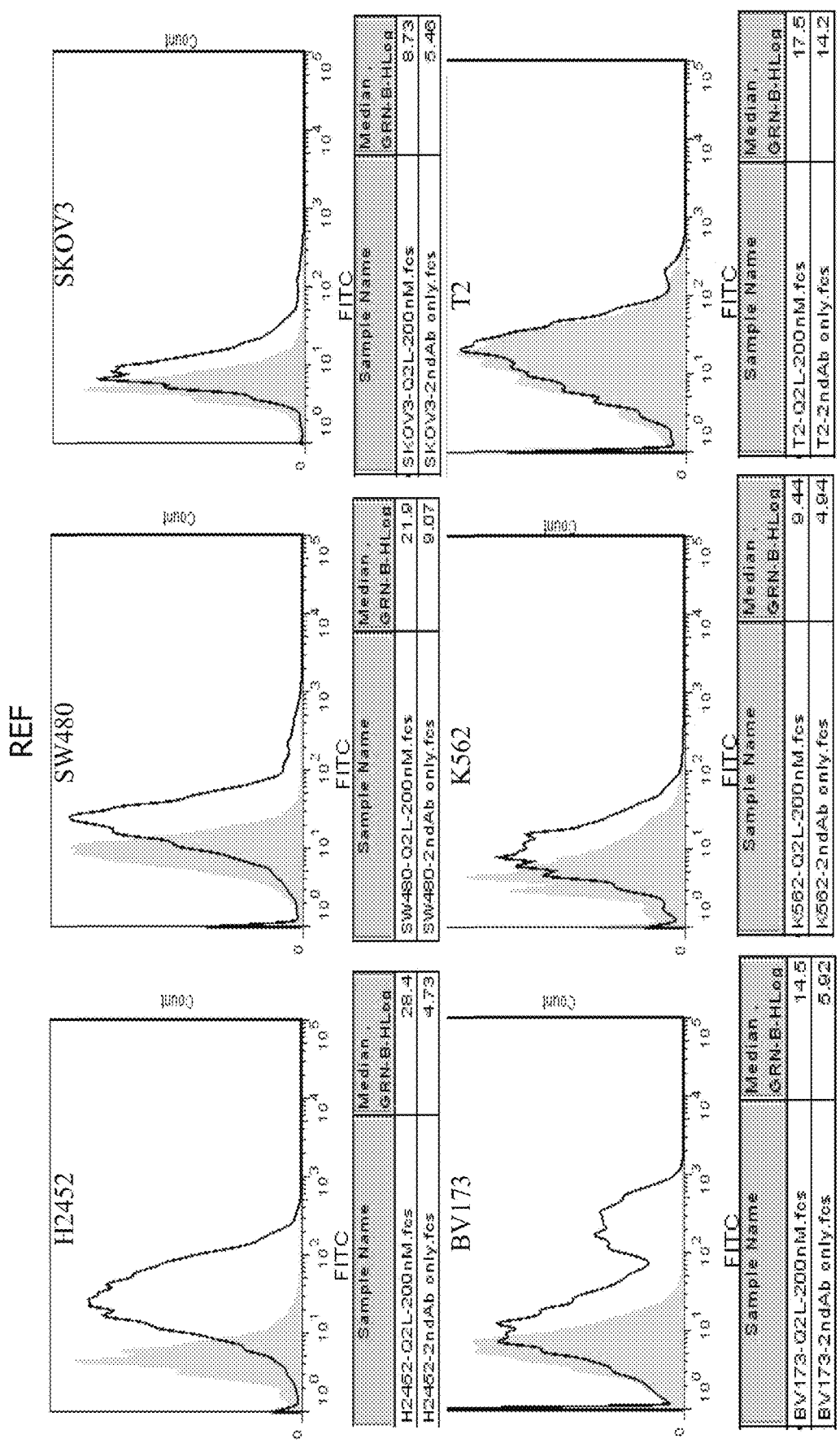
FIG. 8 depicts data from an example binding assay.
Figure 8:
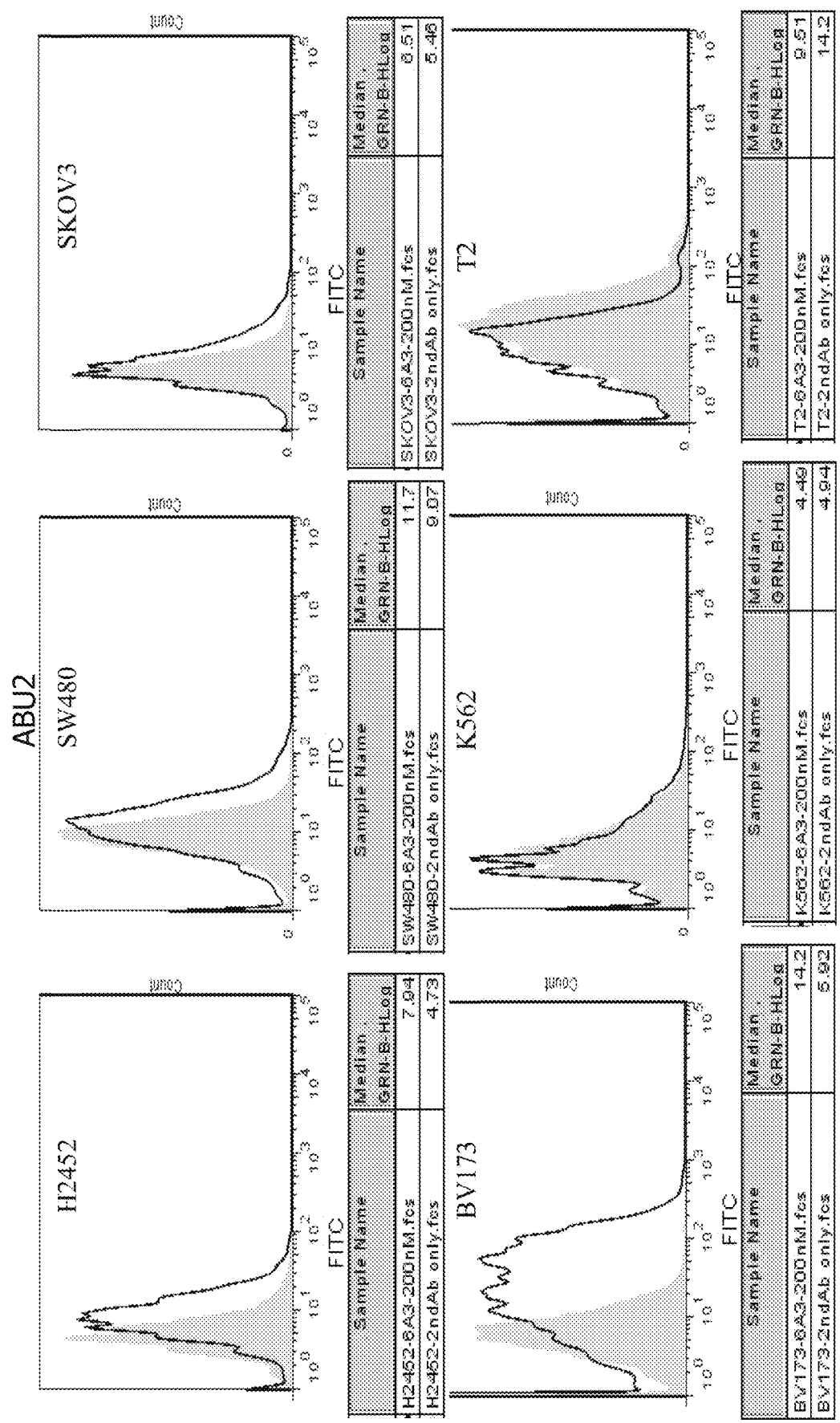
Figure 8:
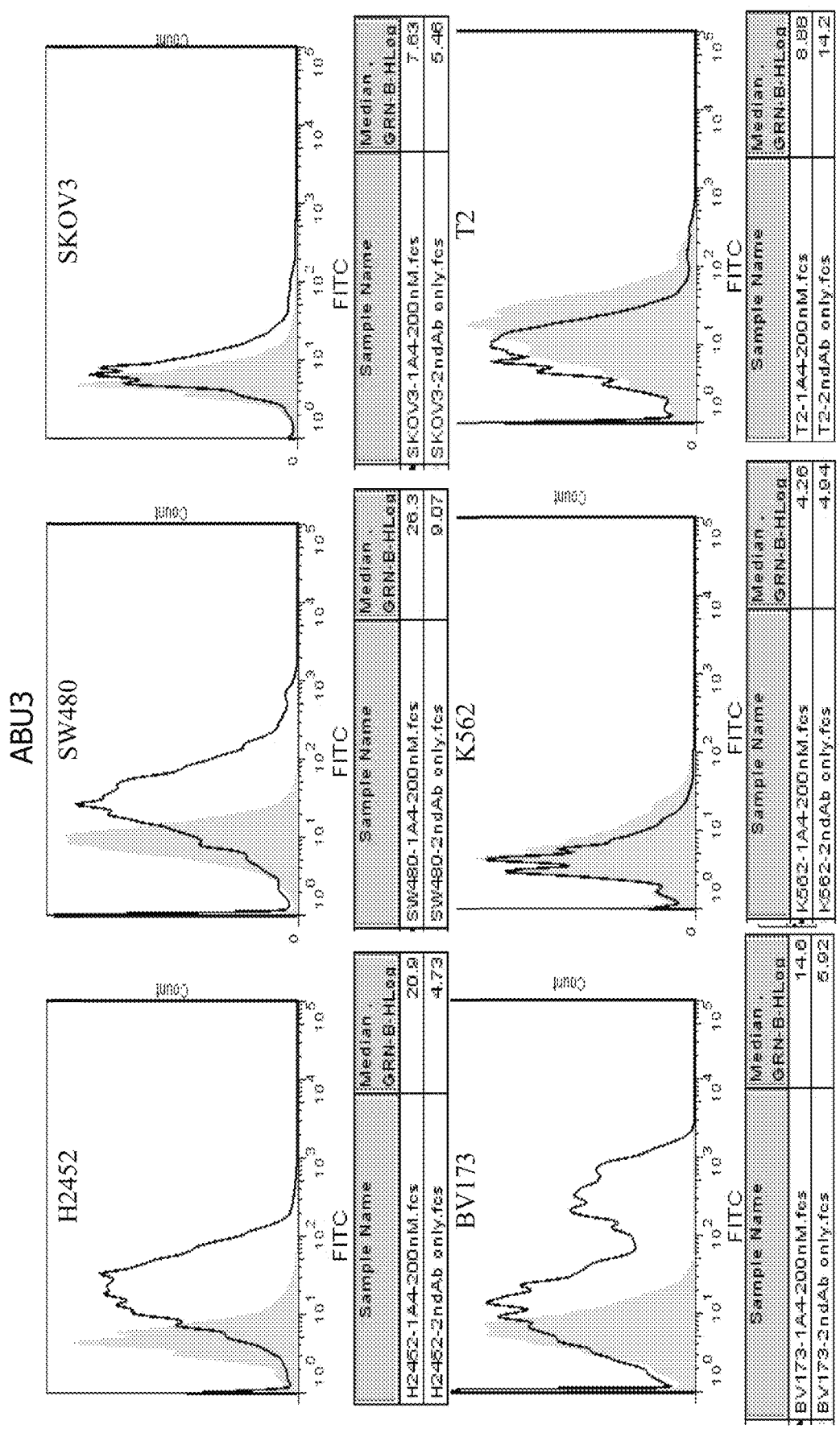
Figure 8:
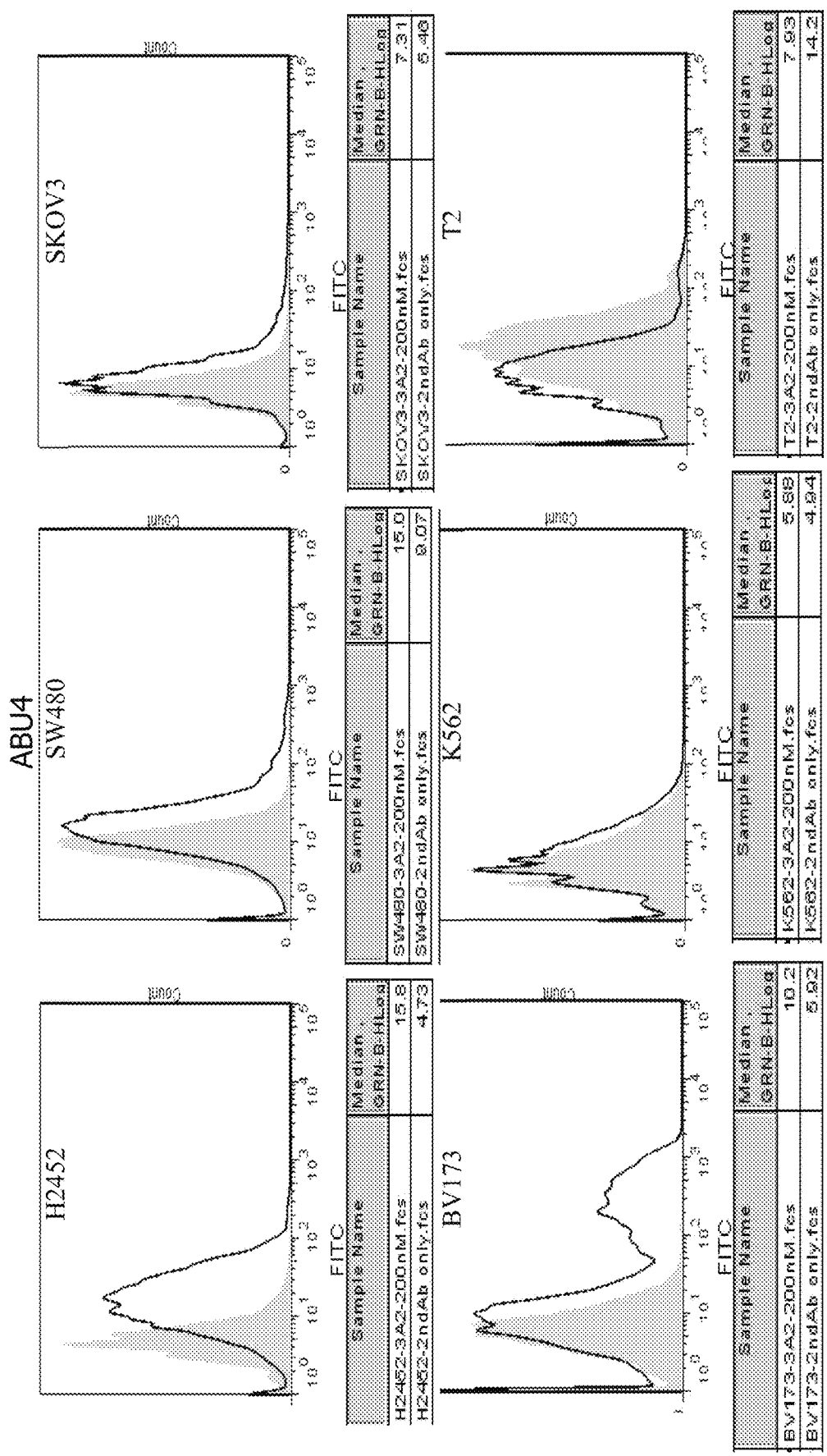
Figure 8:
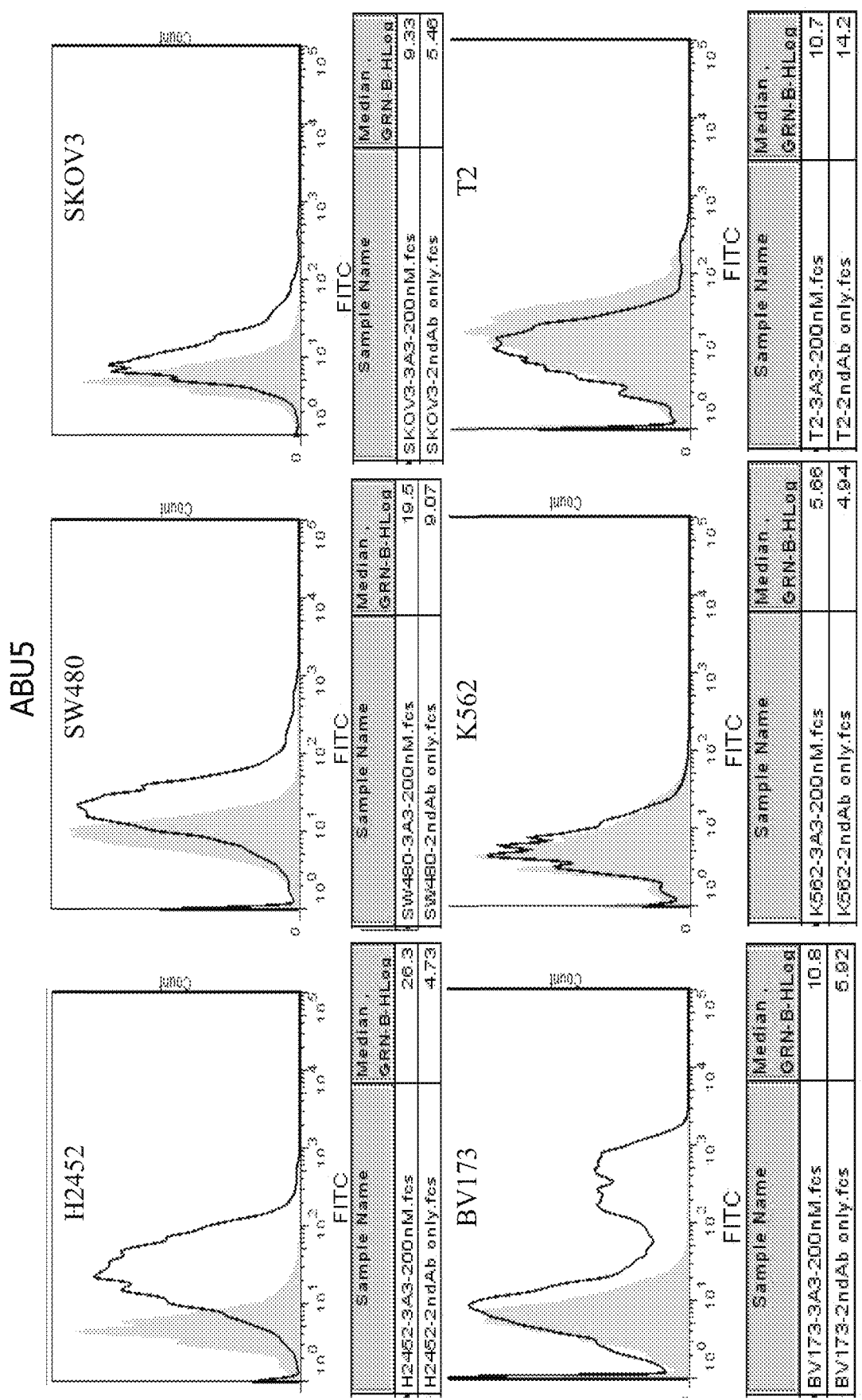

The binding affinities of affinity matures ABU3, ABU4, and ABU5 as well as parental ABU2 were further assed using various cell lines and the results of an example experiment are depicted in FIG. 8.

H2452 is a mesothelioma cell line that is WT1 positive and HLA positive.

SW480 is a colon cancer cell line that is WT1 positive and HLA positive.

SKOV3 is an ovarian cancer cell line that is WT1 positive and HLA positive.

BV173 is a Philadelphia chromosome (Ph1)-positive acute leukemia cell line that is WT1 positive and HLA positive.

K562 is an erythroleukemia cell line that is WT1 positive and HLA negative.

T2 is a somatic cell hybrid cell line that is WT1 negative and HLA positive.

As shown in FIG. 8, REF binds not only to WT1 positive and HLA positive cell lines but also to WT1 positive and HLA negative cell line. In contrast, ABU2-5 binds significantly to WT1 positive and HLA positive cell lines but do not bind to WT1 negative or HLA negative cell lines.

Example 7: ADCC Assay

Antibody-dependent cell-mediated cytotoxicity was determined by lactate dehydrogenase (LDH) release assay using CytoTox 96 (Promega, Madison, USA). NK96 cells stably transfected with CD16a were used as effector cells, and H2452 and SW480 expressing both WT! and HLA-A0201 were used as target cells. ADCC activities of ABU3-5 in the form of Fc-scFv were tested, and calculated as (wherein spon. release stands for spontaneous release):

$$ADCC\% = \frac{\text{Sample release} - \text{target spon. release} - \text{effector spon. release}}{\text{maximum release} - \text{target spon. release}} * 100\%$$

Example 8: Construction of WT1 CAR-T Cells

Lentivirus plasmids expressing various ABU3-based chimeric antigen receptors were cloned using pRRLSINcPPT.EF-1α, comprising pRRLSIN-cPPT.EF-1α-1A4-28Z, pRRLSIN-cPPT.EF-1α-1A4-BBZ, pRRLSIN-cPPT.EF-1α-1A4-28BBZ, pRRLSIN-cPPT.EF-1α-1A4-28Z-F2A-EGFP, pRRLSIN-cPPT.EF-1α-1A4-BBZ-F2A-EGFP, and pRRLSIN-cPPT.EF-1α-1A4-28BBZ-F2A-EGFP. The nucleic acid sequence of ABU3-28Z was constructed to have building blocks encoding a CD8a signaling domain (SEQ ID NO: 35), an ABU3 scFv (SEQ ID NO: 37), and CD8 hinge (SEQ ID NO: 39), a CD28 transmembrane domain (SEQ ID NO: 41), a CD28 intracellular signaling domain (SEQ ID NO: 43) and a CD3Z (SEQ ID NO: 45). The nucleic acid sequence of ABU3-28BBZ was constructed to have building blocks encoding a CD8α signaling domain (SEQ ID NO: 35), an ABU3 scFv (SEQ ID NO: 37), and CD8 hinge (SEQ ID NO: 39), a CD28 transmembrane domain (SEQ ID NO: 41), a CD28 intracellular signaling domain (SEQ ID NO: 43), a CD137 intracellular signaling domain (SEQ ID NO: 49), and a CD3Z (SEQ ID NO: 45). pRRLSIN-cPPT.EF-1α-EGFP was used as control.

The lentivirus plasmids expressing ABU3 CAR were then packaged using pRSV-REV, pMDLg-RRE and VSV-G (Addgene, Cambridge, Mass., USA), and transfected into 293T cells (ATCC: CRL-11268). The transfected cells were grown at 37° C. for 72 h, and supernatant was collected to concentrate the virus. Titration was conducted to determine lentivirus titer. The concentrated lentivirus was then transduced into activated T cells at MOI=15 (32° C., 1,800 rpm). The expression of ABU3-CAR was determined through EGFP by flow cytometry. The transduction efficiency for control and ABU3 CAR (ABU3-28Z, ABU3-BBZ and ABU3-28BBZ) was determined to 68.41%, 58.3%, 70.7%, and 32.6%.

Figure 10A:
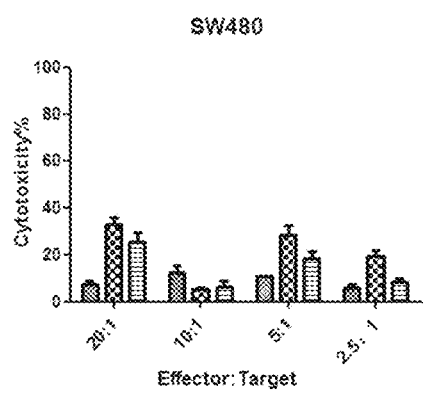
FIG. 10A and FIG. 10B depict data from example cytotoxicity experiments.
Figure 10B:
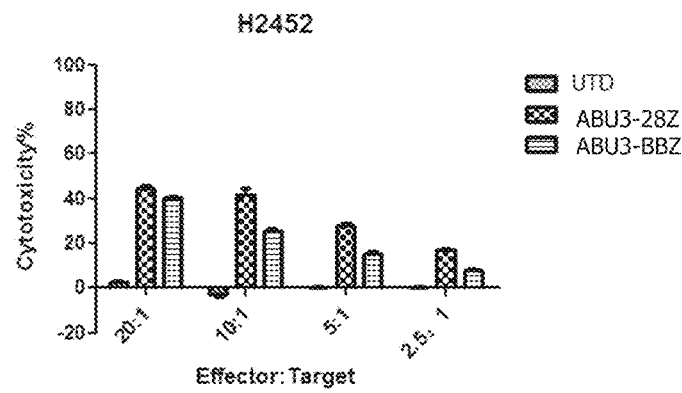

Cytotoxicity was assessed for anti-WT1 CAR T cells ABU3-28Z and ABU3-BBZ and compared to a negative control (UTD). The results of an example experiment are depicted in FIG. 10A and FIG. 10B. H2452 is a mesothelioma cell line that is WT1 positive and HLA positive. SW480 is a colon cancer cell line that is WT1 positive and HLA positive. As shown in FIGS. 10A and 10B, the CAR T cells were confirmed to by cytotoxic against both SW480 and NCI-H2452.

Additional CAR T cells were constructed for ABU2, ABU4, and ABU5, and were confirmed to be cytotoxic against SW480 and NCI-H2452.

Example 9: Bifunctional Antibodies

Figure 9:
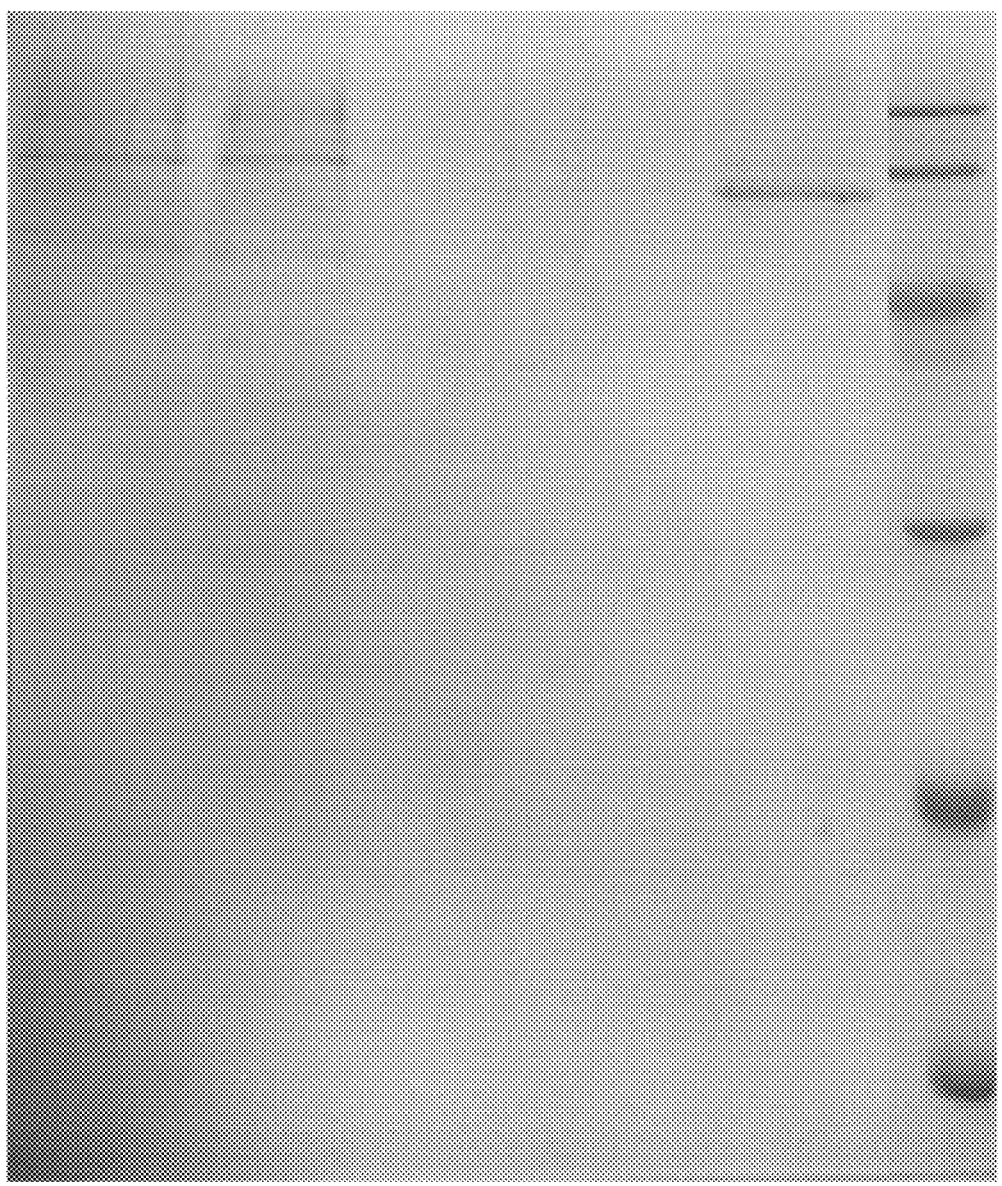
FIG. 9 depicts an example polypeptide purification result.

A bifunctional antibody capable of specifically binding to a WT1 peptide complexed with HLA as well as CD3 was generated (ABU6). Specifically, in a example experiment, Fragment 1 of anti-WT1 scFv (ABU3) was amplified from template (V152-ABU3-huFC plasmid) with forward primer ABU3-PF (SEQ ID NO: 54) and reverse primer ABU3-PR (SEQ ID NO: 55). Fragment 2 of anti-CD3 scFv was amplified from PIH-hu9F2-CD3 plasmid (CN201610626384.7) with primers PCMV (SEQ ID NO: 56) and PH-R (SEQ ID NO: 57). Fragment 1 and Fragment 2 were ligated and amplified with PCMV and ABU3-PR. Digestion of the resulted scFv with BamHI/NheI and insertion into digested PIH-hu9F2-CD3 plasmid yielded a bifunctional scFv (SEQ ID NO: 63). The six consecutive His at C terminal allows it to be purified by Ni-NTA affinity chromatography. The bifunctional scFv was then transfected into 293F cells, and purified by Ni-NTA affinity chromatography. SDS PAGE results were shown in FIG. 9, WT1/CD3 bifunctional scFv was shown as a band at around 55 kDa.

Example 10: WT CAR-T Cells Expressing IL-12

ABU3-28Z-IL12 CAR vector as shown in FIG. 11 was constructed according to a similar method to Examples 8-9. PCR amplification of ABU3 (SEQ ID NO: 37), CD28 transmembrane domain (SEQ ID NO: 41) and intracellular domain (SEQ ID NO: 43), CD3Z (SEQ ID NO: 35), and EGFP (SEQ ID NO: 78) were conducted to provide ABU3-28Z-GFP fragment, which was then inserted into pRRLSIN vector via enzymatic cleavage to provide ABU3-28Z-GFP CAR vector. The IL-2 promotor sequence (SEQ ID NO: 77), and the IL-12 gene sequence (SEQ ID NO: 76) were amplified via PCT to provide IL2-IL12 sequence, which was then inserted into pRRLSIN vector to provide ABU3-28Z-IL12 CAR vector. VRRLSIN-ABU3-28Z-IL12 lentivirus was packaged. T cells were activated and transduced with the lentivirus, to provide ABU3-28Z-IL12 CAR T cells.

Figure 12A:
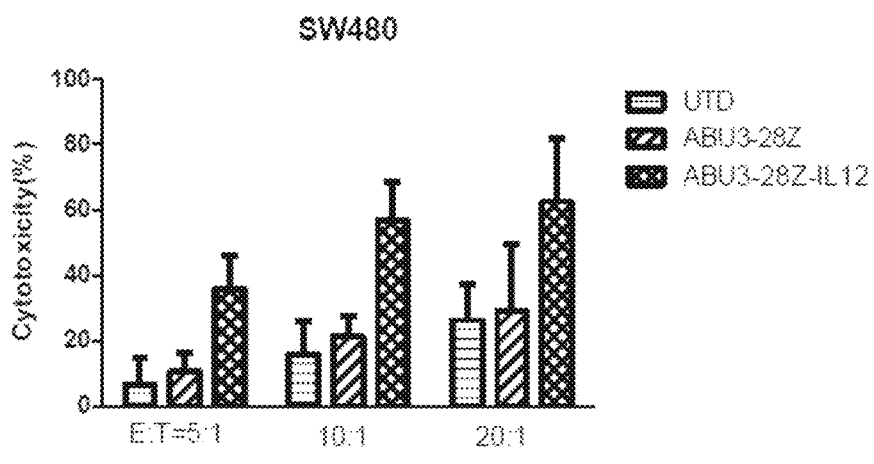
FIG. 12A, FIG. 12B and FIG. 12C depict data from an example cytotoxicity experiment using CAR T-cells expressing IL-12.
Figure 12B:
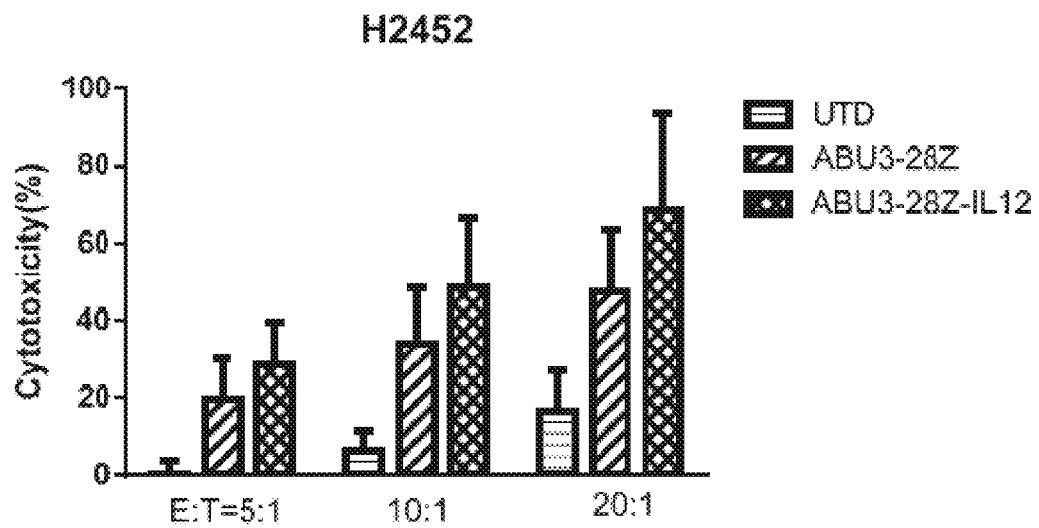
Figure 12C:
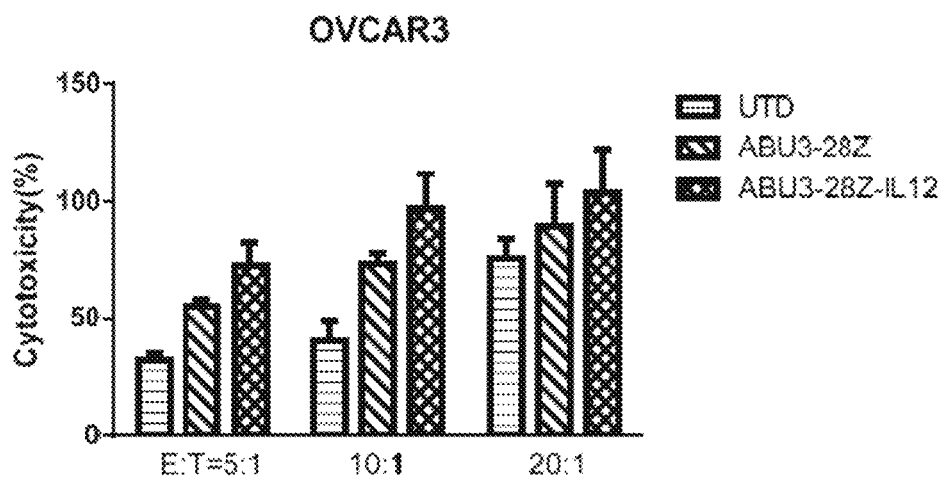

Human colon cancer cell line SW480, human mesothelioma cell line H2452 and ovarian cancer cell line OVCAR3 were used as target cells to determine the in vitro cell killing effect of ABU3-28Z-IL12 CART cells. CART cells were added at an effector:target (E:T) ratio of 20:1, 10:1 and 5:1, respectively, and cultured in vitro for 18 hours. CytoTox 96® Non-Radioactive Cytotoxicity Assay Kits were used and results are shown in FIGS. 12A-C. For each E:T ratio tested, the ABU3-28Z-IL-12 CAR-T cells have a greater cytotoxicity than ABU3-28Z CAR-Tcells and UTD cells.

TABLE 8

| SEQ ID NO: | Sequence |
|---|---|
| 1 | RMFPNAPYL |
| 2 | SYAIS |
| 3 | GIIPIFGTANYAQKFQG |
| 4 | GGSSGWYNWFDP |
| 5 | RASQIVMSNFLA |
| 6 | GASRRVT |
| 7 | QQYGSSPT |
| 8 | ELSMH |

TABLE 8-continued

Sequences

| SEQ ID NO: | Sequence |
|---|---|
| 9 | LVDPEDGETIYAEKFQG |
| 10 | DLAAGTNDY |
| 11 | GSDTGAVTSGHYPY |
| 12 | DTSNKHS |
| 13 | LLSYSGEWV |
| 14 | GSDSGPVTRGHYPY |
| 15 | DTSRKHS |
| 16 | LVVPADGETIYAEKFQG |
| 17 | LVVPDDGETIYAEKFQG |
| 18 | QVQLVQSGAEVKKPGSSVKVSCKASGGTFSSYAISWVRQAPGQGLEWMGGIIPIFGTANYA QKFQGRVTITADESTSTAYMELSSLRSEDTAVYYCARGGSSGWYNWFDPWGRGTLVTVSS |
| 19 | CAGGTGCAGCTGGTGCAGTCTGGGGCTGAGGTGAAGAAGCCTGGGTCCTCGGTGAAGG TCTCCTGCAAGGCTTCTGGAGGCACCTTCAGCAGCTATGCTATCAGCTGGGTGCGACAG GCCCCTGGACAAGGGCTTGAGTGGATGGGAGGGATCATCCCTATCTTTGGTACAGCAAA CTACGCACAGAAGTTCCAGGGCAGAGTCACGATTACCGCGGACGAATCCACGAGCACA GCCTACATGGAGCTGAGCAGCCTGAGATCTGAGGACACGGCCGTGTATTACTGTGCGAG AGGAGGTAGCAGTGGCTGGTACAACTGGTTCGACCCCTGGGGCAGAGGAACCCTGGTC ACCGTCTCGAGT |
| 20 | GVQLVESGAEVKKPGASVKVSCKASGYTFTELSMHWVRQAPGKGLEWMGLVDPEDGETI YAEKFQGRVTITADTSTDTAYMELSSLRSEDTAVYYCATDLAAGTNDYWGKGTLVTVSS |
| 21 | GGGGTGCAGCTGGTGGAGTCCGGGGCTGAGGTGAAGAAGCCTGGGGCCTCAGTGAAGG TCTCCTGCAAGGCTTCTGGATACACCTTCACTGAATTATCCATGCACTGGGTGCGACAG GCTCCTGGAAAAGGGCTTGAGTGGATGGGACTTGTTGATCCTGAAGATGGTGAAACAAT ATACGCAGAGAAGTTCCAGGGCAGAGTCACCATAACCGCGGACACGTCTACAGACACA GCCTACATGGAGCTGAGCAGCCTGAGATCTGAGGACACGGCCGTGTATTACTGTGCTAC AGACCTAGCAGCTGGTACTAATGACTACTGGGGCAAAGGCACCCTGGTCACCGTCTCGA GT |
| 22 | GVQLVESGAEVKKPGASVKVSCKASGYTFTELSMHWVRQAPGKGLEWMGLVVPADGETI YAEKFQGRVTITADTSTDTAYMELSSLRSEDTAVYYCATDLAAGTNDYWGKGTLVTVSS |
| 23 | GGGGTGCAGCTGGTGGAGTCCGGGGCTGAGGTGAAGAAGCCTGGGGCCTCAGTGAAGG TCTCCTGCAAGGCTTCTGGATACACCTTCACTGAATTATCCATGCACTGGGTGCGACAG GCTCCTGGAAAAGGGCTTGAGTGGATGGGACTTGTTGTACCTGCCGACGGTGAAACAAT TTACGCAGAGAAGTTCCAGGGCAGAGTCACCATAACCGCGGACACGTCTACAGACACA GCCTACATGGAGCTGAGCAGCCTGAGATCTGAGGACACGGCCGTGTATTACTGTGCTAC AGACCTAGCAGCTGGTACTAATGACTACTGGGGCAAAGGCACCCTGGTCACCGTCTCGA GT |
| 24 | GVQLVESGAEVKKPGASVKVSCKASGYTFTELSMHWVRQAPGKGLEWMGLVVPDDGETI YAEKFQGRVTITADTSTDTAYMELSSLRSEDTAVYYCATDLAAGTNDYWGKGTLVTVSS |
| 25 | GGGGTGCAGCTGGTGGAGTCCGGGGCTGAGGTGAAGAAGCCTGGGGCCTCAGTGAAGG TCTCCTGCAAGGCTTCTGGATACACCTTCACTGAATTATCCATGCACTGGGTGCGACAG GCTCCTGGAAAAGGGCTTGAGTGGATGGGACTAGTTGTTCCTGATGATGGTGAAACAAT ATACGCAGAGAAGTTCCAGGGCAGAGTCACCATAACCGCGGACACGTCTACAGACACA GCCTACATGGAGCTGAGCAGCCTGAGATCTGAGGACACGGCCGTGTATTACTGTGCTAC AGACCTAGCAGCTGGTACTAATGACTACTGGGGCAAAGGCACCCTGGTCACCGTCTCGA GT |
| 26 | EIVMTQSPGTLSLSPGERATLSCRASQIVMSNFLAWYQQKPGQAPRLLIYGASRRVTGIPDRF SGSGSGTDFSLIISRLEPEDFAVYYCQQYGSSPTFGQGTKVEIKR |
| 27 | GAAATTGTGATGACACAGTCTCCAGGCACCCTGTCTTTGTCTCCAGGGGAAAGGGCCAC CCTCTCCTGCAGGGCCAGTCAGATTGTTATGAGCAACTTCTTAGCCTGGTACCAGCAGA AACCTGGCCAGGCTCCCAGGCTCCTCATCTATGGTGCATCCAGGAGGGTCACTGGCATC CCAGACAGGTTCAGTGGCAGTGGGTCTGGGACAGACTTCAGTCTCATCATCAGCAGACT GGAGCCTGAAGATTTTGCAGTGTATTACTGTCAGCAATATGGTAGCTCACCGACGTTCG GCCAAGGGACCAAGGTGGAAATCAAACGT |
| 28 | QAVVTQEPSVTVSPGGTVTLTCGSDTGAVTSGHYPYWFQQKPGQAPRTLIYDTSNKHSWTP ARFSGSLLGGKAALTLSGAQPDDEADYYCLLSYSGEWVFGGGTKVTVL |

TABLE 8-continued

Sequences

| SEQ ID NO: | Sequence |
|---|---|
| 29 | CAGGCTGTGGTGACTCAGGAGCCCTCAGTGACTGTGTCCCCAGGAGGGACAGTCACTCT<br>CACCTGTGGCTCCGACACTGGAGCTGTCACCAGTGGTCATTATCCCTACTGGTTCCAGC<br>AGAAGCCTGGCCAAGCCCCCAGGACACTGATTTATGATACAAGCAACAAACACTCCTG<br>GACACCTGCCCGGTTCTCAGGCTCCCTCCTTGGGGGCAAAGCTGCCCTGACCCTTTCGG<br>GTGCGCAGCCTGACGATGAGGCTGACTATTACTGCTTGCTCTCCTATAGTGGTGAATGG<br>GTGTTCGGCGGAGGGACCAAAGTCACCGTCCTA |
| 30 | QAVVTQEPSVTVSPGGTVTLTCGSDSGPVTRGHYPYWFQQKPGQAPRTLIDDTSRKHSWTP<br>ARFSGSLLGGKAALTLSGAQPDDEADYYCLLSYSGEWVFGGGTKVTVL |
| 31 | CAGGCTGTGGTGACTCAGGAGCCCTCAGTGACTGTGTCCCCAGGAGGGACAGTCACTCT<br>CACCTGTGGCTCCGACTCTGGACCGGTCACCCGAGGGCATTACCCCTACTGGTTCCAGC<br>AGAAGCCTGGCCAAGCCCCCAGGACACTGATTGATGATACAAGCCGCAAACACTCCTG<br>GACACCTGCCCGGTTCTCAGGCTCCCTCCTTGGGGGCAAAGCTGCCCTGACCCTTTCGG<br>GTGCGCAGCCTGACGATGAGGCTGACTATTACTGCTTGCTCTCCTATAGTGGCGAATGG<br>GTGTTCGGCGGAGGGACCAAAGTCACCGTCCTA |
| 32 | ATACATATGGGTAGCCATAGCATGCGCTATTTTTTCACCAGCGTTAGCCGTCCGGGTCGT<br>GGTGAACCGCGTTTTATTGCAGTTGGTTATGTTGATGATACCCAGTTTGTGCGCTTTGAT<br>AGTGATGCAGCAAGCCAGCGTATGGAACCGCGTGCACCGTGGATTGAACAAGAAGGTC<br>CGGAATATTGGGATGGTGAAACCCGTAAAGTTAAAGCACATAGCCAGACCCATCGTGTT<br>GATCTGGGCACCCTGCGTGGCTATTATAACCAGAGCGAAGCAGGTTCACATACCGTTCA<br>GCGTATGTATGGTTGTGATGTTGGTAGCGATTGGCGTTTTCTGCGTGGTTATCATCAGTA<br>TGCCTATGATGGCAAAGATTATATCGCCCTGAAAGAAGATCTGCGTAGCTGGACCGCAG<br>CAGATATGGCAGCACAGACCACCAAACATAAATGGGAAGCAGCACATGTTGCAGAACA<br>GCTGCGTGCATATCTGGAAGGCACCTGTGTTAATGGCTGCGTCGTTATCTGGAAAATG<br>GTAAAGAAACCCTGCAGCGTACCGATGCACCGAAAACCCACATGACCCATCATGCAGT<br>TAGCGATCATGAAGCAACCCTGCGTTGTTGGGCACTGAGCTTTTATCCGGCAGAAATCA<br>CCCTGACCTGGCAGCGTGATGGTGAAGATCAGACCCAGGATACCGAACTGGTTGAAAC<br>ACGTCCTGCCGGTGATGGCACCTTTCAGAAATGGGCAGCAGTTGTTGTTCCGAGCGGTC<br>AAGAACAGCGTTATACCTGTCATGTTCAGCATGAAGGTCTGCCGAAACCGCTGACCCTG<br>CGCTGGGAAGGTAGCGGTCTGAATGATATTTTTGAAGCCCAGAAAATCGAATGGCACG<br>AGTAATAAGGATCCGCGC |
| 33 | ATATCCATATGATTCAGCGTACCCCGAAAATTCAGGTTTATAGCCGTCATCCGGCAGAA<br>AATGGTAAAGCAATTTTCTGAATTGCTACGTGAGCGGTTTTCATCCGAGCGATTTGA<br>AGTTGATCTGCTGAAAAATGGCGAACGCATTGAAAAAGTTGAACATAGCGATCTGAGC<br>TTTAGCAAAGATTGGAGCTTTTATCTGCTGTACATACCGAATTTACCCCGACCGAAAA<br>AGATGAATATGCCTGTCGTGTTAATCATGTTACCCTGAGCCAGCCGAAAATTGTTAAAT<br>GGGATCGTGATATGTAATAAGGATCCAGTCG |
| 34 | GSHSMRYFFTSVSRPGRGEPRFIAVGYVDDTQFVRFDSDAASQRMEPRAPWIEQEGPEYWD<br>GETRKVKAHSQTHRVDLGTLRGYYNQSEAGSHTVQRMYGCDVGSDWRFLRGYHQYAYD<br>GKDYIALKEDLRSWTAADMAAQTTKHKWEAAHVAEQLRAYLEGTCVEWLRRYLENGKE<br>TLQRTDAPKTHMTHHAVSDHEATLRCWALSFYPAEITLTWQRDGEDQTQDTELVETRPAG<br>DGTFQKWAAVVVPSGQEQRYTCHVQHEGLPKPLTLRWE |
| 35 | Atggccttaccagtgaccgccttgctcctgccgctggccttgctgctccacgccgccaggccg |
| 36 | MALPVTALLLPLALLLHAARP |
| 37 | Ggggtgcagctggtggagtccggggctgaggtgaagaagcctggggcctcagtgaaggtctcc<br>tgcaaggcttctggatacaccttcactgaattatccatgcactgggtgcgacaggcctcctgga<br>aaagggcttgagtggatgggacttgttgatcctgaagatggtgaaacaatatacgcagagaag<br>ttccaggcagagtcaccataaccgcggacacgtctacagacacagcctacatggagctgagc<br>agcctgagatctgaggacacggccgtgtattactgtgctacagacctagcagctggtactaat<br>gactactggggcaaaggcaccctggtcaccgtctcgagtggtggaggcggttcaggcggaggt<br>ggttctggcggtggcggatcgcaggctgtggtgactcaggagccctcagtgactgtgtcccca<br>ggagggacagtcactctcacctgtggctccgactctggaccggtcacccgagggcattaccccc<br>tactggttccagcagaagcctggccaagcccccaggacactgattgatgatacaagccgcaaa<br>cactcctggacacctgcccggttctcaggctccctccttgggggcaaagctgccctgacccttc<br>tcgggtgcgcagcctgacgatgaggctgactattactgcttgctctcctatagtggcgaatgg<br>gtgttcggcggagggaccaaagtcaccgtccta |
| 38 | gvqlvesgaevkkpgasvkvsckasgytftelsmhwvrqapgkglewmglvdpedgetiyaek<br>fqgrvtitadtstdtaymelsslrsedtavyycatdlaagtndywgkgtlvtvssggggsggg<br>gsggggsqavvtqepsvtvspggtvtltcgsdsgpvtrghypywfqqkpgqaprtliddtsrk<br>hswtparfsgsllggkaaltlsgaqpddeadyycllsysgewvfgggtkvtvl |
| 39 | Accacgacgccagccgccgccaccaacaccggcgccaccatcgcgtcgcagcccctgtcc<br>ctgcgcccagaggcgtgccggccagc<br>ggcggggggcgcagtgcacacgaggggctggacttcgcctgtgat |
| 40 | TTTPAPRPPTPAPTIASQPLSLRPEACRPAAGGAVHTRGLDFACD |

TABLE 8-continued

Sequences

| SEQ ID NO: | Sequence |
|---|---|
| 41 | Ttttgggtgctggtggtggttggtggagtcctggcttgctatagcttgctagtaacagtggcctttattattttctgggtg |
| 42 | FWVLVVVGGVLACYSLLVTVAFIIFWV |
| 43 | Aggagtaagaggagcaggctcctgcacagtgactacatgaacatgactcccgccgcccgggccaacccgcaagcattaccagccctatgccccaccacgcgacttcgcagcctatcgctcc |
| 44 | RSKRSRLLHSDYMNMTPRRPGPTRKHYQPYAPPRDFAAYRS |
| 45 | Agagtgaagttcagcaggagcgcagacgccccgcgtaccagcagggccagaaccagctctataacgagctcaatctaggacgaagagaggagtacgatgttttggacaagagacgtggccgggaccctgagatggggggaaagccgcagagaaggaagaaccctcaggaaggcctgtacaatgaactgcagaaagataagatggcggaggcctacagtgagattgggatgaaaggcgagcgccggaggggcaaggggcacgatggcctttaccagggtctcagtacagccaccaaggacacctacgacgccttcacatgcaggccctgcccctcgc |
| 46 | RVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR |
| 47 | Atctacatctgggcgcccttggccgggacttgtggggtccttctcctgtcactggttatcacc |
| 48 | IYIWAPLAGTCGVLLLSLVIT |
| 49 | Aaacggggcagaaagaaactcctgtatatattcaaacaaccatttatgagaccagtacaaactactcaagaggaagatggctgtagctgccgatttccagaagaagaagaaggaggatgtgaactg |
| 50 | KRGRKKLLYIFKQPFMRPVQTTQEEDGCSCRFPEEEEGGCEL |
| 51 | ggggtgcagctggtggagtccggggctgaggtgaagaagcctggggcctcagtgaaggtctcctgcaaggcttctggatacaccttcactgaattatccatgcactgggtgcgacaggctcctggaaaagggcttgagtgatgggactagttgttcctgatgatggtgaaacaatatacgcagagaagttccaggcagagtcaccataaccgcggacacgtctacagacacagcctacatggagctgagcagcctgagatctgaggacacggccgtgtattactgtgctacagacctagcagctggtactaatgactactggggcaaaggcaccctggtcaccgtctcgagtggtggaggcggttcaggcggaggtggtctggcggtggcggatcgcaggctggtgactcaggacccctcagtgactgtgtcccaggaggacagtcactctcacctgtggctccgacactggagctgtcaccagtggtcattatccctactggttccagcagaagcctggccaagcccccaggacactgatttatgatacaagcaacaaacactcctggacacctgcccggttctcaggctccctccttgggggcaaagctgccctgaccctttcgggtgcgcagcctgacgatgaggctgactattactgcttgctctcctatagtggtgaatgggtgttcggcggagggaccaaagtcaccgtccta |
| 52 | Gvqlvesgaevkkpgasvkvsckasgytftelsmhwvrqapgkglewmglvvpddgetiyaekfqgrvtitadtstdtaymelsslrsedtavyycatdlaagtndywgkgtivtvssggggsgggggsggggsqavvtqepsvtvspggtvtltcgsdtgavtsghypywfqqkpgqaprtliydtsnkhswtparfsgsllggkaaltlsgaqpddeadyycllsysgewvfgggtkvtvl |
| 53 | GGGGSGGGGSGGGGS |
| 54 | GCTTTGGTTTCCAGGTGCAAGATGTGGGGTGCAGCTGGTGGAGT |
| 55 | GATATCGGATCCACCACCTCCTAGGACGGTGACTTTGGTCC |
| 56 | GGCTAACTAGAGAACCCACTGC |
| 57 | ACATCTTGCACCTGGAAACCAAAGC |
| 58 | RMFPTPPSL |
| 59 | RMFPGEVAL |
| 60 | Evqllesggglvqpggslrlscaasgftfssyamswvrqapgkglewvslidpwgqetlyadsvkgrftisrdnskntlylqmnslraedtavyycakltgrfdywgqgtlvtvssggggsggggsggggsdiqmtqspsslsasvgdrvtitcrasqsissylnwyqqkpgkapklliysasllqsgvpsrfsgsgsgtdftltisslqpedfatyycqqgpgtpntfgqgtkveikr |
| 61 | RSKRSRLLHSDYMNMTPRRPGPTRKHYQPYAPPRDFAAYRSRVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR |
| 62 | KRGRKKLLYIFKQPFMRPVQTTQEEDGCSCRFPEEEEGGCELRVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR |

TABLE 8-continued

Sequences

| SEQ ID NO: | Sequence |
|---|---|
| 63 | Gvqlvesgaevkkpgasvkvsckasgytftelsmhwvrqapgkglewmglvdpedgetiyaek
fqgrvtitadtstdtaymelsslrsedtavyycatdlaagtndywgkgtlvtvssggggsggg
gsggggsqavvtqepsvtvspggtvtltcgsdsgpvtrghypywfqqkpgqaprtliddtsrk
hswtparfsgsllggkaaltlsgaqpddeadyycllsysgewvfgggtkvtvlggggsdiklq
qsgaelarpgasvkmsckctsgytfrtrytmhwvkqrpgqglewigyinpsrgytnynqkfkdka
tladkssstaymqlssltsedsavyycaryyddhycldywgqgttltvssveggsgggsggg
sggvddiqltqspaimsaspgekvtmtcrasssysymnwyqqksgtspkrwiydtskvasgvp
yrfsgsgsgtsysltissmeaedaatyycqqwssnpltfgagtklelkhhhhhh |
| 64 | ggggtgcagctggtggagtccggggctgaggtgaagaagcctggggcctcagtgaaggtctcc
tgcaaggcttctggatacaccttcactgaattatccatgcactgggtgcgacaggctcctgga
aaagggcttgagtggatgggacttgttgatcctgaagatggtgaaacaatatacgcagaagag
ttccagggcagagtcaccataaccgcggacacgtctacagacacagcctacatggagctgagc
agcctgagatctgaggacacggccgtgtattactgtgctacagacctagcagctggtactaat
gactactgggcaaaggcaccctggtcaccgtctcgagtggtggaggcggttcaggcggaggt
ggttctggcggtggcggatcgcaggctgtggtgactcaggagccctcagtgactgtgtcccca
ggagggacagtcactctcacctgtggctccgactctggaccggtcacccgagggcattacccc
tactggttccagcagaagcctggccaagcccccaggacactgattgatgatacaagccgcaaa
cactcctggacacctgcccggttctcaggctccctccttgggggcaaagctgccctgaccctt
tcgggtgcgcagcctgacgatgaggctgactattactgcttgctctcctatagtggcgaagg
gtgttcggcggagggaccaaagtcaccgtcctaggaggtggtggatccgatatcaaactgcag
cagtcaggggctgaactggcaagacctggggcctcagtgaagatgtcctgcaagacttctggc
tacacctttactaggtacacgatgcactgggtaaaacagaggcctggacagggtctggaatgg
attggatacattaatcctagccgtggttatactaattacaatcagaagttcaaggacaaggcc
acattgactacagacaaatcctccagcacagcctacatgcaactgagcagcctgacatctgag
gactctgcagtctattactgtgcaagatattatgatgatcattactgccttgactactgggc
caaggcaccactctcacagtctcctcagtcgaaggtggaagtggaggttctggtggaagtgga
ggttcaggtggagtcgacgacattcagctgacccagtctccagcaatcatgtctgcatctcca
ggggagaaggtcaccatgacctgcagagccagttcaagtgtaagttacatgaactggtaccag
cagaagtcaggcacctcccccaaaagatggatttatgacacatccaaagtggcttctggagtc
ccttatcgcttcagtggcagtgggtctgggacctcatactctctcacaatcagcagcatggag
gctgaagatgctgccacttattactgccaacagtggagtagtaacccgctcacgttcggtgct
gggaccaagctggagctgaaacatcatcaccatcatcat |
| 65 | YLLEMLWRL |
| 66 | RskrsrllhsdymnmtprrpgptrkhyqpyapprdfaayrsKrgrkkllyifkqpfmrpvqtt
qeedgcscrfpeeeeggcelrvkfsrsadapayqqgqnqlynelnlgrreeydvldkrrgrdp
emggkpqrrknpqeglynelqkdkmaeayseigmkgeragkghdglyqglstatkdtydalhm
qalppr |
| 67 | GVQLVESGAEVKKPGASVKVSCKASGYTFTELSMHWVRQAPGKGLEWMGLVDPEDGETI
YAEKFQGRVTITADTSTDTAYMELSSLRSEDTAVYYCATDLAAGTNDYWGKGTLVTVSSG
GGGSGGGGSGGGGSQAVVTQEPSVTVSPGGTVTLTCGSDSGPVTRGHYPYWFQQKPGQAP
RTLIDDTSRKHSWTPARFSGSLLGGKAALTLSGAQPDDEADYYCLLSYSGEWVFGGGTKVT
VLTttpaprpptpaptiasqplslrpeacrpaaggavhtrgldfacdFwvlvvvggvlacysl
lvtvafiifwvRskrsrllhsdymnmtprrpgptrkhyqpyapprdfaayrsvkfsrsadap
ayqqgqnqlynelnlgrreeydvldkrrgrdpemggkpqrrknpqeglynelqkdk
maeayseigmkgerrrgkghdglyqglstatkdtydalhmqalppr |
| 68 | GVQLVESGAEVKKPGASVKVSCKASGYTFTELSMHWVRQAPGKGLEWMGLVDPEDGETI
YAEKFQGRVTITADTSTDTAYMELSSLRSEDTAVYYCATDLAAGTNDYWGKGTLVTVSSG
GGGSGGGGSGGGGSQAVVTQEPSVTVSPGGTVTLTCGSDSGPVTRGHYPYWFQQKPGQAP
RTLIDDTSRKHSWTPARFSGSLLGGKAALTLSGAQPDDEADYYCLLSYSGEWVFGGGTKVT
VLTTTPAPRPPTPAPTIASQPLSLRPEACRPAAGGAVHTRGLDFACDIYIWAPLAGTCGVLLL
SLVITLYCKRGRKKLLYIFKQPFMRPVQTTQEEDGCSCRFPEEEEGGCELRVKFSRSADAPA
YKQGQNQLYNELNLGRREEYDVLDKRRGRDPEMGGKPRRKNPQEGLYNELQKDKMAEA
YSEIGMKGERRRGKGHDGLYQGLSTATKDTYDALHMQALPPR |
| 69 | GVQLVESGAEVKKPGASVKVSCKASGYTFTELSMHWVRQAPGKGLEWMGLVDPEDGETI
YAEKFQGRVTITADTSTDTAYMELSSLRSEDTAVYYCATDLAAGTNDYWGKGTLVTVSSG
GGGSGGGGSGGGGSQAVVTQEPSVTVSPGGTVTLTCGSDSGPVTRGHYPYWFQQKPGQAP
RTLIDDTSRKHSWTPARFSGSLLGGKAALTLSGAQPDDEADYYCLLSYSGEWVFGGGTKVT
VLTttpaprpptpaptiasqplslrpeacrpaaggavhtrgldfacdFwvlvvvggvlacysl
lvtvafiifwvRskrsrllhsdymnmtprrpgptrkhyqpyapprdfaayrsKrgrkkllyif
kqpfmrpvqttqeedgcscrfpeeeeggcelrvkfsrsadapayqqgqnqlynelnlgrreey
dvldkrrgrdpemggkpqrrknpqeglynelqkdkmaeayseigmkgerrrgkghdglyqgls
tatkdtydalhmqalppr |
| 70 | GVQLVESGAEVKKPGASVKVSCKASGYTFTELSMHWVRQAPGKGLEWMGLVDPEDGETI
YAEKFQGRVTITADTSTDTAYMELSSLRSEDTAVYYCATDLAAGTNDYWGKGTLVTVSSG
GGGSGGGGSGGGGSQAVVTQEPSVTVSPGGTVTLTCGSDTGAVTSGHYPYWFQQKPGQAP
RTLIYDTSNKHSWTPARFSGSLLGGKAALTLSGAQPDDEADYYCLLSYSGEWVFGGGTKVT
VLTttpaprpptpaptiasqplslrpeacrpaaggavhtrgldfacdFwvlvvvggvlacysl
lvtvafiifwvRskrsrllhsdymnmtprrpgptrkhyqpyapprdfaayrsvkfsrsadap |

TABLE 8-continued

Sequences

| SEQ ID NO: | Sequence |
|---|---|
| | ayqqgqnqlynelnlgrreeydvldkrrgrdpemggkpqrrknpqeglynelqkdkmaeayse igmkgerrrgkghdglyqglstatkdtydalhmqalppr |
| 71 | GVQLVESGAEVKKPGASVKVSCKASGYTFTELSMHWVRQAPGKGLEWMGLVDPEDGETI YAEKFQGRVTITADTSTDTAYMELSSLRSEDTAVYYCATDLAAGTNDYWGKGTLVTVSSG GGGSGGGGSGGGGSQAVVTQEPSVTVSPGGTVTLTCGSDTGAVTSGHYPYWFQQKPGQAP RTLIYDTSNKHSWTPARFSGSLLGGKAALTLSGAQPDDEADYYCLLSYSGEWVFGGGTKVT VLTTTPAPRPPTPAPTIASQPLSLRPEACRPAAGGAVHTRGLDFACDIYIWAPLAGTCGVLLL SLVITLYCKRGRKKLLYIFKQPFMRPVQTTQEEDGCSCRFPEEEEGGCELRVKFSRSADAPA YKQGQNQLYNELNLGRREEYDVLDKRRGRDPEMGGKPRRKNPQEGLYNELQKDKMAEA YSEIGMKGERRRGKGHDGLYQGLSTATKDTYDALHMQALPPR |
| 72 | GVQLVESGAEVKKPGASVKVSCKASGYTFTELSMHWVRQAPGKGLEWMGLVDPEDGETI YAEKFQGRVTITADTSTDTAYMELSSLRSEDTAVYYCATDLAAGTNDYWGKGTLVTVSSG GGGSGGGGSGGGGSQAVVTQEPSVTVSPGGTVTLTCGSDTGAVTSGHYPYWFQQKPGQAP RTLIYDTSNKHSWTPARFSGSLLGGKAALTLSGAQPDDEADYYCLLSYSGEWVFGGGTKVT VLTttpaprpptpaptiasqplslrpeacrpaaggavhtrgldfacdFwvlvvvggvlacysl lvtvafiifwvRskrsrllhsdymnmtprrpgptrkhyqpyapprdfaayrsKrgrkkllyif kqpfmrpvqttqeedgcscrfpeeeeggcelrvkfsrsadapayqqgqnqlynelnlgrreey dvldkrrgrdpemggkpqrrknpqeglynelqkdkmaeayseigmkgerrrgkghdglyqgls tatkdtydalhmqalppr |
| 73 | GVQLVESGAEVKKPGASVKVSCKASGYTFTELSMHWVRQAPGKGLEWMGLVVPADGETI YAEKFQGRVTITADTSTDTAYMELSSLRSEDTAVYYCATDLAAGTNDYWGKGTLVTVSSG GGGSGGGGSGGGGSQAVVTQEPSVTVSPGGTVTLTCGSDTGAVTSGHYPYWFQQKPGQAP RTLIYDTSNKHSWTPARFSGSLLGGKAALTLSGAQPDDEADYYCLLSYSGEWVFGGGTKVT VLTttpaprpptpaptiasqplslrpeacrpaaggavhtrgldfacdFwvlvvvggvlacysl lvtvafiifwvRskrsrllhsdymnmtprrpgptrkhyqpyapprdfaayrsvkfsrsadap ayqqgqnqlynelnlgrreeydvldkrrgrdpemggkpqrrknpqeglynelqkdkmaeayse igmkgerrrgkghdglyqglstatkdtydalhmqalppr |
| 74 | GVQLVESGAEVKKPGASVKVSCKASGYTFTELSMHWVRQAPGKGLEWMGLVVPADGETI YAEKFQGRVTITADTSTDTAYMELSSLRSEDTAVYYCATDLAAGTNDYWGKGTLVTVSSG GGGSGGGGSGGGGSQAVVTQEPSVTVSPGGTVTLTCGSDTGAVTSGHYPYWFQQKPGQAP RTLIYDTSNKHSWTPARFSGSLLGGKAALTLSGAQPDDEADYYCLLSYSGEWVFGGGTKVT VLTTTPAPRPPTPAPTIASQPLSLRPEACRPAAGGAVHTRGLDFACDIYIWAPLAGTCGVLLL SLVITLYCKRGRKKLLYIFKQPFMRPVQTTQEEDGCSCRFPEEEEGGCELRVKFSRSADAPA YKQGQNQLYNELNLGRREEYDVLDKRRGRDPEMGGKPRRKNPQEGLYNELQKDKMAEA YSEIGMKGERRRGKGHDGLYQGLSTATKDTYDALHMQALPPR |
| 75 | GVQLVESGAEVKKPGASVKVSCKASGYTFTELSMHWVRQAPGKGLEWMGLVVPADGETI YAEKFQGRVTITADTSTDTAYMELSSLRSEDTAVYYCATDLAAGTNDYWGKGTLVTVSSG GGGSGGGGSGGGGSQAVVTQEPSVTVSPGGTVTLTCGSDTGAVTSGHYPYWFQQKPGQAP RTLIYDTSNKHSWTPARFSGSLLGGKAALTLSGAQPDDEADYYCLLSYSGEWVFGGGTKVT VLTttpaprpptpaptiasqplslrpeacrpaaggavhtrgldfacdFwvlvvvggvlacysl lvtvafiifwvRskrsrllhsdymnmtprrpgptrkhyqpyapprdfaayrsKrgrkkllyif kqpfmrpvqttqeedgcscrfpeeeeggcelrvkfsrsadapayqqgqnqlynelnlgrreey dvldlargrdpemggkpqrrknpqeglynelqkdkmaeayseigmkgerrrgkghdglyqgls tatkdtydalhmqalppr |
| 76 | ggaagcattcagatagctcatcactctatcaatagtcactgcccgaattctgaaagcatgaag aagtatgcagagcttgattttagttttataaaaatccggttcttcaagggaggattttttgtgg cacagtctcactgttgaaattcagggcctgcatcagctcatcaataactgccagcatgttttg atctagaaagatctgcctcttaggatccatcagaagctttgcattcatggtcttgaactccac ctggtacatcttcaagtcttcataaatactactaaggcacagggccatcataaaagaggtctt tctggaggccaggcaactcccattagttatgaaagaggtctctctggaatttaggcaactctc attcttggttaattccaatggtaaacaggcctccactgtgctggttttatcttttgtgatatc ttcatgatcaatctcttcagaagtgcaagggtaaaattctaagtttgtctggccttctggag catgttgctgacggccctcagcaggttttgggagtggtgaaggcatgggaacattcctgggtc tggagtggccacggggaggtttctagatccgccgccacccgacccaccaccgcccgagccacc gccaccactgcagggcacagatgcccattcgctccaagatgagctatagtagcggtcctgggc ccgcacgctaatgctggcattttttgcggcagatgaccgtggctgaggtcttgtccgtgaagac tctatctttcttttctctcttgctcttgccctggacctgaacgcagaatgtcagggagaagta ggaatgtggagtactccaggtgtcagggtactcccagctgacctccacctgccgagaattctt taatggcttcagctgcaagttcttgggtgggtcaggtttgatgatgtccctgatgaagaagct gctggtgtagttttcatacttgagcttgtgaacggcatccaccatgacctcaatgggcagact ctcctcagcagctgggcaggcactgtcctcctggcactccactgagtactcatactccttgtt gtccctctgactctctctgcagagagtgtagcagctccgcacgtcaccccttgggggtcaga agagcctctgctgcttttgacactgaatgtcaaatcagtactgattgtcgtcagccaccagca ggtgaaacgtccagaataattcttggcctcgcatcttagaaaggtcttattttttgggttcttt ctggtcctttaaaatatcagtggaccaaattccatcttcctttttgtgaagcagcaggagcga atggcttagaacctcgcctcctttgtgacaggtgtactggccagcatctccaaactctttgac ttggatggtcaggttttgccagagcctaagacctcactgctctggtccaaggtccaggtgat |

TABLE 8-continued

Sequences

| SEQ ID NO: | Sequence |
|---|---|
| | accatcttcttcaggggtgtcacaggtgaggaccaccatttctccagggggcatccggatacca atccaattctacgacataaacatctttcttcagttcccatatggccacgaggggagatgccag aaaaaccagggaaaaccaagagatgaccaactgctggtgacacat |
| 77 | caggagttgaggttactgtgagtagtgattaaagagagtgatagggaactcttgaacaagaga tgcaatttatactgttaattctggaaaaatattatgggggtgtcaaaatgtcccgggacaatt gacgccttctgtatgaaacagttttcctccacgccttctgtatgaaacagttttcctccac gccttctgtatgaaacagttttcctccgtcgaggacaattgacgccttctgtatgaaacagt ttttcctccacgccttctgtatgaaacagttttcctccacgccttctgtatgaaacagtttt cctcc |
| 78 | atggtgagcaagggcgaggagctgttcaccggggtggtgcccatcctggtcgagctggacggc gacgtaaacggccacaagttcagcgtgtccggcgagggcgagggcgatgccacctacggcaag ctgaccctgaagttcatctgcaccaccggcaagctgcccgtgccctggcccaccctcgtgacc accctgacctacggcgtgcagtgcttcagccgctaccccgaccacatgaagcagcacgacttc ttcaagtccgccatgcccgaaggctacgtccaggagcgcaccatcttcttcaaggacgacggc aactacaagacccgcgccgaggtgaagttcgagggcgacaccctggtgaaccgcatcgagctg aagggcatcgacttcaaggaggacggcaacatcctggggcacaagctggagtacaactacaac agccacaacgtctatatcatggccgacaagcagaagaacggcatcaaggtgaacttcaagatc cgccacaacatcgaggacggcagcgtgcagctcgccgaccactaccagcagaacacccccatc ggcgacggccccgtgctgctgcccgacaaccactacctgagcacccagtccgccctgagcaaa gaccccaacgagaagcgcgatcacatggtcctgctggagttcgtgaccgccgcgggatcact ctcggcatggacgagctgtacaag |

What is claimed is:

1. An antigen binding unit comprising a light chain variable region and a heavy chain variable region, wherein the light chain variable region comprises LCDR1, LCDR2, and LCDR3; and the heavy chain variable region comprises HCDR1, HCDR2, and HCDR3, wherein said light chain variable region comprises SEQ ID NO:14, SEQ ID NO:15, and SEQ ID NO:13; and
wherein said heavy chain variable region comprises SEQ ID NO:8, SEQ ID NO:9, and SEQ ID NO:10.

2. The antigen binding unit of claim 1, wherein the antigen binding unit is a monoclonal antibody, humanized antibody, chimeric antibody, multiband antibody, chimeric antigen receptor, sFc, Fv, Fab, or (Fab)2.

3. A chimeric antigen receptor comprising an extracellular antigen binding unit, a transmembrane domain, and an intracellular domain,
   wherein the extracellular antigen binding unit comprises the antigen binding unit of claim 1.

4. A pharmaceutical composition comprising the antigen binding unit of claim 1, and a pharmaceutically acceptable excipient.

5. A method of inducing death of cells expressing WT1 or WT1 peptide, said method comprising contacting the cells with an immunoresponsive cell expressing the chimeric antigen receptor of claim 3, wherein the sequence of WT1 peptide is SEQ ID NO: 1.

6. The method of claim 5, wherein the cell is a rectal cancer cell or a mesothelioma cancer cell.

7. A method of treating a cancer which expresses WT1 or WT1 peptide in a subject in need thereof, said method comprising administering to the subject an effective amount of an immunoresponsive cell comprising the chimeric antigen receptor of claim 3, wherein the sequence of WT1 peptide is SEQ ID NO: 1.

8. The method of claim 7, wherein the cancer is a hematological cancer or a solid tumor.

9. The method of claim 7, wherein the cancer is mesothelioma.

10. The method of claim 7, wherein the cancer is nephroblastoma, colon cancer, rectal cancer, ovarian cancer, chronic myeloid leukemia, or intestinal cancer.

* * * * *

SEQUENCE LISTING

<160> NUMBER OF SEQ ID NOS: 83

<210> SEQ ID NO 1
<211> LENGTH: 9
<212> TYPE: PRT
<213> ORGANISM: Homo sapiens

<400> SEQUENCE: 1

Arg Met Phe Pro Asn Ala Pro Tyr Leu
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Tyr Ala Ile Ser
1               5

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Ile Ile Pro Ile Phe Gly Thr Ala Asn Tyr Ala Gln Lys Phe Gln
1               5                   10                  15

Gly

<210> SEQ ID NO 4

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Ser Ser Gly Trp Tyr Asn Trp Phe Asp Pro
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ala Ser Gln Ile Val Met Ser Asn Phe Leu Ala
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Ala Ser Arg Arg Val Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Gln Tyr Gly Ser Ser Pro Thr
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Leu Ser Met His
1               5

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9
```

Leu Val Asp Pro Glu Asp Gly Glu Thr Ile Tyr Ala Glu Lys Phe Gln
1               5                   10                  15

Gly

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Leu Ala Ala Gly Thr Asn Asp Tyr
1               5

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Ser Asp Thr Gly Ala Val Thr Ser Gly His Tyr Pro Tyr
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Thr Ser Asn Lys His Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Leu Ser Tyr Ser Gly Glu Trp Val
1               5

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Ser Asp Ser Gly Pro Val Thr Arg Gly His Tyr Pro Tyr
1               5                   10

<210> SEQ ID NO 15
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 15

Asp Thr Ser Arg Lys His Ser
1               5

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Val Val Pro Ala Asp Gly Glu Thr Ile Tyr Ala Glu Lys Phe Gln
1               5                   10                  15

Gly

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Val Val Pro Asp Asp Gly Glu Thr Ile Tyr Ala Glu Lys Phe Gln
1               5                   10                  15

Gly

<210> SEQ ID NO 18
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Ser Gly Trp Tyr Asn Trp Phe Asp Pro Trp Gly
            100                 105                 110

Arg Gly Thr Leu Val Thr Val Ser Ser
        115                 120

<210> SEQ ID NO 19
```

```
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagggaggt      300 agcagtggct ggtacaactg gttcgacccc tggggcagag gaaccctggt caccgtctcg     360
agt                                                                   363

<210> SEQ ID NO 20
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gly Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Glu Leu
            20                  25                  30

Ser Met His Trp Val Arg Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Ala Ala Gly Thr Asn Asp Tyr Trp Gly Lys Gly Thr
            100                 105                 110

Leu Val Thr Val Ser Ser
        115

<210> SEQ ID NO 21
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
ggggtgcagc tggtggagtc cggggctgag gtgaagaagc tggggcctc agtgaaggtc       60 tcctgcaagg cttctggata caccttcact gaattatcca tgcactgggt gcgacaggct     120
cctggaaaag ggcttgagtg gatgggactt gttgatcctg aagatggtga acaatatac      180 gcagagaagt tccagggcag agtcaccata accgcggaca cgtctacaga cacagcctac     240
atggagctga gcagcctgag atctgaggac acggccgtgt attactgtgc tacagaccta     300
```

```
gcagctggta ctaatgacta ctggggcaaa ggcaccctgg tcaccgtctc gagt          354
```

<210> SEQ ID NO 22
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Gly Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Glu Leu
            20                  25                  30

Ser Met His Trp Val Arg Gln Ala Pro Gly Lys Gly Leu Glu Trp Met
        35                  40                  45

Gly Leu Val Pro Ala Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Ala Ala Gly Thr Asn Asp Tyr Trp Gly Lys Gly Thr
            100                 105                 110

Leu Val Thr Val Ser Ser
        115
```

<210> SEQ ID NO 23
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
ggggtgcagc tggtggagtc cggggctgag gtgaagaagc ctggggcctc agtgaaggtc    60
tcctgcaagg cttctggata caccttcact gaattatcca tgcactgggt gcgacaggct   120
cctggaaaag gcttgagtg gatgggactt gttgtacctg ccgacggtga aacaatttac   180
gcagagaagt tccagggcag agtcaccata accgcggaca cgtctacaga cacagcctac   240
atggagctga gcagcctgag atctgaggac acggccgtgt attactgtgc cacagaccta   300
gcagctggta ctaatgacta ctggggcaaa ggcaccctgg tcaccgtctc gagt          354
```

<210> SEQ ID NO 24
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Gly Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Glu Leu
            20                  25                  30

Ser Met His Trp Val Arg Gln Ala Pro Gly Lys Gly Leu Glu Trp Met
        35                  40                  45
```

Gly Leu Val Val Pro Asp Asp Gly Glu Thr Ile Tyr Ala Glu Lys Phe
            50                  55                  60

Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Asp Leu Ala Ala Gly Thr Asn Asp Tyr Trp Gly Lys Gly Thr
            100                 105                 110

Leu Val Thr Val Ser Ser
        115

<210> SEQ ID NO 25
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
ggggtgcagc tggtggagtc cggggctgag gtgaagaagc tggggcctc agtgaaggtc        60 tcctgcaagg cttctggata caccttcact gaattatcca tgcactgggt gcgacaggct      120
cctggaaaag ggcttgagtg gatgggacta gttgttcctg atgatggtga aacaatatac      180
gcagagaagt tccagggcag agtcaccata accgcggaca cgtctacaga cacagcctac      240
atggagctga gcagcctgag atctgaggac acggccgtgt attactgtgc tacagaccta      300
gcagctggta ctaatgacta ctggggcaaa ggcaccctgg tcaccgtctc gagt            354

<210> SEQ ID NO 26
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Ile Val Met Thr Gln Ser Pro Gly Thr Leu Ser Leu Ser Pro Gly
 1               5                  10                  15

Glu Arg Ala Thr Leu Ser Cys Arg Ala Ser Gln Ile Val Met Ser Asn
             20                  25                  30

Phe Leu Ala Trp Tyr Gln Gln Lys Pro Gly Gln Ala Pro Arg Leu Leu
         35                  40                  45

Ile Tyr Gly Ala Ser Arg Arg Val Thr Gly Ile Pro Asp Arg Phe Ser
     50                  55                  60

Gly Ser Gly Ser Gly Thr Asp Phe Ser Leu Ile Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Thr Phe Gly Gln Gly Thr Lys Val Glu Ile Lys Arg
            100                 105

<210> SEQ ID NO 27
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
gaaattgtga tgacacagtc tccaggcacc ctgtctttgt ctccagggga aagggccacc    60
ctctcctgca gggccagtca gattgttatg agcaacttct tagcctggta ccagcagaaa   120
cctggccagg ctcccaggct cctcatctat ggtgcatcca ggagggtcac tggcatccca   180
gacaggttca gtggcagtgg gtctgggaca gacttcagtc tcatcatcag cagactggag   240
cctgaagatt ttgcagtgta ttactgtcag caatatggta gctcaccgac gttcggccaa   300
gggaccaagg tggaaatcaa acgt                                          324
```

<210> SEQ ID NO 28
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Gln Ala Val Val Thr Gln Glu Pro Ser Val Thr Val Ser Pro Gly Gly
1               5                   10                  15
Thr Val Thr Leu Thr Cys Gly Ser Asp Thr Gly Ala Val Thr Ser Gly
            20                  25                  30
His Tyr Pro Tyr Trp Phe Gln Gln Lys Pro Gly Gln Ala Pro Arg Thr
        35                  40                  45
Leu Ile Tyr Asp Thr Ser Asn Lys His Ser Trp Thr Pro Ala Arg Phe
    50                  55                  60
Ser Gly Ser Leu Leu Gly Gly Lys Ala Ala Leu Thr Leu Ser Gly Ala
65                  70                  75                  80
Gln Pro Asp Asp Glu Ala Asp Tyr Tyr Cys Leu Leu Ser Tyr Ser Gly
                85                  90                  95
Glu Trp Val Phe Gly Gly Gly Thr Lys Val Thr Val Leu
            100                 105
```

<210> SEQ ID NO 29
<211> LENGTH: 327
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

```
caggctgtgg tgactcagga gccctcagtg actgtgtccc caggagggac agtcactctc    60
acctgtggct ccgacactgg agctgtcacc agtggtcatt atccctactg gttccagcag   120
aagcctggcc aagcccccag gacactgatt tatgataca gcaacaaaca ctcctggaca    180
cctgcccggt tctcaggctc cctccttggg ggcaaagctg ccctgaccct ttcgggtgcg   240
cagcctgacg atgaggctga ctattactgc ttgctctcct atagtggtga atgggtgttc   300
ggcggaggga ccaaagtcac cgtccta                                       327
```

<210> SEQ ID NO 30
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

Gln Ala Val Val Thr Gln Glu Pro Ser Val Thr Val Ser Pro Gly Gly
1               5                   10                  15

Thr Val Thr Leu Thr Cys Gly Ser Asp Ser Gly Pro Val Thr Arg Gly
            20                  25                  30

His Tyr Pro Tyr Trp Phe Gln Gln Lys Pro Gly Gln Ala Pro Arg Thr
        35                  40                  45

Leu Ile Asp Asp Thr Ser Arg Lys His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Asp Asp Glu Ala Asp Tyr Tyr Cys Leu Leu Ser Tyr Ser Gly
                85                  90                  95

Glu Trp Val Phe Gly Gly Gly Thr Lys Val Thr Val Leu
            100                 105

<210> SEQ ID NO 31
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
caggctgtgg tgactcagga gccctcagtg actgtgtccc caggagggac agtcactctc        60
acctgtggct ccgactctgg accggtcacc cgagggcatt accctactg gttccagcag       120 aagcctggcc aagcccccag gacactgatt gatgatacaa gccgcaaaca ctcctggaca       180
cctgcccggt tctcaggctc cctccttggg ggcaaagctg ccctgaccct ttcgggtgcg       240
cagcctgacg atgaggctga ctattactgc ttgctctcct atagtggcga atgggtgttc       300
ggcggaggga ccaaagtcac cgtccta                                           327

<210> SEQ ID NO 32
<211> LENGTH: 901
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
atacatatgg gtagccatag catgcgctat tttttcacca gcgttagccg tccgggtcgt        60
ggtgaaccgc gttttattgc agttggttat gttgatgata cccagtttgt gcgctttgat       120
agtgatgcag caagccagcg tatggaaccg cgtgcaccgt ggattgaaca agaaggtccg       180
gaatattggg atggtgaaac ccgtaaagtt aaagcacata gccagaccca tcgtgttgat       240
ctgggcaccc tgcgtggcta ttataaccag agcgaagcag gttcacatac cgttcagcgt       300
atgtatggtt gtgatgttgg tagcgattgg cgttttctgc gtggttatca tcagtatgcc       360
tatgatggca aagattatat cgcccctgaaa gaagatctgc gtagctggac cgcagcagat       420
atggcagcac agaccaccaa acataaatgg gaagcagcac atgttgcaga acagctgcgt       480
gcatatctgg aaggcacctg tgttgaatgg ctgcgtcgtt atctggaaaa tggtaaagaa       540
accctgcagc gtaccgatgc accgaaaacc cacatgaccc atcatgcagt agcgatcat       600 gaagcaaccc tgcgttgttg ggcactgagc ttttatccgg cagaaatcac cctgacctgg       660

```
cagcgtgatg gtgaagatca gacccaggat accgaactgg ttgaaacacg tcctgccggt    720
gatggcacct ttcagaaatg ggcagcagtt gttgttccga gcggtcaaga acagcgttat    780
acctgtcatg ttcagcatga aggtctgccg aaaccgctga ccctgcgctg ggaaggtagc    840
ggtctgaatg atatttttga agcccagaaa atcgaatggc acgagtaata aggatccgcg    900
c                                                                    901
```

<210> SEQ ID NO 33
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
atatccatat gattcagcgt accccgaaaa ttcaggttta tagccgtcat ccggcagaaa     60
atggtaaaag caattttctg aattgctacg tgagcggttt tcatccgagc gatattgaag    120
ttgatctgct gaaaaatggc gaacgcattg aaaaagttga acatagcgat ctgagcttta    180
gcaaagattg gagcttttat ctgctgtact ataccgaatt taccccgacc gaaaagatg     240 aatatgcctg tcgtgttaat catgttaccc tgagccagcc gaaaattgtt aatgggatc     300 gtgatatgta ataaggatcc agtcg                                          325
```

<210> SEQ ID NO 34
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190
```

Ala Val Ser Asp His Glu Ala Thr Leu Arg Cys Trp Ala Leu Ser Phe
    195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Pro Ser Gly Gln Glu Gln Arg
            245                 250                 255

Tyr Thr Cys His Val Gln His Glu Gly Leu Pro Lys Pro Leu Thr Leu
        260                 265                 270

Arg Trp Glu
    275

<210> SEQ ID NO 35
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
atggccttac cagtgaccgc cttgctcctg ccgctggcct tgctgctcca cgccgccagg     60
ccg                                                                   63

<210> SEQ ID NO 36
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Met Ala Leu Pro Val Thr Ala Leu Leu Leu Pro Leu Ala Leu Leu Leu
1               5                   10                  15

His Ala Ala Arg Pro
            20

<210> SEQ ID NO 37
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
ggggtgcagc tggtggagtc cggggctgag gtgaagaagc tggggcctc agtgaaggtc      60 tcctgcaagg cttctggata caccttcact gaattatcca tgcactgggt gcgacaggct   120
cctggaaaag ggcttgagtg gatgggactt gttgatcctg aagatggtga acaatatac    180 gcagagaagt tccagggcag agtcaccata accgcggaca cgtctacaga cacagcctac   240
atggagctga gcagcctgag atctgaggac acggccgtgt attactgtgc tacagaccta   300
gcagctggta ctaatgacta ctgggggcaaa ggcaccctgg tcaccgtctc gagtggtgga  360
ggcggttcag gcggaggtgg ttctggcggt ggcggatcgc aggctgtggt gactcaggag   420
ccctcagtga ctgtgtcccc aggagggaca gtcactctca cctgtggctc cgactctgga  480
ccggtcaccc gagggcatta ccctactgg ttccagcaga gcctggcca agcccccagg     540

```
acactgattg atgatacaag ccgcaaacac tcctggacac ctgcccggtt ctcaggctcc    600
ctccttgggg gcaaagctgc cctgacccct tcgggtgcgc agcctgacga tgaggctgac    660
tattactgct tgctctccta tagtggcgaa tgggtgttcg gcggagggac caaagtcacc    720
gtccta                                                              726
```

```
<210> SEQ ID NO 38
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38
```

Gly Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Glu Leu
            20                  25                  30

Ser Met His Trp Val Arg Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Ala Ala Gly Thr Asn Asp Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Gln Ala Val Val Thr Gln Glu Pro Ser Val Thr
    130                 135                 140

Val Ser Pro Gly Gly Thr Val Thr Leu Thr Cys Gly Ser Asp Ser Gly
145                 150                 155                 160

Pro Val Thr Arg Gly His Tyr Pro Tyr Trp Phe Gln Gln Lys Pro Gly
                165                 170                 175

Gln Ala Pro Arg Thr Leu Ile Asp Asp Thr Ser Arg Lys His Ser Trp
            180                 185                 190

Thr Pro Ala Arg Phe Ser Gly Ser Leu Leu Gly Gly Lys Ala Ala Leu
        195                 200                 205

Thr Leu Ser Gly Ala Gln Pro Asp Asp Glu Ala Asp Tyr Tyr Cys Leu
    210                 215                 220

Leu Ser Tyr Ser Gly Glu Trp Val Phe Gly Gly Gly Thr Lys Val Thr
225                 230                 235                 240

Val Leu

```
<210> SEQ ID NO 39
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
accacgacgc cagcgccgcg accaccaaca ccggcgccca ccatcgcgtc gcagcccctg    60
```

```
tccctgcgcc cagaggcgtg ccggccagcg gcggggggcg cagtgcacac gagggggctg    120
gacttcgcct gtgat                                                    135

<210> SEQ ID NO 40
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 41
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ttttgggtgc tggtggtggt tggtggagtc ctggcttgct atagcttgct agtaacagtg    60
gcctttatta ttttctgggt g                                              81

<210> SEQ ID NO 42
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 43
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
aggagtaaga ggagcaggct cctgcacagt gactacatga acatgactcc ccgccgcccc    60
gggccaaccc gcaagcatta ccagccctat gccccaccac gcgacttcgc agcctatcgc    120
tcc                                                                  123

<210> SEQ ID NO 44
<211> LENGTH: 41
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 44

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 45
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgcag agaaggaaga accctcagga aggcctgtac     180
aatgaactgc agaaagataa gatggcgagc gcctacagtg agattgggat gaaaggcgag     240
cgccggaggg gcaaggggca cgatggcctt taccagggtc tcagtacagc caccaaggac     300
acctacgacg cccttcacat gcaggccctg ccccctcgc                            339

<210> SEQ ID NO 46
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 47
<211> LENGTH: 63
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 47
atctacatct gggcgcccctt ggccgggact tgtggggtcc ttctcctgtc actggttatc    60
acc    63

<210> SEQ ID NO 48
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 49
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
aaacggggca gaaagaaact cctgtatata ttcaaacaac catttatgag accagtacaa    60
actactcaag aggaagatgg ctgtagctgc cgatttccag aagaagaaga aggaggatgt   120
gaactg    126

<210> SEQ ID NO 50
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 51
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
ggggtgcagc tggtggagtc cggggctgag gtgaagaagc ctggggcctc agtgaaggtc    60
tcctgcaagg cttctggata caccttcact gaattatcca tgcactgggt gcgacaggct   120
cctggaaaag ggcttgagtg gatgggacta gttgttcctg atgatggtga aacaatatac   180

```
gcagagaagt tccagggcag agtcaccata accgcggaca cgtctacaga cacagcctac    240
atggagctga gcagcctgag atctgaggac acggccgtgt attactgtgc tacagaccta    300
gcagctggta ctaatgacta ctggggcaaa ggcaccctgg tcaccgtctc gagtggtgga    360
ggcggttcag gcggaggtgg ttctggcggt ggcggatcgc aggctgtggt gactcaggag    420
ccctcagtga ctgtgtcccc aggagggaca gtcactctca cctgtggctc cgacactgga    480
gctgtcacca gtggtcatta tccctactgg ttccagcaga agcctggcca agccccagg     540 acactgattt atgatacaag caacaaacac tcctggacac ctgcccggtt ctcaggctcc    600
ctccttgggg gcaaagctgc cctgaccctt tcgggtgcgc agcctgacga tgaggctgac    660
tattactgct tgctctccta tagtggtgaa tgggtgttcg gcggagggac caaagtcacc    720
gtccta                                                               726
```

<210> SEQ ID NO 52
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Gly Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Glu Leu
            20                  25                  30

Ser Met His Trp Val Arg Gln Ala Pro Gly Lys Gly Leu Glu Trp Met
        35                  40                  45

Gly Leu Val Val Pro Asp Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Ala Ala Gly Thr Asn Asp Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Ala Val Val Thr Gln Glu Pro Ser Val Thr
    130                 135                 140

Val Ser Pro Gly Gly Thr Val Thr Leu Thr Cys Gly Ser Asp Thr Gly
145                 150                 155                 160

Ala Val Thr Ser Gly His Tyr Pro Tyr Trp Phe Gln Gln Lys Pro Gly
                165                 170                 175

Gln Ala Pro Arg Thr Leu Ile Tyr Asp Thr Ser Asn Lys His Ser Trp
            180                 185                 190

Thr Pro Ala Arg Phe Ser Gly Ser Leu Leu Gly Gly Lys Ala Ala Leu
        195                 200                 205

Thr Leu Ser Gly Ala Gln Pro Asp Asp Glu Ala Asp Tyr Tyr Cys Leu
    210                 215                 220

Leu Ser Tyr Ser Gly Glu Trp Val Phe Gly Gly Thr Lys Val Thr
225                 230                 235                 240

Val Leu
```

```
<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Gly Gly Gly Ser Gly Gly Gly Gly Ser Gly Gly Gly Gly Ser
1               5                   10                  15

<210> SEQ ID NO 54
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gctttggttt ccaggtgcaa gatgtggggt gcagctggtg gagt                    44

<210> SEQ ID NO 55
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gatatcggat ccaccacctc ctaggacggt gactttggtc c                       41

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ggctaactag agaacccact gc                                            22

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
acatcttgca cctggaaacc aaagc                                         25

<210> SEQ ID NO 58
<211> LENGTH: 9
<212> TYPE: PRT
<213> ORGANISM: Unknown
<220> FEATURE:
<223> OTHER INFORMATION: Description of Unknown:
      Mediator complex subunit 13-like (MED13L) sequence

<400> SEQUENCE: 58

Arg Met Phe Pro Thr Pro Pro Ser Leu
1               5
```

<210> SEQ ID NO 59
<211> LENGTH: 9
<212> TYPE: PRT
<213> ORGANISM: Unknown
<220> FEATURE:
<223> OTHER INFORMATION: Description of Unknown: Phosphatidylinositol glycan anchor biosynthesis, class Q (PIGQ) sequence

<400> SEQUENCE: 59

Arg Met Phe Pro Gly Glu Val Ala Leu
1               5

<210> SEQ ID NO 60
<211> LENGTH: 239
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Leu Ile Asp Pro Trp Gly Gln Glu Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Thr Gly Arg Phe Asp Tyr Trp Gly Gln Gly Thr Leu Val
            100                 105                 110

Thr Val Ser Ser Gly Gly Gly Ser Gly Gly Gly Ser Gly Gly
        115                 120                 125

Gly Gly Ser Asp Ile Gln Met Thr Gln Ser Pro Ser Ser Leu Ser Ala
    130                 135                 140

Ser Val Gly Asp Arg Val Thr Ile Thr Cys Arg Ala Ser Gln Ser Ile
145                 150                 155                 160

Ser Ser Tyr Leu Asn Trp Tyr Gln Gln Lys Pro Gly Lys Ala Pro Lys
                165                 170                 175

Leu Leu Ile Tyr Ser Ala Ser Leu Leu Gln Ser Gly Val Pro Ser Arg
            180                 185                 190

Phe Ser Gly Ser Gly Ser Gly Thr Asp Phe Thr Leu Thr Ile Ser Ser
        195                 200                 205

Leu Gln Pro Glu Asp Phe Ala Thr Tyr Tyr Cys Gln Gln Gly Pro Gly
    210                 215                 220

Thr Pro Asn Thr Phe Gly Gln Gly Thr Lys Val Glu Ile Lys Arg
225                 230                 235

<210> SEQ ID NO 61
<211> LENGTH: 154
<212> TYPE: PRT
<213> ORGANISM: Artificial Sequence
<220> FEATURE:
<223> OTHER INFORMATION: Description of Artificial Sequence: Synthetic polypeptide -continued

<400> SEQUENCE: 61

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser Arg Val Lys Phe Ser Arg Ser
        35                  40                  45

Ala Asp Ala Pro Ala Tyr Gln Gln Gly Gln Asn Gln Leu Tyr Asn Glu
    50                  55                  60

Leu Asn Leu Gly Arg Arg Glu Glu Tyr Asp Val Leu Asp Lys Arg Arg
65                  70                  75                  80

Gly Arg Asp Pro Glu Met Gly Gly Lys Pro Gln Arg Arg Lys Asn Pro
                85                  90                  95

Gln Glu Gly Leu Tyr Asn Glu Leu Gln Lys Asp Lys Met Ala Glu Ala
            100                 105                 110

Tyr Ser Glu Ile Gly Met Lys Gly Glu Arg Arg Arg Gly Lys Gly His
        115                 120                 125

Asp Gly Leu Tyr Gln Gly Leu Ser Thr Ala Thr Lys Asp Thr Tyr Asp
    130                 135                 140

Ala Leu His Met Gln Ala Leu Pro Pro Arg
145                 150
```

<210> SEQ ID NO 62
<211> LENGTH: 155
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu Arg Val Lys Phe Ser Arg
        35                  40                  45

Ser Ala Asp Ala Pro Ala Tyr Gln Gln Gly Gln Asn Gln Leu Tyr Asn
    50                  55                  60

Glu Leu Asn Leu Gly Arg Arg Glu Glu Tyr Asp Val Leu Asp Lys Arg
65                  70                  75                  80

Arg Gly Arg Asp Pro Glu Met Gly Gly Lys Pro Gln Arg Arg Lys Asn
                85                  90                  95

Pro Gln Glu Gly Leu Tyr Asn Glu Leu Gln Lys Asp Lys Met Ala Glu
            100                 105                 110

Ala Tyr Ser Glu Ile Gly Met Lys Gly Glu Arg Arg Arg Gly Lys Gly
        115                 120                 125

His Asp Gly Leu Tyr Gln Gly Leu Ser Thr Ala Thr Lys Asp Thr Tyr
    130                 135                 140

Asp Ala Leu His Met Gln Ala Leu Pro Pro Arg
145                 150                 155
```

<210> SEQ ID NO 63
<211> LENGTH: 496
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gly Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Glu Leu
            20                  25                  30

Ser Met His Trp Val Arg Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Ala Ala Gly Thr Asn Asp Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Ala Val Val Thr Gln Glu Pro Ser Val Thr
    130                 135                 140

Val Ser Pro Gly Gly Thr Val Thr Leu Thr Cys Gly Ser Asp Ser Gly
145                 150                 155                 160

Pro Val Thr Arg Gly His Tyr Pro Tyr Trp Phe Gln Gln Lys Pro Gly
                165                 170                 175

Gln Ala Pro Arg Thr Leu Ile Asp Asp Thr Ser Arg Lys His Ser Trp
            180                 185                 190

Thr Pro Ala Arg Phe Ser Gly Ser Leu Leu Gly Gly Lys Ala Ala Leu
        195                 200                 205

Thr Leu Ser Gly Ala Gln Pro Asp Asp Glu Ala Asp Tyr Tyr Cys Leu
    210                 215                 220

Leu Ser Tyr Ser Gly Glu Trp Val Phe Gly Gly Gly Thr Lys Val Thr
225                 230                 235                 240

Val Leu Gly Gly Gly Gly Ser Asp Ile Lys Leu Gln Gln Ser Gly Ala
                245                 250                 255

Glu Leu Ala Arg Pro Gly Ala Ser Val Lys Met Ser Cys Lys Thr Ser
            260                 265                 270

Gly Tyr Thr Phe Thr Arg Tyr Thr Met His Trp Val Lys Gln Arg Pro
        275                 280                 285

Gly Gln Gly Leu Glu Trp Ile Gly Tyr Ile Asn Pro Ser Arg Gly Tyr
    290                 295                 300

Thr Asn Tyr Asn Gln Lys Phe Lys Asp Lys Ala Thr Leu Thr Thr Asp
305                 310                 315                 320

Lys Ser Ser Ser Thr Ala Tyr Met Gln Leu Ser Ser Leu Thr Ser Glu
                325                 330                 335

Asp Ser Ala Val Tyr Tyr Cys Ala Arg Tyr Tyr Asp Asp His Tyr Cys
            340                 345                 350

Leu Asp Tyr Trp Gly Gln Gly Thr Thr Leu Thr Val Ser Ser Val Glu
        355                 360                 365

Gly Gly Ser Gly Gly Ser Gly Gly Ser Gly Gly Ser Gly Gly Val Asp
    370                 375                 380

Asp Ile Gln Leu Thr Gln Ser Pro Ala Ile Met Ser Ala Ser Pro Gly

```
                385                 390                 395                 400
Glu Lys Val Thr Met Thr Cys Arg Ala Ser Ser Val Ser Tyr Met
                405                 410                 415

Asn Trp Tyr Gln Gln Lys Ser Gly Thr Ser Pro Lys Arg Trp Ile Tyr
                420                 425                 430

Asp Thr Ser Lys Val Ala Ser Gly Val Pro Tyr Arg Phe Ser Gly Ser
                435                 440                 445

Gly Ser Gly Thr Ser Tyr Ser Leu Thr Ile Ser Ser Met Glu Ala Glu
                450                 455                 460

Asp Ala Ala Thr Tyr Tyr Cys Gln Gln Trp Ser Ser Asn Pro Leu Thr
465                 470                 475                 480

Phe Gly Ala Gly Thr Lys Leu Glu Leu Lys His His His His His His
                485                 490                 495

<210> SEQ ID NO 64
<211> LENGTH: 1488
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
```

| | | | | | |
|---|---|---|---|---|---|
| ggggtgcagc | tggtggagtc | cggggctgag | gtgaagaagc | ctggggcctc | agtgaaggtc | 60 |
| tcctgcaagg | cttctggata | caccttcact | gaattatcca | tgcactgggt | gcgacaggct | 120 |
| cctggaaaag | gcttgagtg | gatgggactt | gttgatcctg | aagatggtga | aacaatatac | 180 |
| gcagagaagt | tccagggcag | agtcaccata | accgcggaca | cgtctacaga | cacagcctac | 240 |
| atggagctga | gcagcctgag | atctgaggac | acggccgtgt | attactgtgc | tacagaccta | 300 |
| gcagctggta | ctaatgacta | ctgggggcaaa | ggcacccctgg | tcaccgtctc | gagtggtgga | 360 |
| ggcggttcag | gcggaggtgg | ttctggcggt | ggcggatcgc | aggctgtggt | gactcaggag | 420 |
| ccctcagtga | ctgtgtcccc | aggagggaca | gtcactctca | cctgtggctc | cgactctgga | 480 |
| ccggtcaccc | gagggcatta | cccctactgg | ttccagcaga | agcctggcca | agcccccagg | 540 |
| acactgattg | atgatacaag | ccgcaaacac | tcctggacac | ctgcccggtt | ctcaggctcc | 600 |
| ctccttgggg | gcaaagctgc | cctgacccctt | tcgggtgcgc | agcctgacga | tgaggctgac | 660 |
| tattactgct | tgctctccta | tagtggcgaa | tgggtgttcg | gcggagggac | caaagtcacc | 720 |
| gtcctaggag | gtggtggatc | cgatatcaaa | ctgcagcagt | caggggctga | actggcaaga | 780 |
| cctgggggcct | cagtgaagat | gtcctgcaag | acttctggct | acacctttac | taggtacacg | 840 |
| atgcactggg | taaaacagag | gcctggacag | ggtctggaat | ggattggata | cattaatcct | 900 |
| agccgtggtt | atactaatta | caatcagaag | ttcaaggaca | aggccacatt | gactacagac | 960 |
| aaatcctcca | gcacagccta | catgcaactg | agcagcctga | catctgagga | ctctgcagtc | 1020 |
| tattactgtg | caagatatta | tgatgatcat | tactgccttg | actactgggg | ccaaggcacc | 1080 |
| actctcacag | tctcctcagt | cgaaggtgga | agtggaggtt | ctggtggaag | tggaggttca | 1140 |
| ggtggagtcg | acgacattca | gctgacccag | tctccagcaa | tcatgtctgc | atctccaggg | 1200 |
| gagaaggtca | ccatgacctg | cagagccagt | tcaagtgtaa | gttacatgaa | ctggtaccag | 1260 |
| cagaagtcag | gcacctcccc | caaaagatgg | atttatgaca | catccaaagt | ggcttctgga | 1320 |
| gtcccttatc | gcttcagtgg | cagtgggtct | gggacctcat | actctctcac | aatcagcagc | 1380 |
| atggaggctg | aagatgctgc | cacttattac | tgccaacagt | ggagtagtaa | cccgctcacg | 1440 | ttcggtgctg ggaccaagct ggagctgaaa catcatcacc atcatcat    1488

<210> SEQ ID NO 65
<211> LENGTH: 9
<212> TYPE: PRT
<213> ORGANISM: Unknown
<220> FEATURE:
<223> OTHER INFORMATION: Description of Unknown:
      Latent membrane protein-1 (LMP-1) sequence

<400> SEQUENCE: 65

Tyr Leu Leu Glu Met Leu Trp Arg Leu
1               5

<210> SEQ ID NO 66
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser Lys Arg Gly Arg Lys Lys Leu
        35                  40                  45

Leu Tyr Ile Phe Lys Gln Pro Phe Met Arg Pro Val Gln Thr Thr Gln
50                  55                  60

Glu Glu Asp Gly Cys Ser Cys Arg Phe Pro Glu Glu Glu Glu Gly Gly
65                  70                  75                  80

Cys Glu Leu Arg Val Lys Phe Ser Arg Ser Ala Asp Ala Pro Ala Tyr
                85                  90                  95

Gln Gln Gly Gln Asn Gln Leu Tyr Asn Glu Leu Asn Leu Gly Arg Arg
            100                 105                 110

Glu Glu Tyr Asp Val Leu Asp Lys Arg Arg Gly Arg Asp Pro Glu Met
        115                 120                 125

Gly Gly Lys Pro Gln Arg Arg Lys Asn Pro Gln Glu Gly Leu Tyr Asn
130                 135                 140

Glu Leu Gln Lys Asp Lys Met Ala Glu Ala Tyr Ser Glu Ile Gly Met
145                 150                 155                 160

Lys Gly Glu Arg Arg Arg Gly Lys Gly His Asp Gly Leu Tyr Gln Gly
                165                 170                 175

Leu Ser Thr Ala Thr Lys Asp Thr Tyr Asp Ala Leu His Met Gln Ala
            180                 185                 190

Leu Pro Pro Arg
        195

<210> SEQ ID NO 67
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gly Val Gln Leu Val Glu Ser Gly Ala Glu Val Lys Lys Pro Gly Ala
1               5                   10                  15

```
Ser Val Lys Val Ser Cys Lys Ala Ser Gly Tyr Thr Phe Thr Glu Leu
            20                  25                  30

Ser Met His Trp Val Arg Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Ala Ala Gly Thr Asn Asp Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Gln Ala Val Val Thr Gln Glu Pro Ser Val Thr
    130                 135                 140

Val Ser Pro Gly Gly Thr Val Thr Leu Thr Cys Gly Ser Asp Ser Gly
145                 150                 155                 160

Pro Val Thr Arg Gly His Tyr Pro Tyr Trp Phe Gln Gln Lys Pro Gly
            165                 170                 175

Gln Ala Pro Arg Thr Leu Ile Asp Asp Thr Ser Arg Lys His Ser Trp
        180                 185                 190

Thr Pro Ala Arg Phe Ser Gly Ser Leu Leu Gly Gly Lys Ala Ala Leu
    195                 200                 205

Thr Leu Ser Gly Ala Gln Pro Asp Asp Glu Ala Asp Tyr Tyr Cys Leu
210                 215                 220

Leu Ser Tyr Ser Gly Glu Trp Val Phe Gly Gly Gly Thr Lys Val Thr
225                 230                 235                 240

Val Leu Thr Thr Thr Pro Ala Pro Arg Pro Pro Thr Pro Ala Pro Thr
            245                 250                 255

Ile Ala Ser Gln Pro Leu Ser Leu Arg Pro Glu Ala Cys Arg Pro Ala
        260                 265                 270

Ala Gly Gly Ala Val His Thr Arg Gly Leu Asp Phe Ala Cys Asp Phe
    275                 280                 285

Trp Val Leu Val Val Val Gly Gly Val Leu Ala Cys Tyr Ser Leu Leu
290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
            325                 330                 335

Thr Arg Lys His Tyr Gln Pro Tyr Ala Pro Pro Arg Asp Phe Ala Ala
        340                 345                 350

Tyr Arg Ser Arg Val Lys Phe Ser Arg Ser Ala Asp Ala Pro Ala Tyr
    355                 360                 365

Gln Gln Gly Gln Asn Gln Leu Tyr Asn Glu Leu Asn Leu Gly Arg Arg
370                 375                 380

Glu Glu Tyr Asp Val Leu Asp Lys Arg Arg Gly Arg Asp Pro Glu Met
385                 390                 395                 400

Gly Gly Lys Pro Gln Arg Arg Lys Asn Pro Gln Glu Gly Leu Tyr Asn
            405                 410                 415

Glu Leu Gln Lys Asp Lys Met Ala Glu Ala Tyr Ser Glu Ile Gly Met
        420                 425                 430
```

```
Lys Gly Glu Arg Arg Gly Lys Gly His Asp Gly Leu Tyr Gln Gly
        435                 440                 445

Leu Ser Thr Ala Thr Lys Asp Thr Tyr Asp Ala Leu His Met Gln Ala
    450                 455                 460

Leu Pro Pro Arg
465

<210> SEQ ID NO 68
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gly Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Glu Leu
            20                  25                  30

Ser Met His Trp Val Arg Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Ala Ala Gly Thr Asn Asp Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Gln Ala Val Val Thr Gln Glu Pro Ser Val Thr
    130                 135                 140

Val Ser Pro Gly Gly Thr Val Thr Leu Thr Cys Gly Ser Asp Ser Gly
145                 150                 155                 160

Pro Val Thr Arg Gly His Tyr Pro Tyr Trp Phe Gln Gln Lys Pro Gly
                165                 170                 175

Gln Ala Pro Arg Thr Leu Ile Asp Asp Thr Ser Arg Lys His Ser Trp
            180                 185                 190

Thr Pro Ala Arg Phe Ser Gly Ser Leu Leu Gly Gly Lys Ala Ala Leu
        195                 200                 205

Thr Leu Ser Gly Ala Gln Pro Asp Asp Glu Ala Asp Tyr Tyr Cys Leu
    210                 215                 220

Leu Ser Tyr Ser Gly Glu Trp Val Phe Gly Gly Thr Lys Val Thr
225                 230                 235                 240

Val Leu Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Ile
        275                 280                 285

Tyr Ile Trp Ala Pro Leu Ala Gly Thr Cys Gly Val Leu Leu Leu Ser
    290                 295                 300

Leu Val Ile Thr Leu Tyr Cys Lys Arg Gly Arg Lys Lys Leu Leu Tyr
305                 310                 315                 320
```

```
Ile Phe Lys Gln Pro Phe Met Arg Pro Val Gln Thr Thr Gln Glu Glu
                325                 330                 335

Asp Gly Cys Ser Cys Arg Phe Pro Glu Glu Glu Gly Cys Glu
            340                 345                 350

Leu Arg Val Lys Phe Ser Arg Ser Ala Asp Ala Pro Ala Tyr Lys Gln
                355                 360                 365

Gly Gln Asn Gln Leu Tyr Asn Glu Leu Asn Leu Gly Arg Arg Glu Glu
            370                 375                 380

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
            420                 425                 430

Arg Arg Arg Gly Lys Gly His Asp Gly Leu Tyr Gln Gly Leu Ser Thr
            435                 440                 445

Ala Thr Lys Asp Thr Tyr Asp Ala Leu His Met Gln Ala Leu Pro Pro
            450                 455                 460

Arg
465

<210> SEQ ID NO 69
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gly Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Glu Leu
                20                  25                  30

Ser Met His Trp Val Arg Gln Ala Pro Gly Lys Gly Leu Glu Trp Met
            35                  40                  45

Gly Leu Val Asp Pro Glu Asp Gly Glu Thr Ile Tyr Ala Glu Lys Phe
        50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Ala Ala Gly Thr Asn Asp Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Ala Val Val Thr Gln Glu Pro Ser Val Thr
    130                 135                 140

Val Ser Pro Gly Gly Thr Val Thr Leu Thr Cys Gly Ser Asp Ser Gly
145                 150                 155                 160

Pro Val Thr Arg Gly His Tyr Pro Tyr Trp Phe Gln Gln Lys Pro Gly
                165                 170                 175

Gln Ala Pro Arg Thr Leu Ile Asp Asp Thr Ser Arg Lys His Ser Trp
            180                 185                 190

Thr Pro Ala Arg Phe Ser Gly Ser Leu Leu Gly Gly Lys Ala Ala Leu
```

195                 200                 205
Thr Leu Ser Gly Ala Gln Pro Asp Asp Glu Ala Asp Tyr Tyr Cys Leu
    210                 215                 220

Leu Ser Tyr Ser Gly Glu Trp Val Phe Gly Gly Gly Thr Lys Val Thr
225                 230                 235                 240

Val Leu Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Phe
        275                 280                 285

Trp Val Leu Val Val Val Gly Val Leu Ala Cys Tyr Ser Leu Leu
    290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
                325                 330                 335

Thr Arg Lys His Tyr Gln Pro Tyr Ala Pro Pro Arg Asp Phe Ala Ala
            340                 345                 350

Tyr Arg Ser Lys Arg Gly Arg Lys Lys Leu Leu Tyr Ile Phe Lys Gln
        355                 360                 365

Pro Phe Met Arg Pro Val Gln Thr Thr Gln Glu Glu Asp Gly Cys Ser
    370                 375                 380

Cys Arg Phe Pro Glu Glu Glu Gly Gly Cys Glu Leu Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Gln Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510

<210> SEQ ID NO 70
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gly Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Glu Leu
            20                  25                  30

Ser Met His Trp Val Arg Gln Ala Pro Gly Lys Gly Leu Glu Trp Met
        35                  40                  45

-continued

```
Gly Leu Val Asp Pro Glu Asp Gly Glu Thr Ile Tyr Ala Glu Lys Phe
 50                  55                  60

Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
             85                  90                  95

Ala Thr Asp Leu Ala Ala Gly Thr Asn Asp Tyr Trp Gly Lys Gly Thr
            100                 105                 110

Leu Val Thr Val Ser Ser Gly Gly Gly Ser Gly Gly Gly Gly Ser
            115                 120                 125

Gly Gly Gly Gly Ser Gln Ala Val Val Thr Gln Glu Pro Ser Val Thr
130                 135                 140

Val Ser Pro Gly Gly Thr Val Thr Leu Thr Cys Gly Ser Asp Thr Gly
145                 150                 155                 160

Ala Val Thr Ser Gly His Tyr Pro Tyr Trp Phe Gln Gln Lys Pro Gly
                165                 170                 175

Gln Ala Pro Arg Thr Leu Ile Tyr Asp Thr Ser Asn Lys His Ser Trp
            180                 185                 190

Thr Pro Ala Arg Phe Ser Gly Ser Leu Leu Gly Gly Lys Ala Ala Leu
            195                 200                 205

Thr Leu Ser Gly Ala Gln Pro Asp Asp Glu Ala Asp Tyr Tyr Cys Leu
210                 215                 220

Leu Ser Tyr Ser Gly Glu Trp Val Phe Gly Gly Thr Lys Val Thr
225                 230                 235                 240

Val Leu Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Phe
            275                 280                 285

Trp Val Leu Val Val Val Gly Gly Val Leu Ala Cys Tyr Ser Leu Leu
            290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
                325                 330                 335

Thr Arg Lys His Tyr Gln Pro Tyr Ala Pro Pro Arg Asp Phe Ala Ala
            340                 345                 350

Tyr Arg Ser Arg Val Lys Phe Ser Arg Ser Ala Asp Ala Pro Ala Tyr
            355                 360                 365

Gln Gln Gly Gln Asn Gln Leu Tyr Asn Glu Leu Asn Leu Gly Arg Arg
370                 375                 380

Glu Glu Tyr Asp Val Leu Asp Lys Arg Arg Gly Arg Asp Pro Glu Met
385                 390                 395                 400

Gly Gly Lys Pro Gln Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
            435                 440                 445

Leu Ser Thr Ala Thr Lys Asp Thr Tyr Asp Ala Leu His Met Gln Ala
450                 455                 460

Leu Pro Pro Arg
```

465

<210> SEQ ID NO 71
<211> LENGTH: 465
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 71

```
Gly Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Glu Leu
            20                  25                  30

Ser Met His Trp Val Arg Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Ala Ala Gly Thr Asn Asp Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Ala Val Val Thr Gln Glu Pro Ser Val Thr
    130                 135                 140

Val Ser Pro Gly Gly Thr Val Thr Leu Thr Cys Gly Ser Asp Thr Gly
145                 150                 155                 160

Ala Val Thr Ser Gly His Tyr Pro Tyr Trp Phe Gln Gln Lys Pro Gly
                165                 170                 175

Gln Ala Pro Arg Thr Leu Ile Tyr Asp Thr Ser Asn Lys His Ser Trp
            180                 185                 190

Thr Pro Ala Arg Phe Ser Gly Ser Leu Leu Gly Gly Lys Ala Ala Leu
        195                 200                 205

Thr Leu Ser Gly Ala Gln Pro Asp Asp Glu Ala Asp Tyr Tyr Cys Leu
    210                 215                 220

Leu Ser Tyr Ser Gly Glu Trp Val Phe Gly Gly Gly Thr Lys Val Thr
225                 230                 235                 240

Val Leu Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Ile
        275                 280                 285

Tyr Ile Trp Ala Pro Leu Ala Gly Thr Cys Gly Val Leu Leu Leu Ser
    290                 295                 300

Leu Val Ile Thr Leu Tyr Cys Lys Arg Gly Arg Lys Lys Leu Leu Tyr
305                 310                 315                 320

Ile Phe Lys Gln Pro Phe Met Arg Pro Val Gln Thr Thr Gln Glu Glu
                325                 330                 335

Asp Gly Cys Ser Cys Arg Phe Pro Glu Glu Glu Glu Gly Gly Cys Glu
            340                 345                 350
```

```
Leu Arg Val Lys Phe Ser Arg Ser Ala Asp Ala Pro Ala Tyr Lys Gln
        355                 360                 365

Gly Gln Asn Gln Leu Tyr Asn Glu Leu Asn Leu Gly Arg Arg Glu Glu
    370                 375                 380

Tyr Asp Val Leu Asp Lys Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
            420                 425                 430

Arg Arg Arg Gly Lys Gly His Asp Gly Leu Tyr Gln Gly Leu Ser Thr
        435                 440                 445

Ala Thr Lys Asp Thr Tyr Asp Ala Leu His Met Gln Ala Leu Pro Pro
    450                 455                 460

Arg
465

<210> SEQ ID NO 72
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gly Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Glu Leu
            20                  25                  30

Ser Met His Trp Val Arg Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Ala Ala Gly Thr Asn Asp Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Gln Ala Val Val Thr Gln Glu Pro Ser Val Thr
    130                 135                 140

Val Ser Pro Gly Gly Thr Val Thr Leu Thr Cys Gly Ser Asp Thr Gly
145                 150                 155                 160

Ala Val Thr Ser Gly His Tyr Pro Tyr Trp Phe Gln Gln Lys Pro Gly
                165                 170                 175

Gln Ala Pro Arg Thr Leu Ile Tyr Asp Thr Ser Asn Lys His Ser Trp
            180                 185                 190

Thr Pro Ala Arg Phe Ser Gly Ser Leu Leu Gly Gly Lys Ala Ala Leu
        195                 200                 205

Thr Leu Ser Gly Ala Gln Pro Asp Asp Glu Ala Asp Tyr Tyr Cys Leu
    210                 215                 220

Leu Ser Tyr Ser Gly Glu Trp Val Phe Gly Gly Gly Thr Lys Val Thr
225                 230                 235                 240
```

```
Val Leu Thr Thr Thr Pro Ala Pro Arg Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Phe
        275                 280                 285

Trp Val Leu Val Val Val Gly Gly Val Leu Ala Cys Tyr Ser Leu Leu
    290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
                325                 330                 335

Thr Arg Lys His Tyr Gln Pro Tyr Ala Pro Pro Arg Asp Phe Ala Ala
            340                 345                 350

Tyr Arg Ser Lys Arg Gly Arg Lys Lys Leu Leu Tyr Ile Phe Lys Gln
        355                 360                 365

Pro Phe Met Arg Pro Val Gln Thr Thr Gln Glu Glu Asp Gly Cys Ser
    370                 375                 380

Cys Arg Phe Pro Glu Glu Glu Gly Gly Cys Glu Leu Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Gln Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510

<210> SEQ ID NO 73
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gly Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Glu Leu
            20                  25                  30

Ser Met His Trp Val Arg Gln Ala Pro Gly Lys Gly Leu Glu Trp Met
        35                  40                  45

Gly Leu Val Val Pro Ala Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
```

```
                85                  90                  95
Ala Thr Asp Leu Ala Ala Gly Thr Asn Asp Tyr Trp Gly Lys Gly Thr
                100                 105                 110

Leu Val Thr Val Ser Ser Gly Gly Gly Gly Ser Gly Gly Gly Gly Ser
            115                 120                 125

Gly Gly Gly Ser Gln Ala Val Val Thr Gln Glu Pro Ser Val Thr
        130                 135                 140

Val Ser Pro Gly Gly Thr Val Thr Leu Thr Cys Gly Ser Asp Thr Gly
145                 150                 155                 160

Ala Val Thr Ser Gly His Tyr Pro Tyr Trp Phe Gln Gln Lys Pro Gly
                165                 170                 175

Gln Ala Pro Arg Thr Leu Ile Tyr Asp Thr Ser Asn Lys His Ser Trp
                180                 185                 190

Thr Pro Ala Arg Phe Ser Gly Ser Leu Leu Gly Gly Lys Ala Ala Leu
                195                 200                 205

Thr Leu Ser Gly Ala Gln Pro Asp Asp Glu Ala Asp Tyr Tyr Cys Leu
                210                 215                 220

Leu Ser Tyr Ser Gly Glu Trp Val Phe Gly Gly Gly Thr Lys Val Thr
225                 230                 235                 240

Val Leu Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
                260                 265                 270

Ala Gly Gly Ala Val His Thr Arg Gly Leu Asp Phe Ala Cys Asp Phe
                275                 280                 285

Trp Val Leu Val Val Val Gly Gly Val Leu Ala Cys Tyr Ser Leu Leu
                290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
                325                 330                 335

Thr Arg Lys His Tyr Gln Pro Tyr Ala Pro Pro Arg Asp Phe Ala Ala
                340                 345                 350

Tyr Arg Ser Arg Val Lys Phe Ser Arg Ser Ala Asp Ala Pro Ala Tyr
                355                 360                 365

Gln Gln Gly Gln Asn Gln Leu Tyr Asn Glu Leu Asn Leu Gly Arg Arg
                370                 375                 380

Glu Glu Tyr Asp Val Leu Asp Lys Arg Gly Arg Asp Pro Glu Met
385                 390                 395                 400

Gly Gly Lys Pro Gln Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
                420                 425                 430

Lys Gly Glu Arg Arg Arg Gly Lys Gly His Asp Gly Leu Tyr Gln Gly
                435                 440                 445

Leu Ser Thr Ala Thr Lys Asp Thr Tyr Asp Ala Leu His Met Gln Ala
                450                 455                 460

Leu Pro Pro Arg
465

<210> SEQ ID NO 74
<211> LENGTH: 465
<212> TYPE: PRT
<213> ORGANISM: Artificial Sequence
```

<220> FEATURE:
<223> OTHER INFORMATION: Description of Artificial Sequence: Synthetic polypeptide

<400> SEQUENCE: 74

```
Gly Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Glu Leu
            20                  25                  30

Ser Met His Trp Val Arg Gln Ala Pro Gly Lys Gly Leu Glu Trp Met
        35                  40                  45

Gly Leu Val Val Pro Ala Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Ala Ala Gly Thr Asn Asp Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Ala Val Val Thr Gln Glu Pro Ser Val Thr
    130                 135                 140

Val Ser Pro Gly Gly Thr Val Thr Leu Thr Cys Gly Ser Asp Thr Gly
145                 150                 155                 160

Ala Val Thr Ser Gly His Tyr Pro Tyr Trp Phe Gln Gln Lys Pro Gly
                165                 170                 175

Gln Ala Pro Arg Thr Leu Ile Tyr Asp Thr Ser Asn Lys His Ser Trp
            180                 185                 190

Thr Pro Ala Arg Phe Ser Gly Ser Leu Leu Gly Gly Lys Ala Ala Leu
        195                 200                 205

Thr Leu Ser Gly Ala Gln Pro Asp Asp Glu Ala Asp Tyr Tyr Cys Leu
    210                 215                 220

Leu Ser Tyr Ser Gly Glu Trp Val Phe Gly Gly Gly Thr Lys Val Thr
225                 230                 235                 240

Val Leu Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Ile
        275                 280                 285

Tyr Ile Trp Ala Pro Leu Ala Gly Thr Cys Gly Val Leu Leu Leu Ser
    290                 295                 300

Leu Val Ile Thr Leu Tyr Cys Lys Arg Gly Arg Lys Lys Leu Leu Tyr
305                 310                 315                 320

Ile Phe Lys Gln Pro Phe Met Arg Pro Val Gln Thr Thr Gln Glu Glu
                325                 330                 335

Asp Gly Cys Ser Cys Arg Phe Pro Glu Glu Glu Glu Gly Gly Cys Glu
            340                 345                 350

Leu Arg Val Lys Phe Ser Arg Ser Ala Asp Ala Pro Ala Tyr Lys Gln
        355                 360                 365

Gly Gln Asn Gln Leu Tyr Asn Glu Leu Asn Leu Gly Arg Arg Glu Glu
    370                 375                 380

Tyr Asp Val Leu Asp Lys Arg Arg Gly Arg Asp Pro Glu Met Gly Gly
```

```
                385                 390                 395                 400
Lys Pro Arg Arg Lys Asn Pro Gln Glu Gly Leu Tyr Asn Glu Leu Gln
                    405                 410                 415

Lys Asp Lys Met Ala Glu Ala Tyr Ser Glu Ile Gly Met Lys Gly Glu
                420                 425                 430

Arg Arg Arg Gly Lys Gly His Asp Gly Leu Tyr Gln Gly Leu Ser Thr
            435                 440                 445

Ala Thr Lys Asp Thr Tyr Asp Ala Leu His Met Gln Ala Leu Pro Pro
450                 455                 460

Arg
465

<210> SEQ ID NO 75
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gly Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Glu Leu
            20                  25                  30

Ser Met His Trp Val Arg Gln Ala Pro Gly Lys Gly Leu Glu Trp Met
        35                  40                  45

Gly Leu Val Val Pro Ala Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Ala Ala Gly Thr Asn Asp Tyr Trp Gly Lys Gly Thr
            100                 105                 110

Leu Val Thr Val Ser Ser Gly Gly Gly Ser Gly Gly Gly Gly Gly Ser
        115                 120                 125

Gly Gly Gly Gly Ser Gln Ala Val Val Thr Gln Glu Pro Ser Val Thr
    130                 135                 140

Val Ser Pro Gly Gly Thr Val Thr Leu Thr Cys Gly Ser Asp Thr Gly
145                 150                 155                 160

Ala Val Thr Ser Gly His Tyr Pro Tyr Trp Phe Gln Gln Lys Pro Gly
                165                 170                 175

Gln Ala Pro Arg Thr Leu Ile Tyr Asp Thr Ser Asn Lys His Ser Trp
            180                 185                 190

Thr Pro Ala Arg Phe Ser Gly Ser Leu Leu Gly Gly Lys Ala Ala Leu
        195                 200                 205

Thr Leu Ser Gly Ala Gln Pro Asp Asp Glu Ala Asp Tyr Tyr Cys Leu
    210                 215                 220

Leu Ser Tyr Ser Gly Glu Trp Val Phe Gly Gly Gly Thr Lys Val Thr
225                 230                 235                 240

Val Leu Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
            260                 265                 270
```

Ala Gly Gly Ala Val His Thr Arg Gly Leu Asp Phe Ala Cys Asp Phe
            275                 280                 285

Trp Val Leu Val Val Val Gly Gly Val Leu Ala Cys Tyr Ser Leu Leu
        290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
                325                 330                 335

Thr Arg Lys His Tyr Gln Pro Tyr Ala Pro Pro Arg Asp Phe Ala Ala
            340                 345                 350

Tyr Arg Ser Lys Arg Gly Arg Lys Lys Leu Leu Tyr Ile Phe Lys Gln
        355                 360                 365

Pro Phe Met Arg Pro Val Gln Thr Thr Gln Glu Glu Asp Gly Cys Ser
    370                 375                 380

Cys Arg Phe Pro Glu Glu Glu Glu Gly Gly Cys Glu Leu Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Gln Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510

<210> SEQ ID NO 76
<211> LENGTH: 1620
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
ggaagcattc agatagctca tcactctatc aatagtcact gcccgaattc tgaaagcatg      60
aagaagtatg cagagcttga ttttagtttt ataaaaatcc ggttcttcaa gggaggattt     120
ttgtggcaca gtctcactgt tgaaattcag ggcctgcatc agctcatcaa taactgccag     180
catgttttga tctagaaaga tctgcctctt aggatccatc agaagctttg cattcatggt     240
cttgaactcc acctggtaca tcttcaagtc ttcataaata ctactaaggc acagggccat     300
cataaaagag gtctttctgg aggccaggca actcccatta gttatgaaag aggtctctct     360
ggaatttagg caactctcat tcttggttaa ttccaatggt aaacaggcct ccactgtgct     420
ggttttatct tttgtgatat cttcatgatc aatctcttca gaagtgcaag ggtaaaattc     480
tagagtttgt ctggccttct ggagcatgtt gctgacggcc tcagcaggt tttgggagtg      540 gtgaaggcat gggaacattc tgggtctgg agtggccacg ggaggtttc tagatccgcc      600 gccacccgac ccaccaccgc ccgagccacc gccaccactg cagggcacag atgcccattc     660
gctccaagat gagctatagt agcggtcctg ggcccgcacg ctaatgctgg cattttgcg      720

```
gcagatgacc gtggctgagg tcttgtccgt gaagactcta tctttctttt ctctcttgct    780
cttgccctgg acctgaacgc agaatgtcag ggagaagtag gaatgtggag tactccaggt    840
gtcagggtac tcccagctga cctccacctg ccgagaattc tttaatggct tcagctgcaa    900
gttcttgggt gggtcaggtt tgatgatgtc cctgatgaag aagctgctgg tgtagttttc    960
atacttgagc ttgtgaacgg catccaccat gacctcaatg gcagactct cctcagcagc   1020 tgggcaggca ctgtcctcct ggcactccac tgagtactca tactccttgt tgtcccctct   1080
gactctctct gcagagagtg tagcagctcc gcacgtcacc ccttgggggt cagaagagcc   1140
tctgctgctt ttgacactga atgtcaaatc agtactgatt gtcgtcagcc accagcaggt   1200
gaaacgtcca gaataattct tggcctcgca tcttagaaag gtcttatttt tgggttcttt   1260
ctggtccttt aaaatatcag tggaccaaat tccatcttcc tttttgtgaa gcagcaggag   1320
cgaatggctt agaacctcgc ctcctttgtg acaggtgtac tggccagcat ctccaaactc   1380
tttgacttgg atggtcaggg ttttgccaga gcctaagacc tcactgctct ggtccaaggt   1440
ccaggtgata ccatcttctt cagggtgtc acaggtgagg accaccattt ctccaggggc   1500
atccggatac caatccaatt ctacgacata aacatctttc ttcagttccc atatggccac   1560
gaggggagat gccagaaaaa ccagggaaaa ccaagagatg accaactgct ggtgacacat   1620

<210> SEQ ID NO 77
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
caggagttga ggttactgtg agtagtgatt aaagagagtg atagggaact cttgaacaag     60
agatgcaatt tatactgtta attctggaaa aatattatgg gggtgtcaaa atgtcccggg    120
acaattgacg ccttctgtat gaaacagttt ttcctccacg ccttctgtat gaaacagttt    180
ttcctccacg ccttctgtat gaaacagttt ttcctccgtc gaggacaatt gacgccttct    240
gtatgaaaca gttttttcctc cacgccttct gtatgaaaca gttttttcctc cacgccttct    300 gtatgaaaca gttttttcctc c                                              321

<210> SEQ ID NO 78
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
```

```
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaag       717
```

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
     6xHis tag

<400> SEQUENCE: 79

His His His His His His
1               5

<210> SEQ ID NO 80
<211> LENGTH: 243
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 80

Gly Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Glu Leu
            20                  25                  30

Ser Met His Trp Val Arg Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Ala Ala Gly Thr Asn Asp Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Gln Ala Val Val Thr Gln Glu Pro Ser Val Thr
    130                 135                 140

Val Ser Pro Gly Gly Thr Val Thr Leu Thr Cys Gly Ser Asp Thr Gly
145                 150                 155                 160

Ala Val Thr Ser Gly His Tyr Pro Tyr Trp Phe Gln Gln Lys Pro Gly
                165                 170                 175

Gln Ala Pro Arg Thr Leu Ile Tyr Asp Thr Ser Asn Lys His Ser Trp
            180                 185                 190

Thr Pro Ala Arg Phe Ser Gly Ser Leu Gly Gly Lys Ala Ala Leu
        195                 200                 205

Thr Leu Ser Gly Ala Gln Pro Asp Asp Glu Ala Asp Tyr Tyr Cys Leu
    210                 215                 220

Leu Ser Tyr Ser Gly Glu Trp Val Phe Gly Gly Gly Thr Lys Val Thr
225                 230                 235                 240

Val Leu Thr

<210> SEQ ID NO 81
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gly Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Glu Leu
            20                  25                  30

Ser Met His Trp Val Arg Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Ala Ala Gly Thr Asn Asp Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Ala Val Val Thr Gln Glu Pro Ser Val Thr
    130                 135                 140

Val Ser Pro Gly Gly Thr Val Thr Leu Thr Cys Gly Ser Asp Ser Gly
145                 150                 155                 160

Pro Val Thr Arg Gly His Tyr Pro Tyr Trp Phe Gln Gln Lys Pro Gly
                165                 170                 175

Gln Ala Pro Arg Thr Leu Ile Asp Asp Thr Ser Arg Lys His Ser Trp
            180                 185                 190

Thr Pro Ala Arg Phe Ser Gly Ser Leu Leu Gly Gly Lys Ala Ala Leu
        195                 200                 205

Thr Leu Ser Gly Ala Gln Pro Asp Asp Glu Ala Asp Tyr Tyr Cys Leu
    210                 215                 220

Leu Ser Tyr Ser Gly Glu Trp Val Phe Gly Gly Thr Lys Val Thr
225                 230                 235                 240

Val Leu Thr

<210> SEQ ID NO 82
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gly Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Glu Leu
            20                  25                  30

Ser Met His Trp Val Arg Gln Ala Pro Gly Lys Gly Leu Glu Trp Met

```
        35                  40                  45
Gly Leu Val Val Pro Ala Asp Gly Glu Thr Ile Tyr Ala Glu Lys Phe
 50                  55                  60

Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Asp Leu Ala Ala Gly Thr Asn Asp Tyr Trp Gly Lys Gly Thr
                100                 105                 110

Leu Val Thr Val Ser Ser Gly Gly Gly Ser Gly Gly Gly Gly Ser
                115                 120                 125

Gly Gly Gly Ser Gln Ala Val Val Thr Gln Glu Pro Ser Val Thr
                130                 135                 140

Val Ser Pro Gly Gly Thr Val Thr Leu Thr Cys Gly Ser Asp Thr Gly
145                 150                 155                 160

Ala Val Thr Ser Gly His Tyr Pro Tyr Trp Phe Gln Gln Lys Pro Gly
                165                 170                 175

Gln Ala Pro Arg Thr Leu Ile Tyr Asp Thr Ser Asn Lys His Ser Trp
                180                 185                 190

Thr Pro Ala Arg Phe Ser Gly Ser Leu Leu Gly Gly Lys Ala Ala Leu
                195                 200                 205

Thr Leu Ser Gly Ala Gln Pro Asp Asp Glu Ala Asp Tyr Tyr Cys Leu
                210                 215                 220

Leu Ser Tyr Ser Gly Glu Trp Val Phe Gly Gly Thr Lys Val Thr
225                 230                 235                 240

Val Leu Thr

<210> SEQ ID NO 83
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gly Val Gln Leu Val Glu Ser Gly Ala Glu Val Lys Lys Pro Gly Ala
  1               5                  10                  15

Ser Val Lys Val Ser Cys Lys Ala Ser Gly Tyr Thr Phe Thr Glu Leu
                 20                  25                  30

Ser Met His Trp Val Arg Gln Ala Pro Gly Lys Gly Leu Glu Trp Met
             35                  40                  45

Gly Leu Val Val Pro Asp Asp Gly Glu Thr Ile Tyr Ala Glu Lys Phe
 50                  55                  60

Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Asp Leu Ala Ala Gly Thr Asn Asp Tyr Trp Gly Lys Gly Thr
                100                 105                 110

Leu Val Thr Val Ser Ser Gly Gly Gly Ser Gly Gly Gly Gly Ser
                115                 120                 125

Gly Gly Gly Gly Ser Gln Ala Val Val Thr Gln Glu Pro Ser Val Thr
                130                 135                 140

Val Ser Pro Gly Gly Thr Val Thr Leu Thr Cys Gly Ser Asp Thr Gly
```

-continued

```
            145                 150                 155                 160
        Ala Val Thr Ser Gly His Tyr Pro Tyr Trp Phe Gln Gln Lys Pro Gly
                        165                 170                 175

Gln Ala Pro Arg Thr Leu Ile Tyr Asp Thr Ser Asn Lys His Ser Trp
                        180                 185                 190

Thr Pro Ala Arg Phe Ser Gly Ser Leu Leu Gly Gly Lys Ala Ala Leu
                        195                 200                 205

Thr Leu Ser Gly Ala Gln Pro Asp Asp Glu Ala Asp Tyr Tyr Cys Leu
                210                 215                 220

Leu Ser Tyr Ser Gly Glu Trp Val Phe Gly Gly Gly Thr Lys Val Thr
        225                 230                 235                 240

Val Leu Thr
```